(12) United States Patent
Gu et al.

(10) Patent No.: US 11,730,765 B2
(45) Date of Patent: Aug. 22, 2023

(54) PLATELET COMPOSITIONS AND METHODS FOR THE DELIVERY OF THERAPEUTIC AGENTS

(71) Applicant: NORTH CAROLINA STATE UNIVERSITY, Raleigh, NC (US)

(72) Inventors: Zhen Gu, Apex, NC (US); Chao Wang, Raleigh, NC (US)

(73) Assignee: North Carolina State University, Raleigh, NC (US)

( * ) Notice: Subject to any disclaimer, the term of this patent is extended or adjusted under 35 U.S.C. 154(b) by 692 days.

(21) Appl. No.: 16/332,939

(22) PCT Filed: Sep. 13, 2017

(86) PCT No.: PCT/US2017/051376
§ 371 (c)(1),
(2) Date: Mar. 13, 2019

(87) PCT Pub. No.: WO2018/053010
PCT Pub. Date: Mar. 22, 2018

(65) Prior Publication Data
US 2019/0247438 A1    Aug. 15, 2019

Related U.S. Application Data

(60) Provisional application No. 62/393,839, filed on Sep. 13, 2016.

(51) Int. Cl.
| | | |
|---|---|---|
| A61K 39/395 | (2006.01) |
| A61K 35/19 | (2015.01) |
| A61K 47/68 | (2017.01) |
| A61K 47/69 | (2017.01) |
| A61K 45/06 | (2006.01) |
| A61K 39/40 | (2006.01) |
| A61P 35/00 | (2006.01) |
| A61P 9/10 | (2006.01) |
| C12N 5/078 | (2010.01) |
| C07K 16/28 | (2006.01) |
| A61P 35/04 | (2006.01) |
| A61K 47/10 | (2017.01) |
| A61K 39/00 | (2006.01) |

(52) U.S. Cl.
CPC .......... *A61K 35/19* (2013.01); *A61K 39/3955* (2013.01); *A61K 39/40* (2013.01); *A61K 45/06* (2013.01); *A61K 47/10* (2013.01); *A61K 47/6851* (2017.08); *A61K 47/69* (2017.08); *A61K 47/6901* (2017.08); *A61P 9/10* (2018.01); *A61P 35/00* (2018.01); *A61P 35/04* (2018.01); *C07K 16/2818* (2013.01); *C07K 16/2827* (2013.01); *C12N 5/0644* (2013.01); *A61K 2039/505* (2013.01)

(58) Field of Classification Search
CPC ................ A61K 35/19; A61K 39/3955; A61K 47/6901; A61K 47/6851
See application file for complete search history.

(56) References Cited

U.S. PATENT DOCUMENTS

| | | | |
|---|---|---|---|
| 3,266,987 A | 8/1966 | Crowley et al. | |
| 3,960,757 A | 6/1976 | Morishita et al. | |
| 4,460,563 A | 7/1984 | Calanchi | |
| 4,794,000 A | 12/1988 | Ecanow | |
| 5,019,400 A | 5/1991 | Gombotz et al. | |
| 6,143,211 A | 11/2000 | Mathiowitz et al. | |
| 6,620,617 B2 | 9/2003 | Mathiowitz et al. | |
| 8,217,149 B2 | 7/2012 | Irving et al. | |
| 8,685,394 B2 | 1/2014 | Jure-Kunkel | |
| 2005/0025748 A1* | 2/2005 | Nichols .................. | A61K 45/06 424/93.7 |
| 2010/0008937 A1 | 1/2010 | Peer et al. | |
| 2011/0038870 A1 | 2/2011 | Van Den Berg | |
| 2012/0009267 A1 | 1/2012 | Cho et al. | |
| 2013/0309250 A1* | 11/2013 | Cogswell ......... | G01N 33/57492 424/172.1 |
| 2016/0101128 A1 | 4/2016 | Wang et al. | |

FOREIGN PATENT DOCUMENTS

| | | |
|---|---|---|
| CN | 1822765 A | 8/2006 |
| JP | H8-109142 A | 8/2004 |
| WO | 93/21906 | 11/1993 |
| WO | 2005021706 A2 | 3/2005 |
| WO | 2006073446 A2 | 7/2006 |
| WO | 2006121168 A1 | 11/2006 |

OTHER PUBLICATIONS

Hofer et al., Arch. Surg., 1998, vol. 133(4):383-389.*
International Search Report and Written Opinion in PCT/US2017/051376, dated Dec. 28, 2017. 10 pages.
Sarkar S. et al. "Drug Delivery Using Platelet Cancer Cell Interaction". Pharm Res., 2013; 30(11), pp. 2785-2794.
Schlapschy M. et al. "PASylation: a biological alternative to PEGylation for extending the plasma half-life ofpharmnaceutically active proteins". Prot Eng, Des & Se!., 2013; 26(8), pp. 489-501.
Nawroth JF. et al. "Maleimide-Functionalized Poly(2-oxazoline)s and their conjugation to Elastin-like Polypeptides". Macromol Biosci., Mar. 2016 ; 16(3 ),pp. 322-333. doi: 10.1002/mabi. 201500376, pp. 1-24.
Weinstock M. et al. "Emerging role for novel immunotherapy agents in metastatic renal cell carcinoma: from bench to bedside". Am Soc Oncol Educ Book, 2015: e291-7, doi: 10.14694/EdBook_AM.105.35.e291, pp. 1-13, especially abstract, p. 1.

(Continued)

*Primary Examiner* — Xiaozhen Xie
(74) *Attorney, Agent, or Firm* — Meunier Carlin & Curfman LLC

(57) ABSTRACT

The present disclosure provides compositions and methods for targeted delivery of therapeutic agents. The present disclosure further provides methods for treating or preventing the metastasis or recurrence of a cancer using platelets loaded with a therapeutic agent (for example, an immunotherapeutic agent).

12 Claims, 33 Drawing Sheets

(56) References Cited

OTHER PUBLICATIONS

Baker, D., Masterson, T., Pace, R., Constable, W. & Wanebo, H. The influence of the surgical wound on local tumor recurrence. Surgery 106, 525-532 (1989).
Beck et al., New long-acting injectable microcapsule contraceptive system. Am J Obstet Gynecol 135(3) (1979) 419-426.
Beck et al., A new long-acting injectable microcapsule system for the administration of progesterone. Fertil. Steril., 31:545 (1979).
Benita et al., Characterization of drug-loaded poly (d, l-lactide) microspheres. J. Pharm. Sci., 73:1721 (1984).
Bianchini, G., Balko, J.M., Mayer, I.A., Sanders, M.E. & Gianni, L. Triple-negative breast cancer: challenges and opportunities of a heterogeneous disease. Nat. Rev. Clin. Oncol. 13(11): 674-690 (2016).
Boutros, C. et al. Safety profiles of anti-CTLA-4 and anti-PD-1 antibodies alone and in combination. Nat. Rev. Clin. Oncol. (2016).
Buchbinder, E.I. & Hodi, F.S. Melanoma in 2015: Immune-checkpoint blockade—durable cancer control. Nat. Rev. Clin. Oncol. 13, 77-78 (2016).
Cazenave, J.-P. et al. Preparation of washed platelet suspensions from human and rodent blood. Platelets and Megakaryocytes: vol. 1: Functional Assays, 13-28 (2004).
Ceelen, W., Pattyn, P. & Mareel, M. Surgery, wound healing, and metastasis: Recent insights and clinical implications. Crit. Rev. Oncol. Hematol. 89, 16-26 (2014).
Chen, L. & Han, X. Anti-PD-1/PD-L1 therapy of human cancer: past, present, and future. J. Clin. Invest. 125, 3384-3391 (2015).
Cheng, Y., Dendrimers as drug carriers: applications in different routes of drug administration. J. Pharm. Sci. (2007) 97:123-143.
Cheville, N.F. & Stasko, J. Techniques in electron microscopy of animal tissue. Veterinary pathology 51, 28-41 (2014).
Demicheli, R., Retsky, M., Hrushesky, W., Baum, M. & Gukas, I. The effects of surgery on tumor growth: a century of investigations. Ann. Oncol., mdn386 (2008).
Elzey, B.D. et al. Platelet-mediated modulation of adaptive immunity: A communication link between innate and adaptive immune compartments. Immunity 19, 9-19 (2003).
Fesnak, A.D., June, C.H. & Levine, B.L. Engineered T cells: the promise and challenges of cancer immunotherapy. Nat. Rev. Cancer 16, 566-581 (2016).
Flaumenhaft, R. Formation and fate of platelet microparticles. Blood Cells Mol. Dis. 36, 182-187 (2006).
Franco, A.T., Corken, A. & Ware, J. Platelets at the interface of thrombosis, inflammation, and cancer. Blood 126, 582-588 (2015).
Gajewski, T.F., Schreiber, H. & Fu, Y.X. Innate and adaptive immune cells in the tumor microenvironment. Nat. Immunol. 14, 1014-1022 (2013).
Garraud, O. Editorial: Platelets as immune cells in physiology and immunopathology. Front Immunol. 6, 1-3 (2015).
Gay, L.J. & Felding-Habermann, B. Contribution of platelets to tumour metastasis. Nat. Rev. Cancer 11, 123-134 (2011).
Harker, L.A. et al. Effects of megakaryocyte growth and development factor on platelet production, platelet life span, and platelet function in healthy human volunteers. Blood 95, 2514-2522 (2000).
Headley, M.B. et al. Visualization of immediate immune responses to pioneer metastatic cells in the lung. Nature 531, 513-517 (2016).
Hegde, P.S., Karanikas, V. & Evers, S. The where, the when, and the how of immune monitoring for cancer immunotherapies in the era of checkpoint inhibition. Clin. Cancer Res. 22, 1865-1874 (2016).
Hu, C.M. et al. Nanoparticle biointerfacing by platelet membrane cloaking. Nature 526, 118-121 (2015).
Hu, Q. et al. Anticancer Platelet-Mimicking Nanovehicles. Adv. Mater. 27, 7043-7050 (2015).
Janowska-Wieczorek, A. et al. Platelet-derived microparticles bind to hematopoietic stem/progenitor cells and enhance their engraftment after transplantation. Blood 98, 3143 (2001).
Klevorn, L.E. & Teague, R.M. Adapting Cancer Immunotherapy Models for the Real World. Trends Immunol. 37(6): 354-363 (2016).
Larkin, J. et al. Combined Nivolumab and Ipilimumab or Monotherapy in Untreated Melanoma. N. Engl. J. Med. 373, 23-34 (2015).
Li, J., Sharkey, C.C., Wun, B., Liesveld, J.L. & King, M.R. Genetic engineering of platelets to neutralize circulating tumor cells. J. Control Release 228, 38-47 (2016).
Lu, Y., Aimetti, A.A., Langer, R. & Gu, Z. Bioresponsive materials. Nature Reviews Materials 1, 16075 (2016).
Lukianova-Hleb, E.Y. et al. Intraoperative diagnostics and elimination of residual microtumours with plasmonic nanobubbles. Nat. Nanotechnol. (2016).
Mathiowitz et al., Morphology of polyanhydride microsphere delivery systems. J. Scanning Microscopy, 4:329 (1990).
Mathiowitz et al., Novel microcapsules for delivery systems. Reactive Polymers, 6:275 (1987).
Mause, S.F., von Hundelshausen, P., Zernecke, A., Koenen, R.R. & Weber, C. Platelet microparticles—A transcellular delivery system for RANTES promoting monocyte recruitment on endothelium. Arterioscler. Thromb. Vasc. Biol. 25, 1512-1518 (2005).
Mellati, M. et al. Anti-PD-1 and Anti-PDL-1 Monoclonal Antibodies Causing Type 1 Diabetes. Diabetes Care 38, e137-138 (2015).
Morrell, C.N., Aggrey, A.A., Chapman, L.M. & Modjeski, K.L. Emerging roles for platelets as immune and inflammatory cells. Blood 123, 2759-2767 (2014).
Naidoo, J. et al. Toxicities of the anti-PD-1 and anti-PD-L1 immune checkpoint antibodies. Ann. Oncol., 26:2375 (2015).
Nash, G.F., Turner, L.F., Scully, M.F. & Kakkar, A.K. Platelets and cancer. Lancet Oncol. 3, 425-430 (2002).
Nurden, A.T., Nurden, P., Sanchez, M., Andia, I. & Anitua, E. Platelets and wound healing. Front Biosci. 13, 3532-3548 (2008).
O'Sullivan, D. & Pearce, E.L. Targeting T cell metabolism for therapy. Trends Immunol. 36, 71-80 (2015).
Postow, M.A. et al. Nivolumab and ipilimumab versus ipilimumab in untreated melanoma. N. Engl. J. Med. 372, 2006-2017 (2015).
Pulaski, B.A. & Ostrand-Rosenberg, S. Mouse 4T1 breast tumor model. Curr. Protoc. Immunol. 20, 2 (2001).
Rand, M.L., Wang, H., Bang, K.W., Packham, M.A. & Freedman, J. Rapid clearance of procoagulant platelet-derived microparticles from the circulation of rabbits. J. Thromb Haemost 4, 1621-1623 (2006).
Robert, C. et al. Pembrolizumab versus Ipilimumab in Advanced Melanoma. N. Engl. J. Med. 372, 2521-2532 (2015).
Rosenberg, J.E. et al. Atezolizumab in patients with locally advanced and metastatic urothelial carcinoma who have progressed following treatment with platinum-based chemotherapy: a single-arm, multicentre, phase 2 trial. The Lancet 387, 1909-1920 (2016).
Ruggeri, Z.M. & Mendolicchio, G.L. Adhesion mechanisms in platelet function. Circ. Res. 100, 1673-1685 (2007).
Seifert, L. et al. The necrosome promotes pancreatic oncogenesis via CXCL1 and Mincle-induced immune suppression. Nature 532, 245-249 (2016).
Semple, J.W., Italiano, J.E. & Freedman, J. Platelets and the immune continuum. Nat. Rev. Immunol. 11, 264-274 (2011).
Sharma, P. & Allison, J.P. The future of immune checkpoint therapy. Science 348, 56-61 (2015).
Siljander, P.R.M. Platelet-derived microparticles—an updated perspective. Thromb. Res. 127, S30-S33 (2011).
Smit, E.F. & Baas, P. Lung cancer in 2015: Bypassing checkpoints, overcoming resistance, and honing in on new targets. Nat. Rev. Clin. Oncol. 13, 75-76 (2016).
Smyth, E.C. & Cunningham, D. Encouraging results for PD-1 inhibition in gastric cancer. Lancet Oncol. (2016).
Spranger, S. et al. Up-regulation of PD-L1, IDO, and Tregs in the melanoma tumor microenvironment is driven by CD8+ T cells. Sci. Transl. Med. 5, 200ra116-200ra116 (2013).
Stephan, S.B. et al. Biopolymer implants enhance the efficacy of adoptive T-cell therapy. Nat. Biotechnol. 33, 97-101 (2015).
Svenson, Sonke. "Dendrimers as versatile platform in drug delivery applications." European Journal of Pharmaceutics and Biopharmaceutics 71.3 (2009): 445-462.
Tamagawa-Mineoka, R. Important roles of platelets as immune cells in the skin. J. Dermatol. Sci. 77, 93-101 (2015).
Textor, J. in Platelet-Rich Plasma 61-94 (Springer, 2014).

(56) References Cited

OTHER PUBLICATIONS

Topalian, S.L., Drake, C.G. & Pardoll, D.M. Targeting the PD-1/B7-H1(PD-L1) pathway to activate anti-tumor immunity. Curr. Opin. Immunol. 24, 207-212 (2012).

Tripathi, S. & Guleria, I. Role of PD1/PDL1 pathway, and TH17 and treg cells in maternal tolerance to the fetus. Biomed. J. 38, 25-31 (2015).

Turajlic, S. & Swanton, C. Metastasis as an evolutionary process. Science352, 169-175 (2016).

Wang, Chao, et al. "In situ activation of platelets with checkpoint inhibitors for post-surgical cancer immunotherapy." Nature Biomedical Engineering1.2 (2017): 0011.

Wang, C., Ye, Y., Hochu, G.M., Sadeghifar, H. & Gu, Z. Enhanced Cancer Immunotherapy by Microneedle Patch-Assisted Delivery of Anti-PD1 Antibody. Nano Lett. 16, 2334-2340 (2016).

Weber, J.S., Kahler, K.C. & Hauschild, A. Management of immune-related adverse events and kinetics of response with ipilimumab. J. Clin. Oncol. 30, 2691-2697 (2012).

Woo, S.R., Corrales, L. & Gajewski, T.F. The STING pathway and the T cell-inflamed tumor microenvironment. Trends Immunol. 36, 250-256 (2015).

Yoo, J.W., Irvine, D.J., Discher, D.E. & Mitragotri, S. Bio-inspired, bioengineered and biomimetic drug delivery carriers. Nat. Rev. Drug Discov. 10, 521-535 (2011).

Zimmerman, M., Hu, X. & Liu, K. Experimental metastasis and CTL adoptive transfer immunotherapy mouse model. Journal of visualized experiments: JoVE (2010).

Zou, W., Wolchok, J.D. & Chen, L. PD-L1 (B7-H1) and PD-1 pathway blockade for cancer therapy: Mechanisms, response biomarkers, and combinations. Sci. Transl. Med. 8, 328rv4 (2016).

International Preliminary Report on Patentability issued for International Application No. PCT/US2017/051376, dated Mar. 28, 2019, 7 pages.

Communication pursuant to Article 94(3) EPC, issued for Application No. 17851460, dated Apr. 6, 2021.

Wang, Chao, et al. "In situ activation of platelets with checkpoint inhibitors for post-surgical cancer immunotherapy." Nature Biomedical Engineering 1.2 (2017): 1-10.

The Extended European Search Report issued for European Application No. 17851460, dated May 18, 2020.

Office Action and English translation dated Jul. 26, 2022, for Japanese Patent Application No. 2019-513929.

Federation Proceedings, 1986, vol. 45, No. 6, p. 1832.

Office Action and English translation dated Aug. 17, 2022, for Korean Patent Application No. 10-2019-7009451.

Office Action and English translation dated Sep. 19, 2022, for Chinese Patent Application No. 201780066511.5.

Sarkar, S., "Drug delivery using platelet cancer cell interaction," Pharm. Res., Jun. 6, 2013, 2785-2794.

* cited by examiner

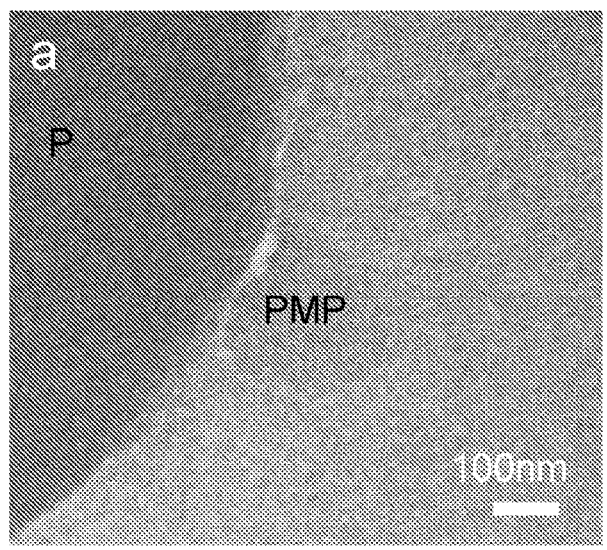
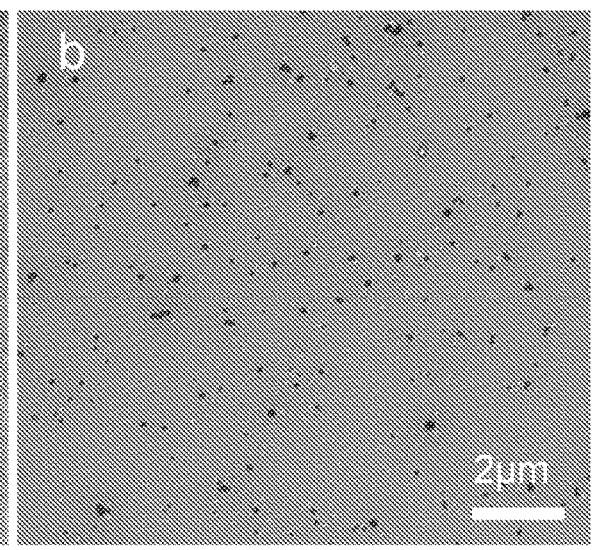
FIG. 10A                FIG. 10B
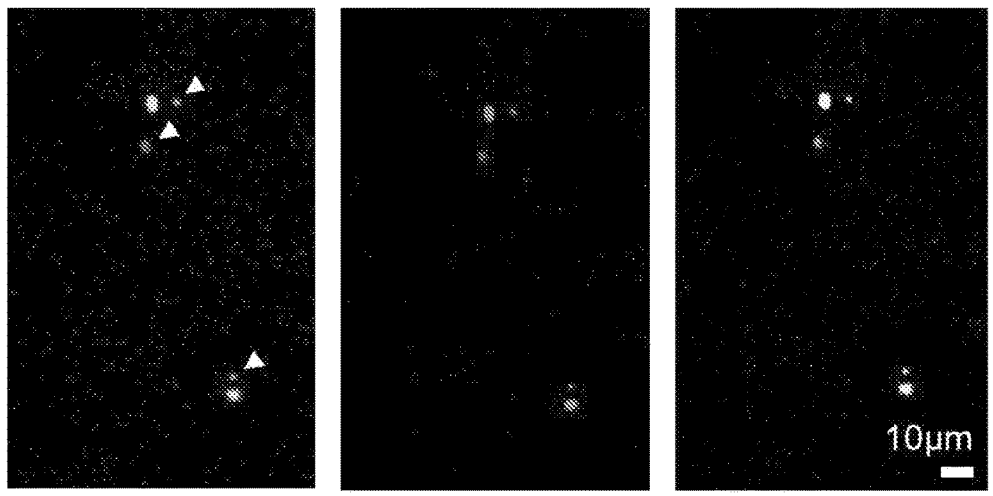
FIG. 11
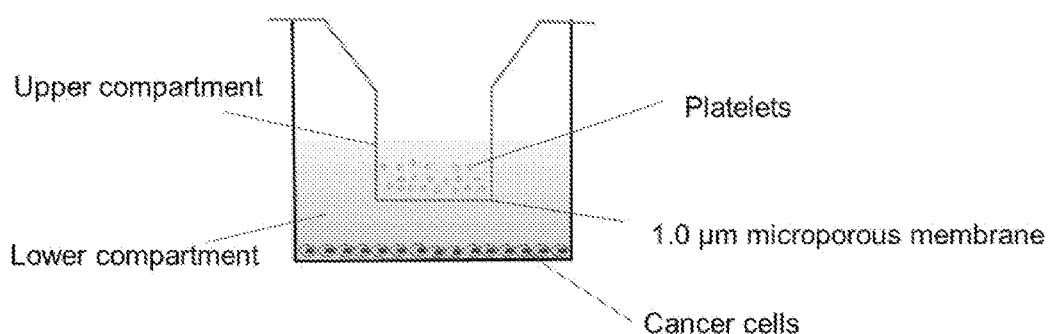
FIG. 12A Unactived P-aPDL1

Actived P-aPDL1

| | Free aPDL1 | | | P-aPDL1 | | |
|---|---|---|---|---|---|---|
| Liver | 11.05 | 10.78 | 10.02 | 7.244 | 8.860 | 8.491 |
| Spleen | 1.185 | 0.809 | 0.736 | 0.488 | 0.232 | 0.189 |
| Kidney | 0.410 | 0.299 | 1.100 | 0.603 | 1.009 | 0.500 |
| Heart | 0.450 | 0.141 | 0.092 | 0.526 | 0.129 | 0.090 |
| Lung | 1.364 | 1.142 | 1.043 | 0.906 | 0.715 | 0.656 |
| Wound with residual tumors | 0.017 | 0.0479 | 0.0335 | 2.029 | 1.442 | 1.219 |

PLATELET COMPOSITIONS AND METHODS FOR THE DELIVERY OF THERAPEUTIC AGENTS

CROSS REFERENCE TO RELATED APPLICATIONS

This application is a national stage application filed under 35 U.S.C. § 371 of PCT/US2017/051376 filed Sep. 13, 2017, which claims the benefit of U.S. Provisional Patent Application Ser. No. 62/393,839 filed Sep. 13, 2016, the disclosures of which are expressly incorporated herein by reference.

FIELD

The present disclosure provides compositions and methods for targeted delivery of therapeutic agents. The present disclosure further provides methods for treating or preventing the metastasis or recurrence of a cancer using platelets loaded with a therapeutic agent (for example, an immunotherapeutic agent).

BACKGROUND

Surgery is the main treatment option for most solid tumors. Despite continual improvements in surgical techniques, residual microtumors and/or circulating tumor cells (CTCs) after tumor resection remain challenging. Additionally, it has also been suggested that surgery can induce the promotion of cancer metastasis. Many patients develop recurrent disease post-surgery, which can lead to significant morbidity as well as mortality. Hence, there has been tremendous interest in developing effective strategies to prevent cancer recurrence after surgery. Among them, cancer immunotherapy has received considerable attention recently. Immunotherapeutic agents do not directly attack the tumor, but boost the body's immune system to kill the cancer cells. The immune checkpoint blockade has elicited durable antitumor responses and long-term remissions in a subset of patients. Particularly, the checkpoint inhibitors block the interaction with programmed cell death protein 1 (PD1) on lymphocytes and programmed cell death 1 ligand 1 (PDL1) on antigen presenting cells (APCs) and tumor cells have shown exciting results in treating various types of cancer. Moreover, the first PD-L1 inhibitor, atezolizumab, has been granted accelerated approval by FDA recently. Despite remarkable progress, current methods of checkpoint blockade therapy limit the therapeutic benefits in many patients. The largest limitation observed in clinical trials may be the severity of the side effects, such as autoimmune disorders. The grade ¾ adverse events have sometimes occurred when treated with immune checkpoint blockade therapy. Meanwhile, a large fraction of patients failed to response to these agents. The objective response rate (ORR) of cancer immunotherapy still needs improvement. How to enhance cancer immunotherapy has become one of the central themes in the field of cancer immunology and immunotherapy. The compositions and methods disclosed herein address these and other needs.

SUMMARY

The present disclosure provides platelet compositions and methods for the treatment and prevention of disease, for example, a cancer. In the compositions and methods disclosed herein, a therapeutic agent (for example, an immunotherapeutic agent) is covalently linked to a platelet cell. The inventors have found that an immunotherapeutic agent (for example, anti-PDL1) conjugated to the surface of a platelet cell reduces the recurrence of a cancer (and/or reduces metastasis) after resection of a primary tumor.

In one aspect, provided herein is a composition comprising:
a platelet cell;
a chemical linker moiety; and
a therapeutic agent;
wherein the therapeutic agent is covalently linked to the platelet cell through the chemical linker moiety.

In another aspect, disclosed herein is a method of preventing metastasis or recurrence of a cancer, comprising: administering to a subject in need thereof a therapeutically effective amount of a composition comprising:
a platelet cell;
a chemical linker moiety; and
a therapeutic agent;
wherein the therapeutic agent is covalently linked to the platelet cell through the chemical linker moiety.

In a further aspect, disclosed herein is a method for the targeted delivery of a therapeutic agent comprising: administering to a subject a composition comprising:
a platelet cell;
a chemical linker moiety; and
a therapeutic agent;
wherein the therapeutic agent is covalently linked to the platelet cell through the chemical linker moiety;
wherein the composition is targeted to a wound or surgical resection site through activation of the platelet cell.

In an additional aspect, provided herein is a method of treating or preventing vascular disease, comprising: administering to a subject in need thereof a therapeutically effective amount of a composition comprising:
a platelet cell;
a chemical linker moiety; and
a therapeutic agent;
wherein the therapeutic agent is covalently linked to the platelet cell through the chemical linker moiety.

BRIEF DESCRIPTION OF THE DRAWINGS

The accompanying figures, which are incorporated in and constitute a part of this specification, illustrate several aspects described below.

(FIG. 1a) Schematic illustration of delivery of anti-PDL1 antibody (aPDL1) toward the primary tumor resection site by platelets. (FIG. 1b) TEM imaging of P-aPDL1 before (i) and after (ii and iii) activation. The red arrows indicated the PMPs released from platelet. A large amount of generated PMPs particles were observed under the electron microscopy. Scale bar, 0.5 µm. (FIG. 1c) Percentage of released aPDL1 from nonactivated and activated platelets at different time points. (FIG. 1d-FIG. 1e) Amount of TNF-α (f) and IL-1β (FIG. 1g) released from nonactivated and activated platelets at different time points. (FIG. 1f) Confocal immunofluorescence images of B16 cancer cells co-incubated with nonactivated (left) and activated (right) P-aPDL1 in a transwell system (pore size, 1 µm). P-aPDL1 and B16 cancer cells were cultured in upper and lower compartments, respectively. Red colors represent aPDL1 signals, blue and green fluorescence represent nucleus and plasma membrane from DAPI and Alexa fluor 488 conjugate wheat germ agglutinin, respectively. Scale bar, 20 µm. The error bars are based on the standard deviations (SD) of triplicated samples.

(FIG. 2a) Blood-circulation curves of P-aPDL1, free aPDL1 and Platelets+aPDL1 mixture in mice by measuring the level of aPDL1 in the blood collected at different time points post injection. The error bars are based on the standard deviations (SD) of triplicated samples (n=3) (FIG. 2b) Fluorescence imaging (aPDL1-Cy5.5) of the mice after i.v. injection of P-aPDL1 or an equivalent dose of free aPDL1 2 hours post injection. (FIG. 2c) Ex vivo imaging of wounds with residual tumors 2 h after i.v. injection of P-aPDL1 or free aPDL1. (FIG. 2d) The mean aPDL1-Cy5.5 fluorescent signal intensities in the different wounds of mice shown in (c). The error bars are based on the standard error of the mean (s.e.m.) of triplicated samples. (FIG. 2e) Confocal images of the residual tumor slices taken from the mice as showed in (b), where blue and red represent nucleus and aPDL1 signals from DAPI and Cy5.5, respectively. Scale bar, 20 µm. (FIG. 2f) Schematic illustration of P-aPDL1 therapy for treatment of an incomplete surgery tumor model. (FIG. 2g) In vivo bioluminescence imaging of the B16F10 tumors of the different groups after removal of the primary tumor. Shown were 3 representative mice per treatment group. (FIG. 2h) Quantified tumor signals of the different groups of mice after various treatments indicated. (FIG. 2i-FIG. 2j) Tumor growth curves (i) and survival curves (j) of the treated and control mice. Shown were 8 mice per treatment group for survival study. The error bars are based on the standard error of the mean (s.e.m.). P value: *, $P<0.05$.

(FIG. 3a) Immunofluorescence of residual tumors showed CD4+ T cells and CD8+ T cells infiltration. Scale bar, 50 µm. (FIG. 3b) Tumor weights and (FIG. 3c) Absolute numbers of CD3+ cells per gram of tumor. The error bars are based on the standard error of the mean (s.e.m.) (n=4). (FIG. 3d) Percentages of CD4+ and CD8+ T cells of total CD3+ cells, and representative dot plots in residual tumor of mice treated as indicated. The higher cell populations in all four quadrants indicated much more CD3+ tumor-infiltrating lymphocytes in the tumor site. (FIG. 3e) Percentage of CD4+Foxp3+ T cells of total CD3+ cells, and representative dot plots in residual tumor of mice treated as indicated. (FIG. 3f) Absolute number of the CD8+ cells per gram of the tumor upon various treatments. (FIG. 3g-FIG. 3h) Ratios of the tumor-infiltrating CD8+ T cells and effective CD4+ T cells over regulatory T cells in the residual tumors upon various treatments. The error bars are based on the standard error of the mean (s.e.m) (n=4). Statistical significance was calculated by one-way ANOVA using the Tukey post-test. P value: *, $P<0.05$; , $P<0.01$; *$P<0.005$.

(FIG. 4a) Schematic illustration of P-aPDL1 therapy for treatment of an incomplete surgery and metastatic tumor model of mouse. (FIG. 4b) In vivo bioluminescence imaging of the B16F10 metastasis of different groups after removal of the primary tumors at different time points. Shown were 3 representative mice per treatment group. (FIG. 4c) Representative lung photographs and (FIG. 4d) H&E-stained lung slices collected from the mice post different treatments indicated. The black arrows indicated the metastatic tumors in the lung. Scale bar, 500 µm. (FIG. 4e) Quantification of the lung metastasis nodules for the mice with different treatments. Results are presented as the mean±SEM (n=3). (FIG. 4f) Survival curves for the treated and control mice. Shown were 8 mice per treatment group for survival study. P value: *, $P<0.05$.

(FIG. 5a) In vivo bioluminescence imaging of the 4T1 metastasis of the different groups after removing of the primary tumors at different time points. (FIG. 5b) Representative mice photographs 2 weeks after surgery. Black arrows indicate the recurrent tumor in surgical bed. (FIG. 5c) Representative lung photographs collected from the mice post different treatments indicated. Red arrows indicated the tumor nodules in the lung. (FIG. 5d) Quantification of the lung metastasis nodules for the mice with different treatments. Results are presented as the mean±SEM (n=3). (FIG. 5e) Survival curves for treated and control mice. Shown are 8 mice per each treatment group for survival study. P value: *, $P<0.05$.

(FIG. 8a) Various amounts of aPDL1 were added into platelets for conjugation. The efficiency of aPDL1 conjugation (added aPDL1/conjugated aPDL1) to platelets was about 75% when 0.2 pg aPDL1 per platelet was added. (FIG. 8b) Stability of platelets after aPDL1 modification. The number of P-aPDL1 was measured based on the platelet count analysis at the 0 h and 24 h. (FIG. 8c) Stability of aPDL1 on platelets over time. The error bars are based on the standard deviations (SD) of triplicated samples (n=6).

FIGS. 10A-10B. Transmission electron microscopy (TEM) of P-aPDL1 after activation. (FIG. 10a) Platelet microparticles (PMPs) shed from activated platelets. (FIG. 10b) A number of PMPs can be found under TEM after P-aPDL1 activation. Size bars, 100 nm in FIG. 10a and 2 µm in FIG. 10b.

FIG. 11. Immunofluorescence imaging of P-aPDL1 after activation. Platelets were loaded with calcein and visualized by green fluorescence. aPDL1 were labeled with Cy3 Goat anti-rat IgG secondary antibody and visualized by the red fluorescence. The white arrows indicated the PMPs released from platelet.

FIGS. 12A-12B. Confocal immunofluorescence images of B16 cancer cells co-incubated with P-aPDL1 in a transwell system. (FIG. 12a) A schematic of the transwell system. P-aPDL1 and B16 cancer cells were cultured in the upper and lower compartments, respectively. (FIG. 12b) Confocal immunofluorescence images of B16 cancer cells co-incubated with nonactivated and activated P-aPDL1 in a transwell system (pore size, 1 µm). Red (Cy3) fluorescence represents the aPDL1 signal, blue (DAPI) and green (Alexa Fluor® 488) fluorescence represent the signals from nucleus and cell membrane, respectively. Scale bar, 20 µm.

(FIG. 13a) Fluorescence spectra of free Cy5.5-aPDL1 and P-aPDL1-Cy5.5. The intensity of Cy5.5 was not found affected significantly after aPDL1 conjugated to platelets. (FIG. 13b) Ex vivo Cy5.5-aPDL1 fluorescence imaging in different organs of mice 2 h after i.v. injection of P-aPDL1 and free aPDL1. L: liver, Lu: lung, Sp: spleen, H: heart, K: kidney. (FIG. 13c) The mean Cy5.5 fluorescence signal intensities in different organs of mice shown in (b). Shown are 3 mice per each treatment group. Results were presented as the mean±SD. Statistical significance was calculated by t-test. P value: ***, P<0.005.

(FIG. 14a) Confocal images of the residual tumor slices, where blue and red represent nucleus and aPDL1 signals from DAPI and Cy5.5. (FIG. 14b) High magnification images of residual tumor slices in P-aPDL1 of (a). The white arrows indicated the PMPs and aPDL1 released from platelets.

(FIG. 16a) Local and (FIG. 16b) systematic cytokine levels of mice after treatments indicated. (FIG. 16c) The representative flow cytometric analysis images and (FIG. 16d) the immunofluorescence image (up, W/O platelets; down, W/platelets) of PD-L1 analyses. (Macrophage gated on CD11b+ GFP−, Tumor cells gated on GFP+, CD45−, B cell gated on CD20+ GFP− and DC gated on CD11c+ GFP−). The error bars are based on the s.e.m. of triplicated samples. Statistical significance was calculated by one-way ANOVA using the Tukey post-test. P value: *, P<0.05, n.s., non-significant.

(FIG. 19a) In vivo bioluminescence imaging of the B16F10 tumors of the different groups after removal of the primary tumor. (FIG. 19b) Tumor growth curves of the different groups of mice after various treatments indicated. (FIG. 19c) The survival curves of mice in 60 days after various treatments indicated. Shown are 5 mice per each treatment group.

DETAILED DESCRIPTION

Figure 1A:
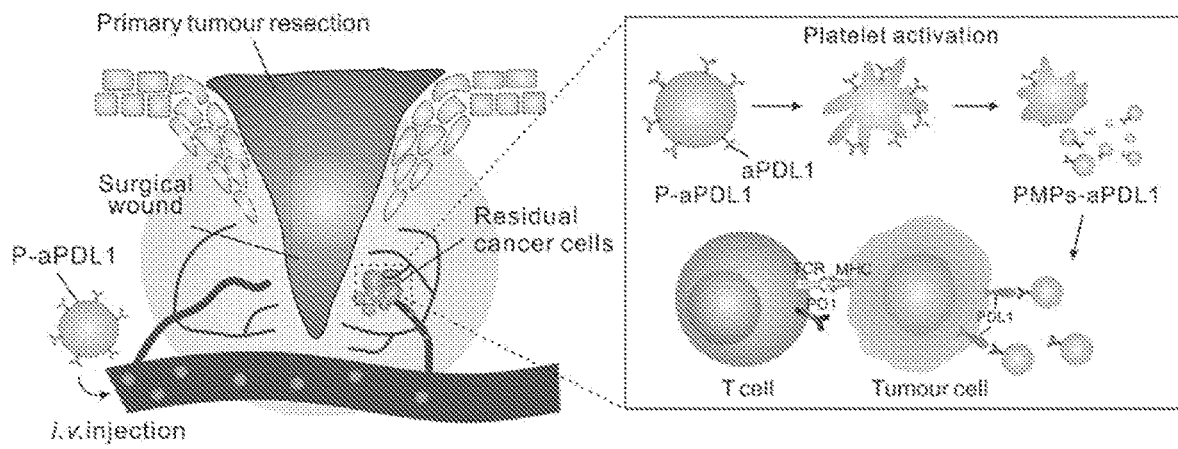
FIGS. 1A-1F. In situ activation of platelets with anti-PDL1 (P-aPDL1) promotes release of therapeutics.

The present disclosure provides platelet compositions and methods for the treatment and prevention of disease, for example, a cancer. In the compositions and methods disclosed herein, a therapeutic agent (for example, an immunotherapeutic agent) is covalently linked to a platelet cell. The inventors have found that an immunotherapeutic agent (for example, anti-PDL1) conjugated to the surface of a platelet cell reduces the recurrence of a cancer (and/or reduces metastasis) after resection of a primary tumor.

Reference will now be made in detail to the embodiments of the invention, examples of which are illustrated in the drawings and the examples. This invention may, however, be embodied in many different forms and should not be construed as limited to the embodiments set forth herein.

Unless defined otherwise, all technical and scientific terms used herein have the same meaning as commonly understood to one of ordinary skill in the art to which this disclosure belongs. The term "comprising" and variations thereof as used herein is used synonymously with the term "including" and variations thereof and are open, non-limiting terms. Although the terms "comprising" and "including" have been used herein to describe various embodiments, the terms "consisting essentially of" and "consisting of" can be used in place of "comprising" and "including" to provide for more specific embodiments and are also disclosed.

Terminology

As used in the specification and claims, the singular form "a," "an," and "the" include plural references unless the context clearly dictates otherwise. For example, the term "a cell" includes a plurality of cells, including mixtures thereof.

As used herein, the terms "may," "optionally," and "may optionally" are used interchangeably and are meant to include cases in which the condition occurs as well as cases in which the condition does not occur. Thus, for example, the statement that a formulation "may include an excipient" is meant to include cases in which the formulation includes an excipient as well as cases in which the formulation does not include an excipient.

As used here, the terms "beneficial agent" and "active agent" are used interchangeably herein to refer to a chemical compound or composition that has a beneficial biological effect. Beneficial biological effects include both therapeutic effects, i.e., treatment of a disorder or other undesirable physiological condition, and prophylactic effects, i.e., prevention of a disorder or other undesirable physiological condition (e.g., cancer). The terms also encompass pharmaceutically acceptable, pharmacologically active derivatives of beneficial agents specifically mentioned herein, including, but not limited to, salts, esters, amides, prodrugs, active metabolites, isomers, fragments, analogs, and the like. When the terms "beneficial agent" or "active agent" are used, then, or when a particular agent is specifically identified, it is to be understood that the term includes the agent per se as well as pharmaceutically acceptable, pharmacologically active salts, esters, amides, prodrugs, conjugates, active metabolites, isomers, fragments, analogs, etc.

As used herein, the terms "treating" or "treatment" of a subject includes the administration of a drug to a subject with the purpose of preventing, curing, healing, alleviating, relieving, altering, remedying, ameliorating, improving, stabilizing or affecting a disease or disorder, or a symptom of a disease or disorder. The terms "treating" and "treatment" can also refer to reduction in severity and/or frequency of symptoms, elimination of symptoms and/or underlying cause, prevention of the occurrence of symptoms and/or their underlying cause, and improvement or remediation of damage.

As used herein, the term "preventing" a disorder or unwanted physiological event in a subject refers specifically to the prevention of the occurrence of symptoms and/or their underlying cause, wherein the subject may or may not exhibit heightened susceptibility to the disorder or event.

By the term "effective amount" of a therapeutic agent is meant a nontoxic but sufficient amount of a beneficial agent to provide the desired effect. The amount of beneficial agent that is "effective" will vary from subject to subject, depending on the age and general condition of the subject, the particular beneficial agent or agents, and the like. Thus, it is not always possible to specify an exact "effective amount." However, an appropriate "effective" amount in any subject case may be determined by one of ordinary skill in the art using routine experimentation. Also, as used herein, and unless specifically stated otherwise, an "effective amount" of a beneficial can also refer to an amount covering both therapeutically effective amounts and prophylactically effective amounts.

An "effective amount" of a drug necessary to achieve a therapeutic effect may vary according to factors such as the age, sex, and weight of the subject. Dosage regimens can be adjusted to provide the optimum therapeutic response. For example, several divided doses may be administered daily or the dose may be proportionally reduced as indicated by the exigencies of the therapeutic situation.

As used herein, a "therapeutically effective amount" of a therapeutic agent refers to an amount that is effective to achieve a desired therapeutic result, and a "prophylactically effective amount" of a therapeutic agent refers to an amount that is effective to prevent an unwanted physiological condition. Therapeutically effective and prophylactically effective amounts of a given therapeutic agent will typically vary with respect to factors such as the type and severity of the disorder or disease being treated and the age, gender, and weight of the subject.

The term "therapeutically effective amount" can also refer to an amount of a therapeutic agent, or a rate of delivery of a therapeutic agent (e.g., amount over time), effective to facilitate a desired therapeutic effect. The precise desired therapeutic effect will vary according to the condition to be treated, the tolerance of the subject, the drug and/or drug formulation to be administered (e.g., the potency of the therapeutic agent (drug), the concentration of drug in the formulation, and the like), and a variety of other factors that are appreciated by those of ordinary skill in the art.

As used herein, the term "pharmaceutically acceptable" component can refer to a component that is not biologically or otherwise undesirable, i.e., the component may be incorporated into a pharmaceutical formulation of the invention and administered to a subject as described herein without causing any significant undesirable biological effects or interacting in a deleterious manner with any of the other components of the formulation in which it is contained. When the term "pharmaceutically acceptable" is used to refer to an excipient, it is generally implied that the component has met the required standards of toxicological and manufacturing testing or that it is included on the Inactive Ingredient Guide prepared by the U.S. Food and Drug Administration.

Also, as used herein, the term "pharmacologically active" (or simply "active"), as in a "pharmacologically active" derivative or analog, can refer to a derivative or analog (e.g., a salt, ester, amide, conjugate, metabolite, isomer, fragment, etc.) having the same type of pharmacological activity as the parent compound and approximately equivalent in degree.

As used herein, the term "mixture" can include solutions in which the components of the mixture are completely miscible, as well as suspensions and emulsions, in which the components of the mixture are not completely miscible.

As used herein, the term "subject" can refer to living organisms such as mammals, including, but not limited to humans, livestock, dogs, cats, and other mammals. Administration of the therapeutic agents can be carried out at dosages and for periods of time effective for treatment of a subject. In some embodiments, the subject is a human. In some embodiments, the pharmacokinetic profiles of the systems of the present invention are similar for male and female subjects.

The phrases "concurrent administration", "administration in combination", "simultaneous administration" or "administered simultaneously" as used herein, means that the compounds are administered at the same point in time or immediately following one another. In the latter case, the two compounds are administered at times sufficiently close that the results observed are indistinguishable from those achieved when the compounds are administered at the same point in time.

The term "antibody" or "antibodies" as used herein, refers to immunoglobulin molecules comprised of four polypeptide chains, two heavy (H) chains and two light (L) chains inter-connected by disulfide bonds. The term "antibody" or "antibodies" as used herein includes but is not limited to recombinant antibodies that are generated by recombinant technologies as known in the art. An "antibody" or "antibodies" can be of any origin including from mammalian species such as human, non-human primate (e.g. human such as from chimpanzee, baboon, rhesus or cynomolgus monkey), rodent (e.g. from mouse, rat, rabbit or guinea pig), goat, bovine or horse species; or of bird species such as chicken antibodies or of fish species such as shark antibodies. "Antibody" or "antibodies" include antibodies of any isotype, including human isotypes $IgA_1$ $IgA_2$, IgD, $IgG_1$, $IgG_{2a}$, $IgG_{2b}$, $IgG_3$, $IgG_4$, IgE and IgM and modified variants thereof. The antibody herein is directed against an "antigen" of interest. Preferably, the antigen is a biologically important polypeptide and administration of the antibody to a mammal suffering from a disease or disorder can result in a therapeutic benefit in that mammal. However, antibodies directed against non-polypeptide antigens are also contemplated.

The term "antibody fragment" or "antibody fragments" as used herein, refers to a naturally occurring antibody which lacks one or more domains or one or more amino acids. Typically, an antibody fragment contains the entire antigen binding or variable region thereof of such naturally occurring antibody. Examples of antibody fragments include any antibody that lacks the Fc portion. Examples of antibody fragments include also Fab, Fab', $F(ab')_2$, Fv and scFv fragments; diabodies; triabodies; tetrabodies; minibodies; antibodies consisting essentially of a single, two or three immunoglobulin domain(s) such as Domain Antibodies™; single-chain antibodies; bispecific, trispecific, tetraspecific or multispecific variants of any of the above.

Compositions

In one aspect, provided herein is a composition comprising:
  a platelet cell;
  a chemical linker moiety; and
  a therapeutic agent;
wherein the therapeutic agent is covalently linked to the platelet cell through the chemical linker moiety.

In one embodiment, the therapeutic agent is an immunotherapeutic agent. In one embodiment, the immunotherapeutic agent is selected from an anti-PDL1 antibody, an anti-PD1 antibody, an anti-CTLA4 antibody, an anti-CD47 antibody, or a combination thereof. In one embodiment, the immunotherapeutic agent is an anti-PDL1 antibody.

In one embodiment, the chemical linker moiety is selected from a maleimide linker, a PEG linker, PASylation, and HESylation. In one embodiment, the chemical linker moiety is a maleimide linker.

In one embodiment, the platelet cell is a human platelet cell. In one embodiment, the platelet cell is an autologous platelet cell.

In one embodiment, provided herein is a composition comprising:
- a platelet cell;
- a chemical linker moiety; and
- an immunotherapeutic agent;

wherein the immunotherapeutic agent is covalently linked to the platelet cell through the chemical linker moiety.

In one embodiment, provided herein is a composition comprising:
- a platelet cell;
- a chemical linker moiety; and
- an anti-PDL1 antibody;

wherein the anti-PDL1 antibody is covalently linked to the platelet cell through the chemical linker moiety.

In one embodiment, provided herein is a composition comprising:
- a platelet cell;
- a maleimide linker; and
- an immunotherapeutic agent;

wherein the immunotherapeutic agent is covalently linked to the platelet cell through the chemical linker moiety.

In one embodiment, provided herein is a composition comprising:
- a platelet cell;
- a maleimide linker; and
- an anti-PDL1 antibody;

wherein the anti-PDL1 antibody is covalently linked to the platelet cell through the chemical linker moiety.

Disclosed is a pharmaceutical composition containing therapeutically effective amounts of one or more of the disclosed platelet compositions and a pharmaceutically acceptable carrier. Pharmaceutical carriers suitable for administration of the compositions provided herein include any such carriers known to those skilled in the art to be suitable for the particular mode of administration. In addition, the compositions may be formulated as the sole pharmaceutically active ingredient in the pharmaceutical composition or may be combined with other active ingredients.

Compositions, as described herein, comprising an active compound (for example, an immunotherapeutic agent conjugated to a platelet cell) and an excipient of some sort may be useful in a variety of applications.

"Excipients" include any and all solvents, diluents or other liquid vehicles, dispersion or suspension aids, surface active agents, isotonic agents, thickening or emulsifying agents, preservatives, solid binders, lubricants and the like, as suited to the particular dosage form desired. General considerations in formulation and/or manufacture can be found, for example, in *Remington's Pharmaceutical Sciences*, Sixteenth Edition, E. W. Martin (Mack Publishing Co., Easton, Pa., 1980), and *Remington: The Science and Practice of Pharmacy*, 21st Edition (Lippincott Williams & Wilkins, 2005). The pharmaceutically acceptable excipients may also include one or more of fillers, binders, lubricants, glidants, disintegrants, and the like.

Exemplary excipients include, but are not limited to, any non-toxic, inert solid, semi-solid or liquid filler, diluent, encapsulating material or formulation auxiliary of any type. Some examples of materials which can serve as excipients include, but are not limited to, sugars such as lactose, glucose, and sucrose; starches such as corn starch and potato starch; cellulose and its derivatives such as sodium carboxymethyl cellulose, ethyl cellulose, and cellulose acetate; powdered tragacanth; malt; gelatin; talc; excipients such as cocoa butter and suppository waxes; oils such as peanut oil, cottonseed oil; safflower oil; sesame oil; olive oil; corn oil and soybean oil; glycols such as propylene glycol; esters such as ethyl oleate and ethyl laurate; agar; detergents such as Tween 80; buffering agents such as magnesium hydroxide and aluminum hydroxide; alginic acid; pyrogen-free water; isotonic saline; Ringer's solution; ethyl alcohol; and phosphate buffer solutions, as well as other non-toxic compatible lubricants such as sodium lauryl sulfate and magnesium stearate, as well as coloring agents, releasing agents, coating agents, sweetening, flavoring and perfuming agents, preservatives and antioxidants can also be present in the composition, according to the judgment of the formulator. As would be appreciated by one of skill in this art, the excipients may be chosen based on what the composition is useful for. For example, with a pharmaceutical composition, the choice of the excipient will depend on the route of administration, the agent being delivered, time course of delivery of the agent, etc., and can be administered to humans and/or to animals, orally, rectally, parenterally, intracisternally, intravaginally, intranasally, intraperitoneally, topically (as by powders, creams, ointments, or drops), bucally, or as an oral or nasal spray. In particular embodiments, the composition is injected at or near the resection site of a tumor.

Exemplary diluents include calcium carbonate, sodium carbonate, calcium phosphate, dicalcium phosphate, calcium sulfate, calcium hydrogen phosphate, sodium phosphate lactose, sucrose, cellulose, microcrystalline cellulose, kaolin, mannitol, sorbitol, inositol, sodium chloride, dry starch, cornstarch, powdered sugar, etc., and combinations thereof.

Exemplary granulating and/or dispersing agents include potato starch, corn starch, tapioca starch, sodium starch glycolate, clays, alginic acid, guar gum, citrus pulp, agar, bentonite, cellulose and wood products, natural sponge, cation-exchange resins, calcium carbonate, silicates, sodium carbonate, cross-linked poly(vinyl-pyrrolidone) (crospovidone), sodium carboxymethyl starch (sodium starch glycolate), carboxymethyl cellulose, cross-linked sodium carboxymethyl cellulose (croscarmellose), methylcellulose, pregelatinized starch (starch 1500), microcrystalline starch, water insoluble starch, calcium carboxymethyl cellulose, magnesium aluminum silicate (Veegum), sodium lauryl sulfate, quaternary ammonium compounds, etc., and combinations thereof.

Exemplary surface active agents and/or emulsifiers include natural emulsifiers (e.g. acacia, agar, alginic acid, sodium alginate, tragacanth, chondrux, cholesterol, xanthan, pectin, gelatin, egg yolk, casein, wool fat, cholesterol, wax, and lecithin), colloidal clays (e.g. bentonite [aluminum silicate] and Veegum [magnesium aluminum silicate]), long chain amino acid derivatives, high molecular weight alcohols (e.g. stearyl alcohol, cetyl alcohol, oleyl alcohol, triacetin monostearate, ethylene glycol distearate, glyceryl monostearate, and propylene glycol monostearate, polyvinyl alcohol), carbomers (e.g. carboxy polymethylene, polyacrylic acid, acrylic acid polymer, and carboxyvinyl polymer), carrageenan, cellulosic derivatives (e.g. carboxymethylcellulose sodium, powdered cellulose, hydroxymethyl cellulose, hydroxypropyl cellulose, hydroxypropyl methylcellulose, methylcellulose), sorbitan fatty acid esters (e.g. polyoxyethylene sorbitan monolaurate [Tween 20], polyoxyethylene sorbitan [Tween 60], polyoxyethylene sorbitan monooleate [Tween 80], sorbitan monopalmitate [Span 40], sorbitan monostearate [Span 60], sorbitan tristearate [Span 65], glyceryl monooleate, sorbitan monooleate [Span 80]), polyoxyethylene esters (e.g. polyoxyethylene monostearate

[Myrj 45], polyoxyethylene hydrogenated castor oil, polyethoxylated castor oil, polyoxymethylene stearate, and Solutol), sucrose fatty acid esters, polyethylene glycol fatty acid esters (e.g. Cremophor), polyoxyethylene ethers, (e.g. polyoxyethylene lauryl ether [Brij 30]), poly(vinyl-pyrrolidone), diethylene glycol monolaurate, triethanolamine oleate, sodium oleate, potassium oleate, ethyl oleate, oleic acid, ethyl laurate, sodium lauryl sulfate, Pluronic F 68, Poloxamer 188, cetrimonium bromide, cetylpyridinium chloride, benzalkonium chloride, docusate sodium, etc. and/or combinations thereof.

Exemplary binding agents include starch (e.g. cornstarch and starch paste), gelatin, sugars (e.g. sucrose, glucose, dextrose, dextrin, molasses, lactose, lactitol, mannitol, etc.), natural and synthetic gums (e.g. acacia, sodium alginate, extract of Irish moss, panwar gum, ghatti gum, mucilage of isapol husks, carboxymethylcellulose, methylcellulose, ethylcellulose, hydroxyethylcellulose, hydroxypropyl cellulose, hydroxypropyl methylcellulose, microcrystalline cellulose, cellulose acetate, poly(vinyl-pyrrolidone), magnesium aluminum silicate (Veegum), and larch arabogalactan), alginates, polyethylene oxide, polyethylene glycol, inorganic calcium salts, silicic acid, polymethacrylates, waxes, water, alcohol, etc., and/or combinations thereof.

Exemplary preservatives include antioxidants, chelating agents, antimicrobial preservatives, antifungal preservatives, alcohol preservatives, acidic preservatives, and other preservatives.

Exemplary antioxidants include alpha tocopherol, ascorbic acid, acorbyl palmitate, butylated hydroxyanisole, butylated hydroxytoluene, monothioglycerol, potassium metabisulfite, propionic acid, propyl gallate, sodium ascorbate, sodium bisulfite, sodium metabisulfite, and sodium sulfite.

Exemplary chelating agents include ethylenediaminetetraacetic acid (EDTA) and salts and hydrates thereof (e.g., sodium edetate, disodium edetate, trisodium edetate, calcium disodium edetate, dipotassium edetate, and the like), citric acid and salts and hydrates thereof (e.g., citric acid monohydrate), fumaric acid and salts and hydrates thereof, malic acid and salts and hydrates thereof, phosphoric acid and salts and hydrates thereof, and tartaric acid and salts and hydrates thereof. Exemplary antimicrobial preservatives include benzalkonium chloride, benzethonium chloride, benzyl alcohol, bronopol, cetrimide, cetylpyridinium chloride, chlorhexidine, chlorobutanol, chlorocresol, chloroxylenol, cresol, ethyl alcohol, glycerin, hexetidine, imidurea, phenol, phenoxyethanol, phenylethyl alcohol, phenylmercuric nitrate, propylene glycol, and thimerosal.

Exemplary antifungal preservatives include butyl paraben, methyl paraben, ethyl paraben, propyl paraben, benzoic acid, hydroxybenzoic acid, potassium benzoate, potassium sorbate, sodium benzoate, sodium propionate, and sorbic acid.

Exemplary alcohol preservatives include ethanol, polyethylene glycol, phenol, phenolic compounds, bisphenol, chlorobutanol, hydroxybenzoate, and phenylethyl alcohol.

Exemplary acidic preservatives include vitamin A, vitamin C, vitamin E, beta-carotene, citric acid, acetic acid, dehydroacetic acid, ascorbic acid, sorbic acid, and phytic acid.

Other preservatives include tocopherol, tocopherol acetate, deteroxime mesylate, cetrimide, butylated hydroxyanisol (BHA), butylated hydroxytoluened (BHT), ethylenediamine, sodium lauryl sulfate (SLS), sodium lauryl ether sulfate (SLES), sodium bisulfite, sodium metabisulfite, potassium sulfite, potassium metabisulfite, Glydant Plus, Phenonip, methylparaben, Germall 115, Germaben II, Neolone, Kathon, and Euxyl. In certain embodiments, the preservative is an anti-oxidant. In other embodiments, the preservative is a chelating agent.

Exemplary buffering agents include citrate buffer solutions, acetate buffer solutions, phosphate buffer solutions, ammonium chloride, calcium carbonate, calcium chloride, calcium citrate, calcium glubionate, calcium gluceptate, calcium gluconate, D-gluconic acid, calcium glycerophosphate, calcium lactate, propanoic acid, calcium levulinate, pentanoic acid, dibasic calcium phosphate, phosphoric acid, tribasic calcium phosphate, calcium hydroxide phosphate, potassium acetate, potassium chloride, potassium gluconate, potassium mixtures, dibasic potassium phosphate, monobasic potassium phosphate, potassium phosphate mixtures, sodium acetate, sodium bicarbonate, sodium chloride, sodium citrate, sodium lactate, dibasic sodium phosphate, monobasic sodium phosphate, sodium phosphate mixtures, tromethamine, magnesium hydroxide, aluminum hydroxide, alginic acid, pyrogen-free water, isotonic saline, Ringer's solution, ethyl alcohol, etc., and combinations thereof.

Exemplary lubricating agents include magnesium stearate, calcium stearate, stearic acid, silica, talc, malt, glyceryl behanate, hydrogenated vegetable oils, polyethylene glycol, sodium benzoate, sodium acetate, sodium chloride, leucine, magnesium lauryl sulfate, sodium lauryl sulfate, etc., and combinations thereof.

Exemplary natural oils include almond, apricot kernel, avocado, babassu, bergamot, black current seed, borage, cade, camomile, canola, caraway, carnauba, castor, cinnamon, cocoa butter, coconut, cod liver, coffee, corn, cotton seed, emu, eucalyptus, evening primrose, fish, flaxseed, geraniol, gourd, grape seed, hazel nut, hyssop, isopropyl myristate, jojoba, kukui nut, lavandin, lavender, lemon, litsea cubeba, macademia nut, mallow, mango seed, meadowfoam seed, mink, nutmeg, olive, orange, orange roughy, palm, palm kernel, peach kernel, peanut, poppy seed, pumpkin seed, rapeseed, rice bran, rosemary, safflower, sandalwood, sasquana, savoury, sea buckthorn, sesame, shea butter, silicone, soybean, sunflower, tea tree, thistle, tsubaki, vetiver, walnut, and wheat germ oils. Exemplary synthetic oils include, but are not limited to, butyl stearate, caprylic triglyceride, capric triglyceride, cyclomethicone, diethyl sebacate, dimethicone 360, isopropyl myristate, mineral oil, octyldodecanol, oleyl alcohol, silicone oil, and combinations thereof.

Additionally, the composition may further comprise a polymer. Exemplary polymers contemplated herein include, but are not limited to, cellulosic polymers and copolymers, for example, cellulose ethers such as methylcellulose (MC), hydroxyethylcellulose (HEC), hydroxypropyl cellulose (HPC), hydroxypropyl methyl cellulose (HPMC), methylhydroxyethylcellulose (MHEC), methylhydroxypropyl cellulose (MHPC), carboxymethyl cellulose (CMC) and its various salts, including, e.g., the sodium salt, hydroxyethylcarboxymethylcellulose (HECMC) and its various salts, carboxymethylhydroxyethylcellulose (CMHEC) and its various salts, other polysaccharides and polysaccharide derivatives such as starch, dextran, dextran derivatives, chitosan, and alginic acid and its various salts, carageenan, various gums, including xanthan gum, guar gum, gum arabic, gum karaya, gum ghatti, konjac and gum tragacanth, glycosaminoglycans and proteoglycans such as hyaluronic acid and its salts, proteins such as gelatin, collagen, albumin, and fibrin, other polymers, for example, polyhydroxyacids such as polylactide, polyglycolide, polyl(lactide-co-glycolide) and poly(.epsilon.-caprolactone-co-glycolide)-, carboxyvinyl polymers and their salts (e.g., carbomer), polyvinylpyrrolidone (PVP), polyacrylic acid and its salts, polyacrylamide, polyacilic acid/acrylamide copolymer, polyalkylene oxides such as polyethylene oxide, polypropylene oxide, poly(ethylene oxide-propylene oxide), and a Pluronic polymer, polyoxyethylene (polyethylene glycol), polyanhydrides, polyvinylalchol, polyethyleneamine and polypyrridine, polyethylene glycol (PEG) polymers, such as PEGylated lipids (e.g., PEG-stearate, 1,2-Distearoyl-sn-glycero-3-Phosphoethanolamine-N-[Methoxy(Polyethylene glycol)-1000], 1,2-Distearoyl-sn-glycero-3-Phosphoethanolamine-N-[Methoxy(Polyethylene glycol)-2000], and 1,2-Distearoyl-sn-glycero-3-Phosphoethanolamine-N-[Methoxy(Polyethylene glycol)-5000]), copolymers and salts thereof.

Additionally, the composition may further comprise an emulsifying agent. Exemplary emulsifying agents include, but are not limited to, a polyethylene glycol (PEG), a polypropylene glycol, a polyvinyl alcohol, a poly-N-vinyl pyrrolidone and copolymers thereof, poloxamer nonionic surfactants, neutral water-soluble polysaccharides (e.g., dextran, Ficoll, celluloses), non-cationic poly(meth)acrylates, non-cationic polyacrylates, such as poly(meth)acrylic acid, and esters amide and hydroxyalkyl amides thereof, natural emulsifiers (e.g. acacia, agar, alginic acid, sodium alginate, tragacanth, chondrux, cholesterol, xanthan, pectin, gelatin, egg yolk, casein, wool fat, cholesterol, wax, and lecithin), colloidal clays (e.g. bentonite [aluminum silicate] and Veegum [magnesium aluminum silicate]), long chain amino acid derivatives, high molecular weight alcohols (e.g. stearyl alcohol, cetyl alcohol, oleyl alcohol, triacetin monostearate, ethylene glycol distearate, glyceryl monostearate, and propylene glycol monostearate, polyvinyl alcohol), carbomers (e.g. carboxy polymethylene, polyacrylic acid, acrylic acid polymer, and carboxyvinyl polymer), carrageenan, cellulosic derivatives (e.g. carboxymethylcellulose sodium, powdered cellulose, hydroxymethyl cellulose, hydroxypropyl cellulose, hydroxypropyl methylcellulose, methylcellulose), sorbitan fatty acid esters (e.g. polyoxyethylene sorbitan monolaurate [Tween 20], polyoxyethylene sorbitan [Tween 60], polyoxyethylene sorbitan monooleate [Tween 80], sorbitan monopalmitate [Span 40], sorbitan monostearate [Span 60], sorbitan tristearate [Span 65], glyceryl monooleate, sorbitan monooleate [ Span 80]), polyoxyethylene esters (e.g. polyoxyethylene monostearate [Myrj 45], polyoxyethylene hydrogenated castor oil, polyethoxylated castor oil, polyoxymethylene stearate, and Solutol), sucrose fatty acid esters, polyethylene glycol fatty acid esters (e.g. Cremophor), polyoxyethylene ethers, (e.g. polyoxyethylene lauryl ether [Brij 30]), poly(vinyl-pyrrolidone), diethylene glycol monolaurate, triethanolamine oleate, sodium oleate, potassium oleate, ethyl oleate, oleic acid, ethyl laurate, sodium lauryl sulfate, Pluronic F 68, Poloxamer 188, cetrimonium bromide, cetylpyridinium chloride, benzalkonium chloride, docusate sodium, etc. and/or combinations thereof. In certain embodiments, the emulsifying agent is cholesterol.

Liquid compositions include emulsions, microemulsions, solutions, suspensions, syrups, and elixirs. In addition to the active compound (for example, an immunotherapeutic agent conjugated to a platelet cell) (immunotherapeutic agent conjugated to a platelet cell), the liquid composition may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

Injectable compositions, for example, injectable aqueous or oleaginous suspensions may be formulated according to the known art using suitable dispersing or wetting agents and suspending agents. The sterile injectable preparation may also be an injectable solution, suspension, or emulsion in a nontoxic parenterally acceptable diluent or solvent, for example, as a solution in 1,3-butanediol. Among the acceptable vehicles and solvents for pharmaceutical or cosmetic compositions that may be employed are water, Ringer's solution, U.S.P. and isotonic sodium chloride solution. In addition, sterile, fixed oils are conventionally employed as a solvent or suspending medium. Any bland fixed oil can be employed including synthetic mono- or diglycerides. In addition, fatty acids such as oleic acid are used in the preparation of injectables. In certain embodiments, the particles are suspended in a carrier fluid comprising 1% (w/v) sodium carboxymethyl cellulose and 0.1% (v/v) Tween 80. The injectable composition can be sterilized, for example, by filtration through a bacteria-retaining filter, or by incorporating sterilizing agents in the form of sterile solid compositions which can be dissolved or dispersed in sterile water or other sterile injectable medium prior to use.

In some embodiments, the compositions or the therapeutic agents (for example, an additional therapeutic agent given in combination with the compositions disclosed herein) can be administered in a solid composition. Solid compositions include capsules, tablets, pills, powders, and granules. In such solid compositions, the particles are mixed with at least one excipient and/or a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets, and pills, the dosage form may also comprise buffering agents. Solid compositions of a similar type may also be employed as fillers in soft and hard-filled gelatin capsules using such excipients as lactose or milk sugar as well as high molecular weight polyethylene glycols and the like.

Tablets, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract, optionally, in a delayed manner. Examples of embedding compositions which can be used include polymeric substances and waxes.

Solid compositions of a similar type may also be employed as fillers in soft and hard-filled gelatin capsules using such excipients as lactose or milk sugar as well as high molecular weight polyethylene glycols and the like.

Compositions for topical or transdermal administration include ointments, pastes, creams, lotions, gels, powders, solutions, sprays, inhalants, or patches. The active compound (for example, an immunotherapeutic agent conjugated to a platelet cell) is admixed with an excipient and any needed preservatives or buffers as may be required.

The ointments, pastes, creams, and gels may contain, in addition to the active compound (for example, an immunotherapeutic agent conjugated to a platelet cell), excipients such as animal and vegetable fats, oils, waxes, paraffins, starch, tragacanth, cellulose derivatives, polyethylene glycols, silicones, bentonites, silicic acid, talc, and zinc oxide, or mixtures thereof.

Powders and sprays can contain, in addition to the active compound/composition, excipients such as lactose, talc, silicic acid, aluminum hydroxide, calcium silicates, and polyamide powder, or mixtures of these substances. Sprays can additionally contain customary propellants such as chlorofluorohydrocarbons.

Transdermal patches have the added advantage of providing controlled delivery of a compound to the body. Such dosage forms can be made by dissolving or dispensing the nanoparticles in a proper medium. Absorption enhancers can also be used to increase the flux of the compound across the skin. The rate can be controlled by either providing a rate controlling membrane or by dispersing the particles in a polymer matrix or gel.

In some embodiments, the therapeutic agent can be encapsulated in a nanoparticle. In one embodiment, provided herein is a composition comprising:
 a platelet cell;
 a chemical linker moiety; and
 a therapeutic agent;
wherein the therapeutic agent is encapsulated within a nanoparticle.

In some embodiments, the nanoparticle is linked covalently through the chemical linker moiety. In some embodiments, the chemical linker moiety is optional and the nanoparticles are not covalently linked to the platelet cell.

The nanoparticles can be made from one or more polymers. In some examples, the polymer includes copolymers of polycarboxylic acids or salts thereof, carboxylic anhydrides (for example, maleic anhydride) with other monomers (for example, methyl (meth)acrylate, acrylic acid and the like), hydrophilic vinyl polymers, such as polyvinyl acetate, polyvinyl alcohol, polyvinyl pyrrolidone (PVP), polyethyleneoxide (PEO), poly(vinyl pyrrolidone-co-vinyl acetate), polymethacrylates, polyoxyethylene alkyl ethers, polyoxyethylene castor oils, polycaprolactam, polylactic acid, polyglycolic acid, poly(lactic-glycolic) acid, poly(lactic co-glycolic) acid (PLGA), cellulose derivatives, such as hydroxymethylcellulose, hydroxypropylcellulose and the like. In one example, the polymer is 50:50 PLGA copolymer. In other examples, the polymer includes a natural polymer, such as chitosan, collagen, alginate, gelatin, hyaluronic acid, and nontoxic metal salts thereof. In some embodiments, the polymer is a hydrogel, for example an alginate hydrogel. Hydrophilic polymers and other vehicles can be used alone or in combination, and enhanced structural integrity can be imparted to the vehicle by partial crystallization, ionic bonding, cross-linking and the like.

Methods of encapsulating drugs or therapeutic agents into particles are known in the art. Common encapsulation techniques include, but are not limited to, spray drying, interfacial polymerization, hot melt encapsulation, phase separation encapsulation (spontaneous emulsion microencapsulation, solvent evaporation microencapsulation, and solvent removal microencapsulation), coacervation, low temperature microsphere formation, and phase inversion nanoencapsulation (PIN). A brief summary of these methods is presented below.

In certain embodiments, the nanoparticles incorporated in the compositions discussed herein are multi-walled nanoparticles. Multi-walled nanoparticles useful in the compositions disclosed herein can be prepared, for example, using "sequential phase inversion nanoencapsulation" (sPIN).

1. Spray Drying

Methods for forming microspheres/nanospheres using spray drying techniques are described in U.S. Pat. No. 6,620,617, to Mathiowitz et al. In this method, the polymer is dissolved in an organic solvent such as methylene chloride or in water. A known amount of one or more active agents to be incorporated in the particles is suspended (in the case of an insoluble active agent) or co-dissolved (in the case of a soluble active agent) in the polymer solution. The solution or dispersion is pumped through a micronizing nozzle driven by a flow of compressed gas, and the resulting aerosol is suspended in a heated cyclone of air, allowing the solvent to evaporate from the microdroplets, forming particles. Microspheres/nanospheres ranging between 0.1-10 microns can be obtained using this method.

2. Interfacial Polymerization

Interfacial polymerization can also be used to encapsulate one or more active agents. Using this method, a monomer and the active agent(s) are dissolved in a solvent. A second monomer is dissolved in a second solvent (typically aqueous) which is immiscible with the first. An emulsion is formed by suspending the first solution through stirring in the second solution. Once the emulsion is stabilized, an initiator is added to the aqueous phase causing interfacial polymerization at the interface of each droplet of emulsion.

3. Hot Melt Micro Encapsulation

Microspheres can be formed from polymers such as polyesters and polyanhydrides using hot melt microencapsulation methods as described in Mathiowitz et al., Reactive Polymers, 6:275 (1987). In this method, the use of polymers with molecular weights between 3-75,000 daltons is preferred. In this method, the polymer first is melted and then mixed with the solid particles of one or more active agents to be incorporated that have been sieved to less than 50 microns. The mixture is suspended in a non-miscible solvent (like silicon oil), and, with continuous stirring, heated to 5° C. above the melting point of the polymer. Once the emulsion is stabilized, it is cooled until the polymer particles solidify. The resulting microspheres are washed by decanting with petroleum ether to give a free-flowing powder.

4. Phase Separation Microencapsulation

In phase separation microencapsulation techniques, a polymer solution is stirred, optionally in the presence of one or more active agents to be encapsulated. While continuing to uniformly suspend the material through stirring, a non-solvent for the polymer is slowly added to the solution to decrease the polymer's solubility. Depending on the solubility of the polymer in the solvent and nonsolvent, the polymer either precipitates or phase separates into a polymer rich and a polymer poor phase. Under proper conditions, the polymer in the polymer rich phase will migrate to the interface with the continuous phase, encapsulating the active agent(s) in a droplet with an outer polymer shell.

in. Spontaneous Emulsion Microencapsulation

Spontaneous emulsification involves solidifying emulsified liquid polymer droplets formed above by changing temperature, evaporating solvent, or adding chemical cross-linking agents. The physical and chemical properties of the encapsulant, as well as the properties of the one or more active agents optionally incorporated into the nascent particles, dictates suitable methods of encapsulation. Factors such as hydrophobicity, molecular weight, chemical stability, and thermal stability affect encapsulation.

ii. Solvent Evaporation Microencapsulation

Methods for forming microspheres using solvent evaporation techniques are described in E. Mathiowitz et al., J. Scanning Microscopy, 4:329 (1990); L. R. Beck et al., Fertil. Steril., 31:545 (1979); L. R. Beck et al Am J Obstet Gynecol 135(3) (1979); S. Benita et al., J. Pharm. Sci., 73:1721 (1984); and U.S. Pat. No. 3,960,757 to Morishita et al. The polymer is dissolved in a volatile organic solvent, such as methylene chloride. One or more active agents to be incorporated are optionally added to the solution, and the mixture is suspended in an aqueous solution that contains a surface active agent such as poly(vinyl alcohol). The resulting emulsion is stirred until most of the organic solvent evaporated, leaving solid microspheres/nanospheres. This method is useful for relatively stable polymers, such as polyesters and polystyrene. However, labile polymers, such as polyanhydrides, may degrade during the fabrication process due to the presence of water. For these polymers, some of the following methods performed in completely anhydrous organic solvents are more useful.

iii. Solvent Removal Microencapsulation

The solvent removal microencapsulation technique is primarily designed for polyanhydrides and is described, for example, in WO 93/21906 to Brown University Research Foundation. In this method, the substance to be incorporated is dispersed or dissolved in a solution of the selected polymer in a volatile organic solvent, such as methylene chloride. This mixture is suspended by stirring in an organic oil, such as silicon oil, to form an emulsion. Microspheres that range between 1-300 microns can be obtained by this procedure. Substances which can be incorporated in the microspheres include pharmaceuticals, pesticides, nutrients, imaging agents, and metal compounds.

5. Coacervation

Encapsulation procedures for various substances using coacervation techniques are known in the art, for example, in GB-B-929 406; GB-B-929 40 1; and U.S. Pat. Nos. 3,266,987, 4,794,000, and 4,460,563. Coacervation involves the separation of a macromolecular solution into two immiscible liquid phases. One phase is a dense coacervate phase, which contains a high concentration of the polymer encapsulant (and optionally one or more active agents), while the second phase contains a low concentration of the polymer. Within the dense coacervate phase, the polymer encapsulant forms nanoscale or microscale droplets. Coacervation may be induced by a temperature change, addition of a non-solvent or addition of a micro-salt (simple coacervation), or by the addition of another polymer thereby forming an interpolymer complex (complex coacervation).

6. Low Temperature Casting of Microspheres

Methods for very low temperature casting of controlled release microspheres are described in U.S. Pat. No. 5,019, 400 to Gombotz et al. In this method, a polymer is dissolved in a solvent optionally with one or more dissolved or dispersed active agents. The mixture is then atomized into a vessel containing a liquid non-solvent at a temperature below the freezing point of the polymer-substance solution which freezes the polymer droplets. As the droplets and non-solvent for the polymer are warmed, the solvent in the droplets thaws and is extracted into the non-solvent, resulting in the hardening of the microspheres.

7. Phase Inversion Nanoencapsulation (PIN)

Nanoparticles can also be formed using the phase inversion nanoencapsulation (PIN) method, wherein a polymer is dissolved in a "good" solvent, fine particles of a substance to be incorporated, such as a drug, are mixed or dissolved in the polymer solution, and the mixture is poured into a strong non-solvent for the polymer, to spontaneously produce, under favorable conditions, polymeric microspheres, wherein the polymer is either coated with the particles or the particles are dispersed in the polymer. See, e.g., U.S. Pat. No. 6,143,211 to Mathiowitz, et al. The method can be used to produce monodisperse populations of nanoparticles and microparticles in a wide range of sizes, including, for example, about 100 nanometers to about 10 microns.

Advantageously, an emulsion need not be formed prior to precipitation. The process can be used to form microspheres from thermoplastic polymers.

8. Sequential Phase Inversion Nanoencapsulation (sPIN)

Multi-walled nanoparticles can also be formed by a process referred to herein as "sequential phase inversion nanoencapsulation" (sPIN). sPIN is particularly suited for forming monodisperse populations of nanoparticles, avoiding the need for an additional separations step to achieve a monodisperse population of nanoparticles.

In sPIN, a core polymer is dissolved in a first solvent. The active agent is dissolved or dispersed in a core polymer solvent. The core polymer, core polymer solvent, and agent to be encapsulated form a mixture having a continuous phase, in which the core polymer solvent is the continuous phase. The shell polymer is dissolved in a shell polymer solvent, which is a non-solvent for the core polymer. The solutions of the core polymer and shell polymer are mixed together. The resulting decreases the solubility of the core polymer at its cloud point due to the presence of the shell polymer solvent results in the preferential phase separation of the core polymer and, optionally, encapsulation of the agent. When a non-solvent for the core polymer and the shell polymer is added to this unstable mixture, the shell polymer engulfs the core polymer as phase inversion is completed to form a double-walled nanoparticle.

sPIN provides a one-step procedure for the preparation of multi-walled particles, such as double-walled nanoparticles, which is nearly instantaneous, and does not require emulsification of the solvent. Methods for forming multi-walled particles are disclosed in U.S. Publication No. 2012-0009267 to Cho, et al. The disclosure of which is incorporated herein by reference.

The particle can be a dendrimer particle. Dendrimers are three-dimensional polymers that are grown by the successive addition of shells or layers of branched molecules to a central core. Dendrimers have several advantages over linear polymers, since they have controllable structure, a single molecular weight rather than a distribution of molecular weights, and a large number of controllable surface functionalities, and an inclination to adopt a globular conformation once a certain size is reached. They are prepared by reacting highly branched monomers together to produce monodisperse, tree-like and/or generational structure polymeric structures. Individual dendrimers consist of a central core molecule, with a dendritic wedge attached to each functional site. The dendrimeric surface layer can have a variety of functional groups disposed thereon, according to the assembly monomers used during the preparation. Generally, the dendrimer functional groups dictate the properties of the individual dendrimer types. As a result of their design, dendrimer cores are spacious, and by modifying the chemical properties of the core, shells, and especially the surface layer, their physical properties can be finely tuned. Tunable properties include solubility, toxicity, immunogenicity and bioattachment capability.

Polyamidoamine, polypropyleneimine, polyarylether and polyethyleneimine are examples of dendrimers that have been investigated for biopharmaceutical applications. Polyamidoamine dendrimers are based on an ethylenediamine core and an amidoamine repeat branching structure. They can be synthesized in a variety of well-defined molecular weights. Their size and surface functionality (primary amine) is defined by the number of controlled repetitive additions of monomeric units, giving rise to different half or full generations. They are water-soluble and they have been reported to be the only class of dendrimer that are monodispersed. Furthermore, they show high charge densities that are restricted to the surface of the molecules.

Dendrimers have been used as carriers for therapeutic compounds, either by entrapment of a drug in cavities within the dendrimer, or by covalently linking drug molecules to the surface. This is reviewed in Svenson, S., Eur J Pharm Biopharm (2009) 71:445-462 and Cheng, Y., J. Pharm. Sci. (2007) 97:123-143. Entrapment within dendrimer cavities is limited to small molecules, and covalent attachment approaches have thus far been limited to systems in which a small drug is hydrolytically or enzymatically cleaved from the dendrimer surface.

Methods

In one aspect, disclosed herein is a method of preventing metastasis or recurrence of a cancer, comprising:
administering to a subject in need thereof a therapeutically effective amount of a composition comprising:
  a platelet cell;
  a chemical linker moiety; and
  a therapeutic agent;
wherein the therapeutic agent is covalently linked to the platelet cell through the chemical linker moiety.

In one embodiment, the therapeutic agent is an immunotherapeutic agent. In one embodiment, the immunotherapeutic agent is selected from an anti-PDL1 antibody, an anti-PD1 antibody, an anti-CTLA4 antibody, an anti-CD47 antibody, or a combination thereof. In one embodiment, the immunotherapeutic agent is an anti-PDL1 antibody.

In one embodiment, the chemical linker moiety is selected from a maleimide linker, a PEG linker, PASylation, and HESylation. In one embodiment, the chemical linker moiety is a maleimide linker.

In one embodiment, the platelet cell is a human platelet cell. In one embodiment, the platelet cell is an autologous platelet cell.

In one embodiment, the cancer is a solid tumor. In one embodiment, the cancer is melanoma. In one embodiment, the cancer is breast cancer. In one embodiment, the composition is administered in combination with an additional therapeutic agent. In one embodiment, the additional therapeutic agent is an antineoplastic agent.

In one aspect, disclosed herein is a method of treating or preventing a cancer, comprising:
administering to a subject in need thereof a therapeutically effective amount of a composition comprising:
  a platelet cell;
  a chemical linker moiety; and
  a therapeutic agent;
wherein the therapeutic agent is covalently linked to the platelet cell through the chemical linker moiety.

In a further aspect, disclosed herein is a method for the targeted delivery of a therapeutic agent comprising:
administering to a subject a composition comprising:
  a platelet cell;
  a chemical linker moiety; and
  a therapeutic agent;
wherein the therapeutic agent is covalently linked to the platelet cell through the chemical linker moiety;
wherein the composition is targeted to a wound or surgical resection site through activation of the platelet cell.

In one embodiment, the method provides the therapeutic agent is further released in platelet-derived microparticles at the wound or resection site upon activation of the platelet cell.

In one embodiment, the therapeutic agent is an immunotherapeutic agent. In one embodiment, the immunotherapeutic agent is selected from an anti-PDL1 antibody, an anti-PD1 antibody, an anti-CTLA4 antibody, an anti-CD47 antibody, or a combination thereof. In one embodiment, the immunotherapeutic agent is an anti-PDL1 antibody.

In one embodiment, the chemical linker moiety is selected from a maleimide linker, a PEG linker, PASylation, and HESylation. In one embodiment, the chemical linker moiety is a maleimide linker.

In one embodiment, the platelet cell is a human platelet cell. In one embodiment, the platelet cell is an autologous platelet cell.

Cancers and Solid Tumors

In some embodiments, the platelet compositions and methods described herein are useful for treating or preventing metastasis or recurrence of a cancer. In some embodiments, the platelet compositions and methods described herein are useful for the prevention of recurrence of excised solid tumors. In some embodiments, the compositions and methods described herein are useful for the prevention of metastasis of excised solid tumors. In another embodiment, the cancer recurrence to be prevented is melanoma. In another embodiment, the cancer recurrence to be prevented is breast cancer. In a further embodiment, the cancer recurrence to be prevented is prostate cancer.

In one aspect, the methods described herein are used to prevent solid tumor recurrence or metastasis, for example, melanoma, lung cancer (including lung adenocarcinoma, basal cell carcinoma, squamous cell carcinoma, large cell carcinoma, bronchioloalveolar carcinoma, bronchogenic carcinoma, non-small-cell carcinoma, small cell carcinoma, mesothelioma); breast cancer (including ductal carcinoma, lobular carcinoma, inflammatory breast cancer, clear cell carcinoma, mucinous carcinoma, serosal cavities breast carcinoma); colorectal cancer (colon cancer, rectal cancer, colorectal adenocarcinoma); anal cancer; pancreatic cancer (including pancreatic adenocarcinoma, islet cell carcinoma, neuroendocrine tumors); prostate cancer; prostate adenocarcinoma; ovarian carcinoma (ovarian epithelial carcinoma or surface epithelial-stromal tumor including serous tumor, endometrioid tumor and mucinous cystadenocarcinoma, sex-cord-stromal tumor); liver and bile duct carcinoma (including hepatocellular carcinoma, cholangiocarcinoma, hemangioma); esophageal carcinoma (including esophageal adenocarcinoma and squamous cell carcinoma); oral and oropharyngeal squamous cell carcinoma; salivary gland adenoid cystic carcinoma; bladder cancer; bladder carcinoma; carcinoma of the uterus (including endometrial adenocarcinoma, ocular, uterine papillary serous carcinoma, uterine clear-cell carcinoma, uterine sarcomas, leiomyosarcomas, mixed mullerian tumors); glioma, glioblastoma, medulloblastoma, and other tumors of the brain; kidney cancers (including renal cell carcinoma, clear cell carcinoma, Wilm's tumor); cancer of the head and neck (including squamous cell carcinomas); cancer of the stomach (gastric cancers, stomach adenocarcinoma, gastrointestinal stromal tumor); testicular cancer; germ cell tumor; neuroendocrine tumor; cervical cancer; carcinoids of the gastrointestinal tract, breast, and other organs; signet ring cell carcinoma; mesenchymal tumors including sarcomas, fibrosarcomas, haemangioma, angiomatosis, haemangiopericytoma, pseudoangiomatous stromal hyperplasia, myofibroblastoma, fibromatosis, inflammatory myofibroblastic tumor, lipoma, angiolipoma, granular cell tumor, neurofibroma, schwannoma, angiosarcoma, liposarcoma, rhabdomyosarcoma, osteosarcoma, leiomyoma, leiomyosarcoma, skin, including melanoma, cervical, retinoblastoma, head and neck cancer, pancreatic, brain, thyroid, testicular, renal, bladder, soft tissue, adenal gland, urethra, cancers of the penis, myxosarcoma, chondrosarcoma, osteosarcoma, chordoma, malignant fibrous histiocytoma, lymphangiosarcoma, mesothelioma, squamous cell carcinoma; epidermoid carcinoma, malignant skin adnexal tumors, adenocarcinoma, hepatoma, hepatocellular carcinoma, renal cell carcinoma, hypernephroma, cholangiocarcinoma, transitional cell carcinoma, choriocarcinoma, seminoma, embryonal cell carcinoma, glioma anaplastic; glioblastoma multiforme, neuroblastoma, medulloblastoma, malignant meningioma, malignant schwannoma, neurofibrosarcoma, parathyroid carcinoma, medullary carcinoma of thyroid, bronchial carcinoid, pheochromocytoma, Islet cell carcinoma, malignant carcinoid, malignant paraganglioma, melanoma, Merkel cell neoplasm, cystosarcoma phylloide, salivary cancers, thymic carcinomas, and cancers of the vagina among others.

In some embodiments, the platelet compositions and methods described herein are useful in treating or preventing a cancer. In some cases, the cancer is a circulating cancer cell (circulating tumor cell). In some cases, the cancer is a metastatic cancer cell.

In some embodiments, the platelet compositions described herein can eliminate or reduce the circulating tumor cells (CTCs) in vivo. In some embodiments, the platelet compositions described herein can significantly inhibit the tumor metastasis. In some embodiments, the platelet compositions described herein can significantly inhibit the recurrence of a cancer (for example, after resection of a solid tumor).

Platelets

Platelets are anucleated cellular fragments released from megakaryocytes and are best known for their function in hemostasis. The average life span of circulating platelets is 8 to 9 days, which could greatly improve pharmacokinetics of intravenously injected therapeutics. Moreover, transfused platelets could migrate to the site of surgical wounds, where residual tumors may survive after the surgery. On the other side, evidence has shown that the platelets have the capability to recognize and interact with circulating tumor cells (CTCs), which have shed into the vasculature from the primary tumor and led to metastasis. Beside their intrinsic wounds and CTCs tropic properties, platelets can also be considered as immune "cells" that initiate and improve many inflammatory conditions.

In some cases, the platelet composition is autologous, i.e., produced from a platelet obtained from the subject. In some cases, the platelet composition is heterologous, i.e., produced from a platelet obtained from a source other than the subject being treated.

In some embodiments, the whole platelet cell can be conjugated to the therapeutic agent. In some embodiments, the therapeutic agent can be delivered in platelet-derived microparticles. Platelet-derived microparticles (PMPS) are derived from the plasma membrane upon platelet activation; activated platelets release PMPs carrying adhesion molecules and chemokines, facilitating monocyte trap at the site of PMP deposition. These PMPs are released from the platelets following activation of the platelets (for example, by thrombin).

Therapeutic Agents

In one embodiment, the therapeutic agent to be conjugated to the platelet via a linker can be selected from the group consisting of a peptide, polypeptide, protein, antibody, antibody fragment, nucleic acid or a therapeutic drug (for example, a small molecule).

In one embodiment, the therapeutic agent is an immunotherapeutic agent. In one embodiment, the therapeutic agent is an antibody or an antibody fragment. In some embodiments, the therapeutic agent is an anti-neoplastic agent. In some embodiments, the platelet compositions can target delivery of a therapeutic agent for treating vascular disease.

Immunotherapeutic Agents

In one embodiment, the immunotherapeutic agent is selected from an anti-PDL1 antibody, an anti-PD1 antibody, an anti-CTLA4 antibody, an anti-CD47 antibody, or a combination thereof.

In one embodiment, the immunotherapeutic agent is an anti-PDL1 antibody. In one embodiment, the anti-PDL1 antibody is selected from atezolizumab, durvalumab, or avelumab. In one embodiment, the anti-PDL1 antibody is atezolizumab (MPDL3280A)(Roche). In one embodiment, the anti-PDL1 antibody is durvalumab (MEDI4736). In one embodiment, the anti-PDL1 antibody is avelumab (MS0010718C).

In one embodiment, the immunotherapeutic agent is a programmed death protein 1 (PD-1) inhibitor or programmed death protein ligand 1 or 2 inhibitor. PD-1 inhibitors are known in the art, and include, for example, nivolumab (BMS), pembrolizumab (Merck), pidilizumab (CureTech/Teva), AMP-244 (Amplimmune/GSK), BMS-936559 (BMS), and MEDI4736 (Roche/Genentech).

In one embodiment, the immunotherapeutic agent is an anti-PD1 antibody. In one embodiment, the anti-PD1 antibody is nivolumab. In one embodiment, the anti-PD1 antibody is pembrolizumab.

In one embodiment, the immunotherapeutic agent is an anti-CTLA4 antibody. In one embodiment, the anti-CTLA4 antibody is ipilimumab.

In some embodiments, the immunotherapeutic agent is administered in combination with an additional therapeutic agent. In some embodiments, the immunotherapeutic agent is administered in combination with an anti-neoplastic agent.

Anti-Neoplastic Agents

In some embodiments, the therapeutic agent is an anti-neoplastic agent. For example, the anti-neoplastic agent can be selected from the group consisting of Abiraterone Acetate, Abitrexate (Methotrexate), Abraxane (Paclitaxel Albumin-stabilized Nanoparticle Formulation), ABVD, ABVE, ABVE-PC, AC, AC-T, Adcetris (Brentuximab Vedotin), ADE, Ado-Trastuzumab Emtansine, Adriamycin (Doxorubicin Hydrochloride), Adrucil (Fluorouracil), Afatinib Dimaleate, Afinitor (Everolimus), Akynzeo (Netupitant and Palonosetron Hydrochloride), Aldara (Imiquimod), Aldesleukin, Alemtuzumab, Alimta (Pemetrexed Disodium), Aloxi (Palonosetron Hydrochloride), Ambochlorin (Chlorambucil), Amboclorin (Chlorambucil), Aminolevulinic Acid, Anastrozole, Aprepitant, Aredia (Pamidronate Disodium), Arimidex (Anastrozole), Aromasin (Exemestane), Arranon (Nelarabine), Arsenic Trioxide, Arzerra (Ofatumumab), Asparaginase Erwinia chrysanthemi, Avastin (Bevacizumab), Axitinib, Azacitidine, BEACOPP, Becenum (Carmustine), Beleodaq (Belinostat), Belinostat, Bendamustine Hydrochloride, BEP, Bevacizumab, Bexarotene, Bexxar (Tositumomab and Iodine I 131 Tositumomab), Bicalutamide, BiCNU (Carmustine), Bleomycin, Blinatumomab, Blincyto (Blinatumomab), Bortezomib, Bosulif (Bosutinib), Bosutinib, Brentuximab Vedotin, Busulfan, Busulfex (Busulfan), Cabazitaxel, Cabozantinib-S-Malate, CAF, Campath (Alemtuzumab), Camptosar (Irinotecan Hydrochloride), Capecitabine, CAPOX, Carboplatin, CARBOPLATIN-TAXOL, Carfilzomib, Carmubris (Carmustine), Carmustine, Carmustine Implant, Casodex (Bicalutamide), CeeNU (Lomustine), Ceritinib, Cerubidine (Daunorubicin Hydrochloride), Cervarix (Recombinant HPV Bivalent Vaccine), Cetuximab, Chlorambucil, CHLORAMBUCIL-PREDNISONE, CHOP, Cisplatin, Clafen (Cyclophosphamide), Clofarabine, Clofarex (Clofarabine), Clolar (Clofarabine), CMF, Cometriq (Cabozantinib-S-Malate), COPP, COPP-ABV, Cosmegen (Dactinomycin), Crizotinib, CVP, Cyclophosphamide, Cyfos (Ifosfamide), Cyramza (Ramucirumab), Cytarabine, Cytarabine, Liposomal, Cytosar-U (Cytarabine), Cytoxan (Cyclophosphamide), Dabrafenib, Dacarbazine, Dacogen (Decitabine), Dactinomycin, Dasatinib, Daunorubicin Hydrochloride, Decitabine, Degarelix, Denileukin Diftitox, Denosumab, DepoCyt (Liposomal Cytarabine), DepoFoam (Liposomal Cytarabine), Dexrazoxane Hydrochloride, Dinutuximab, Docetaxel, Doxil (Doxorubicin Hydrochloride Liposome), Doxorubicin Hydrochloride, Doxorubicin Hydrochloride Liposome, Dox-SL (Doxorubicin Hydrochloride Liposome), DTIC-Dome (Dacarbazine), Efudex (Fluorouracil), Elitek (Rasburicase), Ellence (Epirubicin Hydrochloride), Eloxatin (Oxaliplatin), Eltrombopag Olamine, Emend (Aprepitant), Enzalutamide, Epirubicin Hydrochloride, EPOCH, Erbitux (Cetuximab), Eribulin Mesylate, Erivedge (Vismodegib), Erlotinib Hydrochloride, Erwinaze (Asparaginase Erwinia chrysanthemi), Etopophos (Etoposide Phosphate), Etoposide, Etoposide Phosphate, Evacet (Doxorubicin Hydrochloride Liposome), Everolimus, Evista (Raloxifene Hydrochloride), Exemestane, Fareston (Toremifene), Farydak (Panobinostat), Faslodex (Fulvestrant), FEC, Femara (Letrozole), Filgrastim, Fludara (Fludarabine Phosphate), Fludarabine Phosphate, Fluoroplex (Fluorouracil), Fluorouracil, Folex (Methotrexate), Folex PFS (Methotrexate), FOLFIRI, FOLFIRI-BEVACIZUMAB, FOLFIRI-CETUXIMAB, FOLFIRINOX, FOLFOX, Folotyn (Pralatrexate), FU-LV, Fulvestrant, Gardasil (Recombinant HPV Quadrivalent Vaccine), Gardasil 9 (Recombinant HPV Nonavalent Vaccine), Gazyva (Obinutuzumab), Gefitinib, Gemcitabine Hydrochloride, GEMCITABINE-CISPLATIN, GEMCITABINE-OXALIPLATIN, Gemtuzumab Ozogamicin, Gemzar (Gemcitabine Hydrochloride), Gilotrif (Afatinib Dimaleate), Gleevec (Imatinib Mesylate), Gliadel (Carmustine Implant), Gliadel wafer (Carmustine Implant), Glucarpidase, Goserelin Acetate, Halaven (Eribulin Mesylate), Herceptin (Trastuzumab), HPV Bivalent Vaccine, Recombinant, HPV Nonavalent Vaccine, Recombinant, HPV Quadrivalent Vaccine, Recombinant, Hycamtin (Topotecan Hydrochloride), Hyper-CVAD, Ibrance (Palbociclib), Ibritumomab Tiuxetan, Ibrutinib, ICE, Iclusig (Ponatinib Hydrochloride), Idamycin (Idarubicin Hydrochloride), Idarubicin Hydrochloride, Idelalisib, Ifex (Ifosfamide), Ifosfamide, Ifosfamidum (Ifosfamide), Imatinib Mesylate, Imbruvica (Ibrutinib), Imiquimod, Inlyta (Axitinib), Interferon Alfa-2b, Recombinant, Intron A (Recombinant Interferon Alfa-2b), Iodine I 131 Tositumomab and Tositumomab, Ipilimumab, Iressa (Gefitinib), Irinotecan Hydrochloride, Istodax (Romidepsin), Ixabepilone, Ixempra (Ixabepilone), Jakafi (Ruxolitinib Phosphate), Jevtana (Cabazitaxel), Kadcyla (Ado-Trastuzumab Emtansine), Keoxifene (Raloxifene Hydrochloride), Kepivance (Palifermin), Keytruda (Pembrolizumab), Kyprolis (Carfilzomib), Lanreotide Acetate, Lapatinib Ditosylate, Lenalidomide, Lenvatinib Mesylate, Lenvima (Lenvatinib Mesylate), Letrozole, Leucovorin Calcium, Leukeran (Chlorambucil), Leuprolide Acetate, Levulan (Aminolevulinic Acid), Linfolizin (Chlorambucil), LipoDox (Doxorubicin Hydrochloride Liposome), Liposomal Cytarabine, Lomustine, Lupron (Leuprolide Acetate), Lupron Depot (Leuprolide Acetate), Lupron Depot-Ped (Leuprolide Acetate), Lupron Depot-3 Month (Leuprolide Acetate), Lupron Depot-4 Month (Leuprolide Acetate), Lynparza (Olaparib), Marqibo (Vincristine Sulfate Liposome), Matulane (Procarbazine Hydrochloride), Mechlorethamine Hydrochloride, Megace (Megestrol Acetate), Megestrol Acetate, Mekinist (Trametinib), Mercaptopurine, Mesna, Mesnex (Mesna), Methazolastone (Temozolomide), Methotrexate, Methotrexate LPF (Methotrexate), Mexate (Methotrexate), Mexate-AQ (Methotrexate), Mitomycin C, Mitoxantrone Hydrochloride, Mitozytrex (Mitomycin C), MOPP, Mozobil (Plerixafor), Mustargen (Mechlorethamine Hydrochloride), Mutamycin (Mitomycin C), Myleran (Busulfan), Mylosar (Azacitidine), Mylotarg (Gemtuzumab Ozogamicin), Nanoparticle Paclitaxel (Paclitaxel Albumin-stabilized Nanoparticle Formulation), Navelbine (Vinorelbine Tartrate), Nelarabine, Neosar (Cyclophosphamide), Netupitant and Palonosetron Hydrochloride, Neupogen (Filgrastim), Nexavar (Sorafenib Tosylate), Nilotinib, Nivolumab, Nolvadex (Tamoxifen Citrate), Nplate (Romiplostim), Obinutuzumab, Odomzo (Sonidegib), OEPA, Ofatumumab, OFF, Olaparib, Omacetaxine Mepesuccinate, Oncaspar (Pegaspargase), Ondansetron Hydrochloride, Ontak (Denileukin Diftitox), Opdivo (Nivolumab), OPPA, Oxaliplatin, Paclitaxel, Paclitaxel Albumin-stabilized Nanoparticle Formulation, PAD, Palbociclib, Palifermin, Palonosetron Hydrochloride, Palonosetron Hydrochloride and Netupitant, Pamidronate Disodium, Panitumumab, Panobinostat, Paraplat (Carboplatin), Paraplatin (Carboplatin), Pazopanib Hydrochloride, Pegaspargase, Peginterferon Alfa-2b, PEG-Intron (Peginterferon Alfa-2b), Pembrolizumab, Pemetrexed Disodium, Pen eta (Pertuzumab), Pertuzumab, Platinol (Cisplatin), Platinol-AQ (Cisplatin), Plerixafor, Pomalidomide, Pomalyst (Pomalidomide), Ponatinib Hydrochloride, Pralatrexate, Prednisone, Procarbazine Hydrochloride, Proleukin (Aldesleukin), Prolia (Denosumab), Promacta (Eltrombopag Olamine), Provenge (Sipuleucel-T), Purinethol (Mercaptopurine), Purixan (Mercaptopurine), Radium 223 Dichloride, Raloxifene Hydrochloride, Ramucirumab, Rasburicase, R-CHOP, R-CVP, Recombinant Human Papillomavirus (HPV) Bivalent Vaccine, Recombinant Human Papillomavirus (HPV) Nonavalent Vaccine, Recombinant Human Papillomavirus (HPV) Quadrivalent Vaccine, Recombinant Interferon Alfa-2b, Regorafenib, R-EPOCH, Revlimid (Lenalidomide), Rheumatrex (Methotrexate), Rituxan (Rituximab), Rituximab, Romidepsin, Romiplostim, Rubidomycin (Daunorubicin Hydrochloride), Ruxolitinib Phosphate, Sclerosol Intrapleural Aerosol (Talc), Siltuximab, Sipuleucel-T, Somatuline Depot (Lanreotide Acetate), Sonidegib, Sorafenib Tosylate, Sprycel (Dasatinib), STANFORD V, Sterile Talc Powder (Talc), Steritalc (Talc), Stivarga (Regorafenib), Sunitinib Malate, Sutent (Sunitinib Malate), Sylatron (Peginterferon Alfa-2b), Sylvant (Siltuximab), Synovir (Thalidomide), Synribo (Omacetaxine Mepesuccinate), TAC, Tafinlar (Dabrafenib), Talc, Tamoxifen Citrate, Tarabine PFS (Cytarabine), Tarceva (Erlotinib Hydrochloride), Targretin (Bexarotene), Tasigna (Nilotinib), Taxol (Paclitaxel), Taxotere (Docetaxel), Temodar (Temozolomide), Temozolomide, Temsirolimus, Thalidomide, Thalomid (Thalidomide), Thiotepa, Toposar (Etoposide), Topotecan Hydrochloride, Toremifene, Torisel (Temsirolimus), Tositumomab and Iodine I 131 Tositumomab, Totect (Dexrazoxane Hydrochloride), TPF, Trametinib, Trastuzumab, Treanda (Bendamustine Hydrochloride), Trisenox (Arsenic Trioxide), Tykerb (Lapatinib Ditosylate), Unituxin (Dinutuximab), Vandetanib, VAMP, Vectibix (Panitumumab), VeIP, Velban (Vinblastine Sulfate), Velcade (Bortezomib), Velsar (Vinblastine Sulfate), Vemurafenib, VePesid (Etoposide), Viadur (Leuprolide Acetate), Vidaza (Azacitidine), Vinblastine Sulfate, Vincasar PFS (Vincristine Sulfate), Vincristine Sulfate, Vincristine Sulfate Liposome, Vinorelbine Tartrate, VIP, Vismodegib, Voraxaze (Glucarpidase), Vorinostat, Votrient (Pazopanib Hydrochloride), Wellcovorin (Leucovorin Calcium), Xalkori (Crizotinib), Xeloda (Capecitabine), XELIRI, XELOX, Xgeva (Denosumab), Xofigo (Radium 223 Dichloride), Xtandi (Enzalutamide), Yervoy (Ipilimumab), Zaltrap (Ziv-Aflibercept), Zelboraf (Vemurafenib), Zevalin (Ibritumomab Tiuxetan), Zinecard (Dexrazoxane Hydrochloride), Ziv-Aflibercept, Zofran (Ondansetron Hydrochloride), Zoladex (Goserelin Acetate), Zoledronic Acid, Zolinza (Vorinostat), Zometa (Zoledronic Acid), Zydelig (Idelalisib), Zykadia (Ceritinib), and Zytiga (Abiraterone Acetate).

Methods for Treating Vascular Disease

Since platelets also play a key role in several physiologic and pathologic processes such as hemostasis and thrombosis by forming the plugs that seal injured vessels and arrest bleeding, this platform can also be used to treat relevant vascular diseases.

Disclosed herein is a method for treating vascular disease in a subject that involves administering to the subject a platelet composition disclosed herein. In these embodiments, the platelet delivers a drug to treat vascular disease, e.g., coagulation disorders or coronary restenosis. For example, the drug can be heparin or doxorubicin.

In one aspect, provided herein is a method of treating or preventing vascular disease, comprising:
administering to a subject in need thereof a therapeutically effective amount of a composition comprising:
- a platelet cell;
- a chemical linker moiety; and
- a therapeutic agent;

wherein the therapeutic agent is covalently linked to the platelet cell through the chemical linker moiety.

In one embodiment, the chemical linker moiety is selected from a maleimide linker, a PEG linker, PASylation, and HESylation. In one embodiment, the chemical linker moiety is a maleimide linker.

In one embodiment, the platelet cell is a human platelet cell. In one embodiment, the platelet cell is an autologous platelet cell.

In one embodiment, the vascular disease is tissue injury, inflammation, or cardiovascular disease. In one embodiment, the composition is administered in combination with an additional therapeutic agent.

In some embodiments, the platelet compositions can target delivery of a therapeutic agent for treating or preventing vascular disease, e.g., coagulation disorders or coronary restenosis.

For example, in some cases, the therapeutic agent can be selected from the group consisting of Adcirca (tadalafil), Adempas (riociguat), Agrylin (anagrelide HCL), Angiomax (bivalirudin), Atacand (candesartan cilexetil), Atryn (antithrombin recombinant lyophilized powder for reconstitution), Azor (amlodipine besylate; olmesartan medoxomil), Baycol (cerivastatin sodium), BiDil (isosorbide dinitrate/hydralazine hydrochloride), Brilinta (ticagrelor), Caduet (amlodipine/atorvastatin), Captopril, Cardizem (R) (Diltiazem HCl for injection) Monvial (R), CellCept, Cleviprex (clevidipine), Corlanor (ivabradine), Corlopam, Corvert Injection (ibutilide fumarate injection), Covera-HS (verapamil), Crestor (rosuvastatin calcium), Diltiazem HCL, Diovan (valsartan), Doxorubicin, DynaCirc CR, Edarbi (azilsartan medoxomil), Edarbyclor (azilsartan medoxomil and chlorthalidone), Efient (prasugrel), Eliquis (apixaban), Entresto (sacubitril and valsartan), Epanova (omega-3-carboxylic acids), Fenofibrate, Heparin, Innohep (tinzaparin sodium) injectable, Integrilin, Juxtapid (lomitapide), Kengreal (cangrelor), Kynamro (mipomersen sodium), Lescol (fluvastatin sodium), Lescol (fluvastatin sodium) capsules, Rx, Letairis (ambrisentan), Levitra (vardenafil), Lexxel (enalapril maleate-felodipine ER), Lipitor (atorvastatin calcium), Liptruzet (ezetimibe and atorvastatin), Livalo (pitavastatin), Mavik (trandolapril), Micardis (telmisartan), Micardis HCT (telmisartan and hydrochlorothiazide), Microzide (hydrochlorothiazide), Multaq (dronedarone), Natrecor (nesiritide), Niaspan, Normiflo, Nymalize (nimodipine), Opsumit (macitentan), Pentoxifylline, Pindolol, Plavix (clopidogrel bisulfate), Plavix (clopidogrel bisulfate), Posicor, Pradaxa (dabigatran etexilate mesylate), Pravachol (pravastatin sodium), Pravachol (pravastatin sodium), Prestalia (perindopril arginine and amlodipine besylate), Prinivil or Zestril (Lisinopril), ProAmatine (midodrine), Ranexa (ranolazine), Remodulin (treprostinil), ReoPro, REPRONEX(menotropins for injection, USP), Retavase (reteplase), Rythmol, Savaysa (edoxaban), Soliris (eculizumab), Teczem (enalapril maleate/diltiazem malate), Tekamlo (aliskiren+amlodipine), Tekturna (aliskiren), Teveten (eprosartan mesylate plus hydrochlorothiazide), Teveten (eprosartan mesylate), Tiazac (diltiazem hydrochloride), Tiazac (diltiazem hydrochloride), Tiazac (diltiazem hydrochloride), Toprol-XL (metoprolol succinate), Tribenzor (olmesartan medoxomil+amlodipine+hydrochlorothiazide), Tricor (fenofibrate), Trilipix (fenofibric acid), Tyvaso (treprostinil), Varithena (polidocanol injectable foam), Vascepa (icosapent ethyl), Visipaque (iodixanol), Xarelto (rivaroxaban), Xarelto (rivaroxaban), Zocor, Zontivity (vorapaxar).

Linkers

A covalent approach can be employed to modify platelets via a chemical linker. One of the benefits of using a chemical linker is that it bypasses the need for genetic changes. Such a bifunctional chemical linker can link the therapeutic agent to the platelet cell. Examples of bifunctional linker groups include, but are not limited to, moieties such as sugars, amino acids, amino alcohols, carboxy alcohols, amino thiols, and the like.

In some embodiments, the chemical linker moiety is selected from a maleimide linker, a PEG linker, PASylation, and HESylation. In one embodiment, the chemical linker moiety is a maleimide linker.

EXAMPLES

The following examples are set forth below to illustrate the compositions, methods, and results according to the disclosed subject matter. These examples are not intended to be inclusive of all aspects of the subject matter disclosed herein, but rather to illustrate representative methods and results. These examples are not intended to exclude equivalents and variations of the present invention which are apparent to one skilled in the art.

Example 1

In Situ Activation of Platelets with Checkpoint Inhibitors for Post-Surgical Cancer Immunotherapy Surgery is the main treatment option for most solid tumors. Despite continual improvements in surgical techniques, residual microtumors and/or CTCs after tumor resection remain challenging[1-3]. Additionally, it has also been suggested that surgery can induce the promotion of cancer metastasis[4, 5]. Many patients develop recurrent disease post-surgery, which can lead to significant morbidity as well as mortality. Hence, there has been tremendous interest in developing effective strategies to prevent cancer recurrence after surgery. Among them, cancer immunotherapy has received considerable attention recently[6]. Immunotherapeutic agents do not directly attack the tumor, but boost the body's immune system to kill the cancer cells[7]. The immune checkpoint blockade has elicited durable antitumor responses and long-term remissions in a subset of patients[8-10]. Particularly, the checkpoint inhibitors block the interaction with programmed cell death protein 1 (PD1) on lymphocytes and programmed cell death 1 ligand 1 (PDL1) on antigen presenting cells (APCs) and tumor cells have shown exciting results in treating various types of cancer[11-14]. Moreover, the first PD-L1 inhibitor, atezolizumab, has been granted accelerated approval by U.S. Food and Drug Administration (FDA) recently[15]. Despite remarkable progress, current methods of checkpoint blockade therapy limit the therapeutic benefits in many patients. The largest limitation observed in clinical trials may be the severity of the side effects, such as autoimmune disorders[16-18]. Grade ¾ adverse events have sometimes occurred when treated with immune checkpoint blockade therapy[15, 19]. Meanwhile, a large fraction of patients failed to respond to these agents[8, 10, 15]. The objective response rate of anti-PD therapy still needs improvement. How to enhance anti-PD therapy has become one of the central themes in the field of cancer immunology and immunotherapy[6, 11].

One mechanism that may account for the compromised treatment efficacy of anti-PD therapy is the off-target antibodies to normal tissues when intravenously infused[16, 18, 20, 21]. In this context, it is desirable for future cancer immunotherapies to specifically focus on the tumor site rather than systemic activation of the immune system[20]. Moreover, the limited efficacy may also be due to the insufficient tumor lymphocytic infiltration and T cell-inflamed tumor microenvironment, which contains a higher expression of PDL1 that is positively associated with clinical benefit from anti-PD therapy[22-25].

Cell-based systems have recently emerged as biological drug carriers, including erythrocytes, bacterial ghosts, and genetically engineered stem and immune cells.[26, 27] Among them, platelets are anucleated cellular fragments released from megakaryocytes and are best known for their function in hemostasis[28-31]. The average life span of circulating platelets is 8 to 9 days[27, 32], which could greatly improve the pharmacokinetics of intravenously injected therapeutics. Moreover, transfused platelets could migrate to the site of surgical wounds[33], where residual tumors may survive after surgery. On the other side, emerging evidence has shown that the platelets have the capability to recognize and interact with CTCs[34-36], which have shed into the vasculature from the primary tumor and led to metastasis. With the help of platelets, aPDL1 can be targeted to the cancer cells after surgery, while reducing off-target effects of therapeutics. Beside their intrinsic wounds and CTCs tropic properties, platelets are also considered as immune "cells" that initiate and improve many inflammatory conditions[37-39]. Platelet-derived chemokines recruit and awaken T cells as well as other immune cells. As the major source of soluble CD40L (sCD40L), platelets can boost T cell immunity and are necessary to induce dendritic cell (DCs) maturation and B-cell isotype switching for production of immunoglobulin G[40]. It has also been reported that PDL1 and PDL2 are upregulated in response to inflammation,[41, 42] which results in PDL1-positive tumors, making the tumor more sensitive to anti-PD therapy and improving the ORR potentially.

In this example, anti-PDL1 (aPDL1) was loaded to the surface of platelets for preventing post-surgical tumor recurrence (FIG. 1a). Surprisingly, the inventors found that the binding of aPDL1 to unactivated platelets was highly stable, while release of aPDL1 could be significantly promoted upon the activation of platelets. Thus, the aPDL1 release can result from the platelet-derived microparticles (PMPs), which are generated from the plasma membrane of activated platelets[43]. Such a structural alteration can facilitate aPDL1 binging to APC and tumor cells. By intravenous injection of aPDL1 conjugated platelets (P-aPD1) to the B16 melanoma and 4T1 mammary carcinoma tumor bearing mice after resection of the primary tumor, it was demonstrated that the platelets can help aPDL1 transport and accumulate toward the surgical bed with the residual microtumors, as well as the CTCs in the blood. The T cell-inflamed tumor microenvironment was also created by platelets upon activation, together with the increased PDL1 expression on tumor site. Meanwhile, aPDL1 can be released after platelet activation to block the PDL1 on immune and tumor cells. These results show that platelets can serve as carriers for a therapeutic agent (for example, aPDL1) delivery in a targeted and controlled release manner to prevent cancer recurrence after surgery.

Engineering Platelets Decorated with aPDL1

Figure 6:
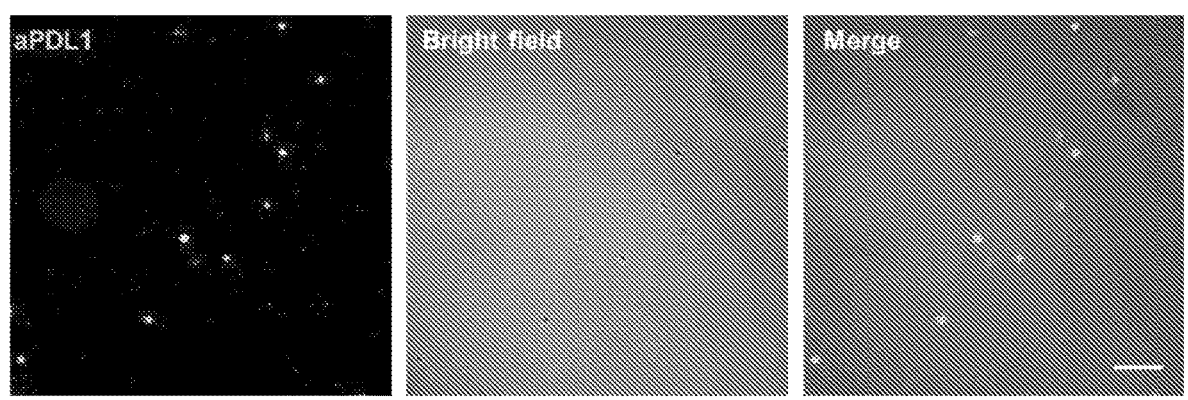
FIG. 6. Confocal immunofluorescence images of the aPDL1-coupled platelets. FITC-conjugated secondary antibody was used to detect image aPDL1 on platelet. Scale bar, 20 µm.
Figure 7:
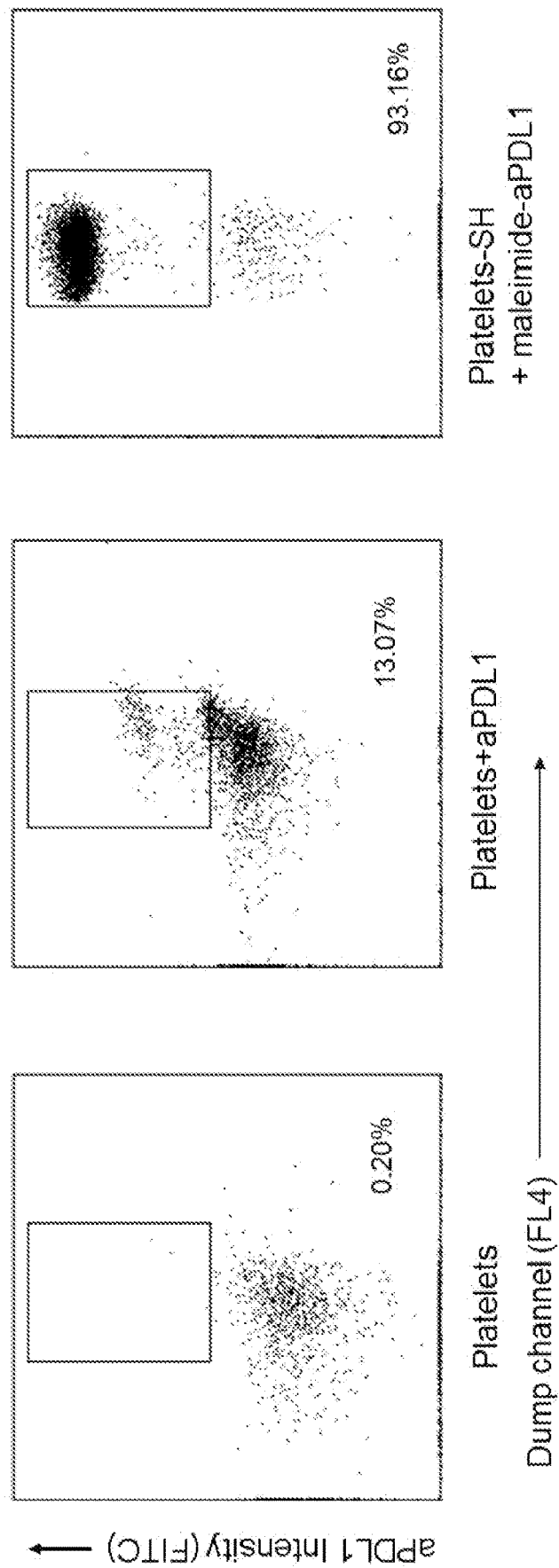
FIG. 7. Flow cytometry assay of aPDL1-coupled platelets. Platelets were incubated with aPDL1 under different experimental settings and analyzed by flow cytometry using the goat anti-rat IgG (H+L) secondary antibody, FITC. The successful attachment of aPDL1 on the surface of the platelet was verified via the sulfydryl and maleimide binding.
Figure 8A:
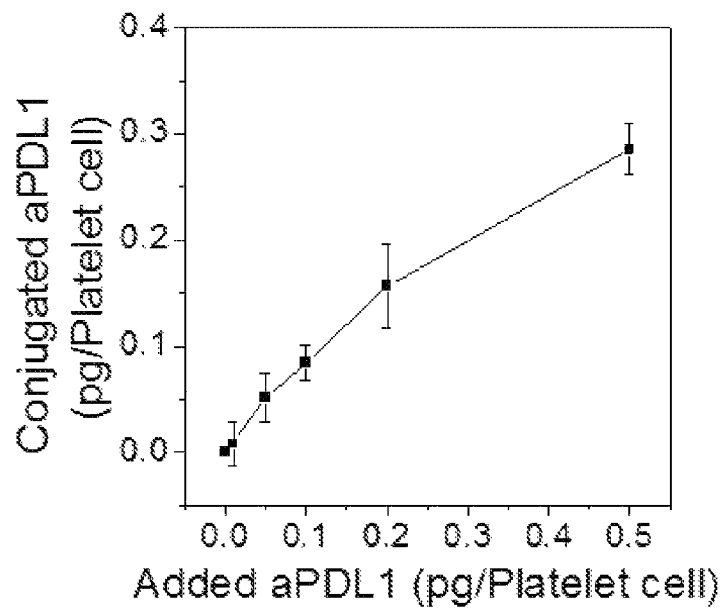
FIGS. 8A-8C. Conjugation and stability of aPDL1-coupled platelets.
Figure 8B:
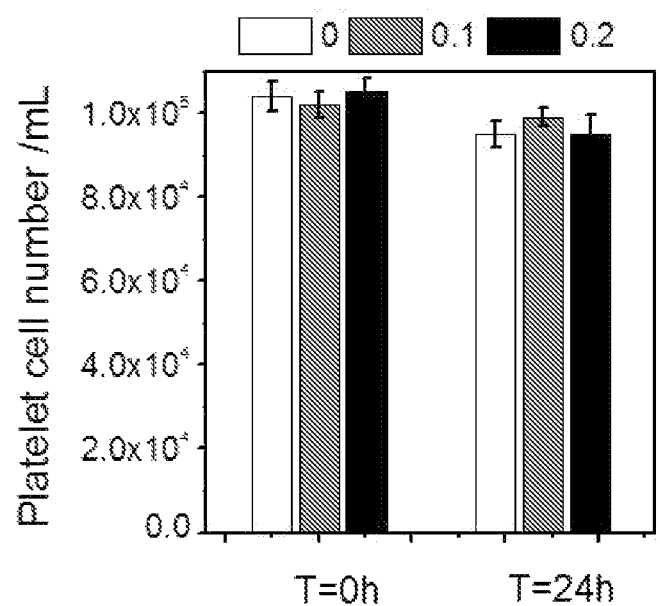
Figure 8C:
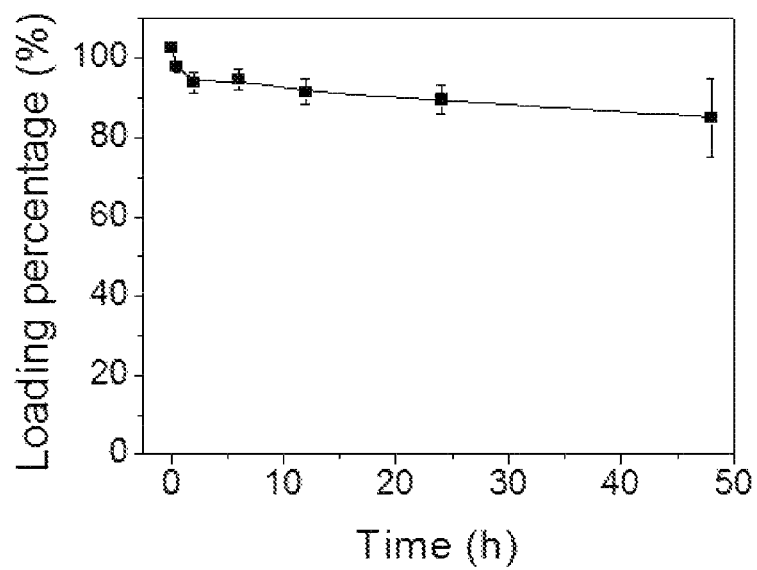
Figure 9:
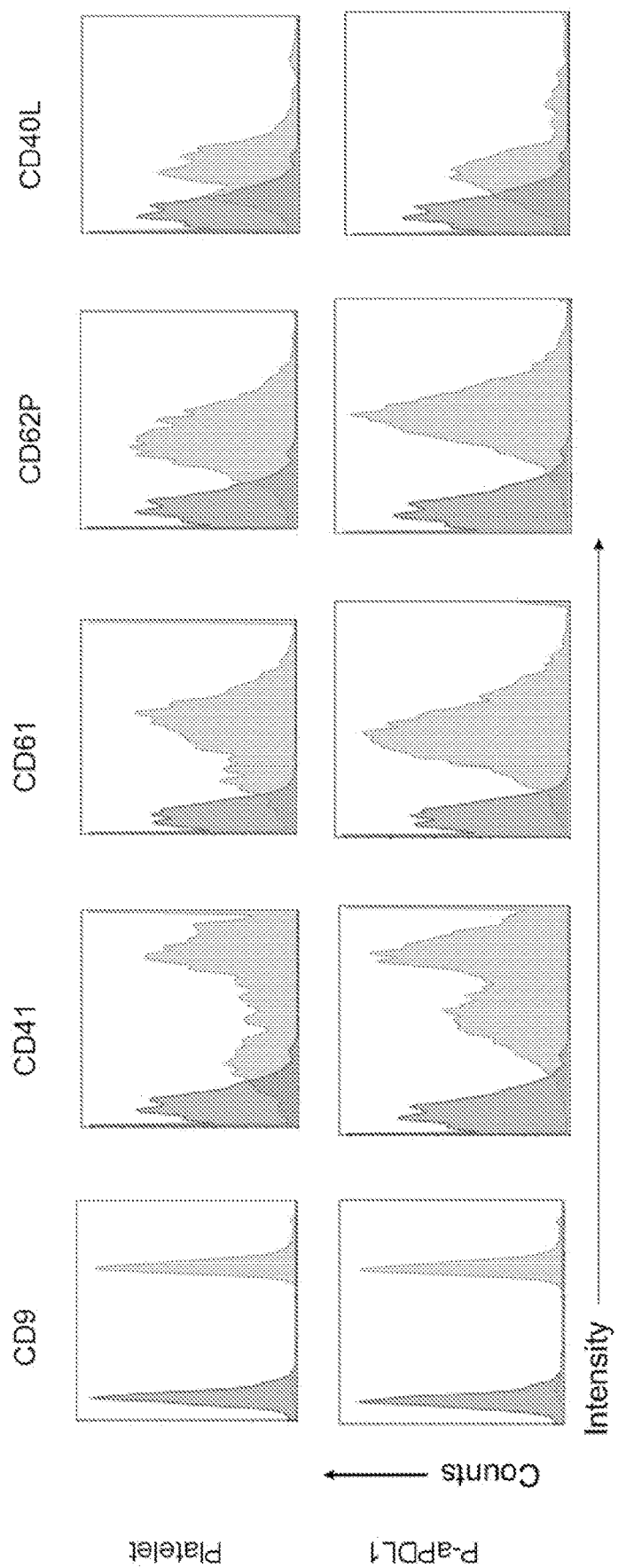
FIG. 9. Surface protein expression on naïve and aPDL1 conjugated platelets (CD62P and CD40L were examined after activation).

A covalent approach was employed to modify platelets with aPDL1 conveniently via a bifunctional maleimide linker, which bypasses the need for genetic modification[44]. The binding of aPDL1 to platelets was examined by immunofluorescence (FIG. 6). Additionally, the maleimide-free aPDL1 showed minimal nonspecific binding to the platelets (FIG. 7). The enzyme-linked immunosorbent assay (ELISA) showed that platelets could be readily coupled with aPDL1 up to ~0.3 pg per platelet (FIG. 8a). It was also found that coupling 0.1 and 0.2 pg of aPDL1 per platelet had no significant effect on their viability (FIG. 8b). Such covalent binding was highly stable, and did not show significant release within two days (FIG. 8c). Moreover, several surface proteins of platelets, which modulate cell adhesion and migration, were examined (FIG. 9). Collectively, the conjugation with aPDL1 did not induce significant damage to those platelet cells.

Activation of Platelets Promotes Release of Therapeutics

Figure 1B:
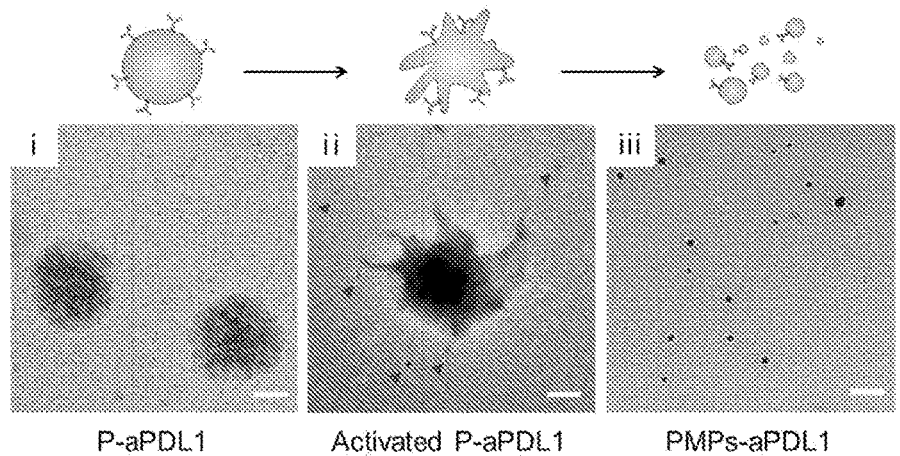
Figure 1C:
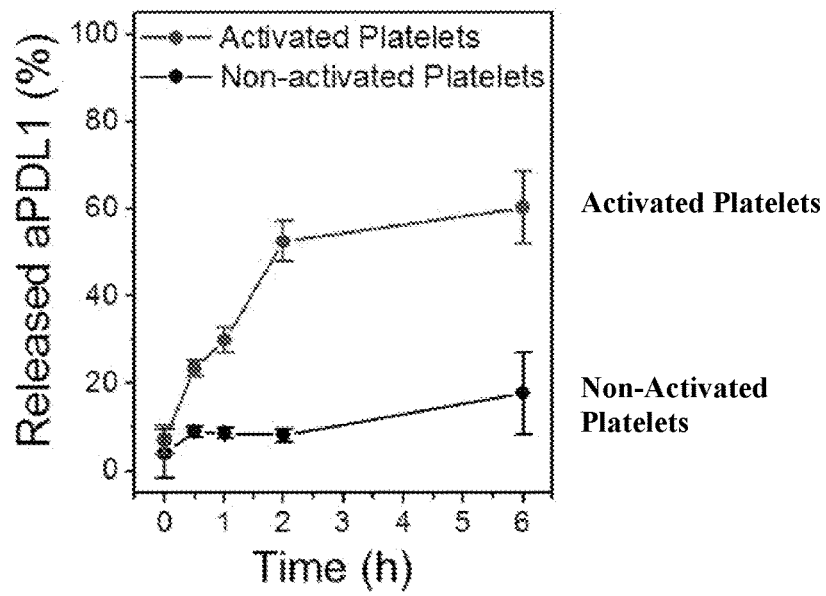

Platelet activation happens after adhesion occurs[45]. A platelet contains about 60 granules that contain many molecules with immune functions[38]. Upon activation, these granules release their inside cargo into the extracellular environment. Many of these contents play roles as immune molecules. For example, they could recruit and activate other immune cells, induce T-cell migration, and increase monocyte differentiation into DCs. Additionally, PMPs are derived from the plasma membrane upon platelet activation[43], activated platelets release PMPs carrying adhesion molecules and chemokines, facilitating monocyte traps at the site of PMP deposition[46]. To investigate whether aPDL1 modified platelets (P-aPDL1) could be activated upon stimulation, thrombin was used to activate P-aPDL1 in vitro. From observation of the transmission electron microscopy (TEM) images of P-aPDL1 before and after activation, a large amount of generated PMPs was detected under the electron microscope (FIG. 1b, FIG. 10). The dendritic and spread morphology changes of the platelets were also observed. More interestingly, significant release of aPDL1 from the activated platelets was monitored by the ELISA assay (FIG. 1c). The remarkable aPDL1 release was ascribed to the dissociated PMP from the plasma membrane upon the platelet activation. To test this hypothesis, immunofluorescence imaging of activated P-aPDL1 was carried out. Platelets were stained with calcein and aPDL1 was stained by the fluorescent secondary antibody (FIG. 11). It was detected that the aPDL1 was present on the PMPs after activation of platelets.

Figure 1D:
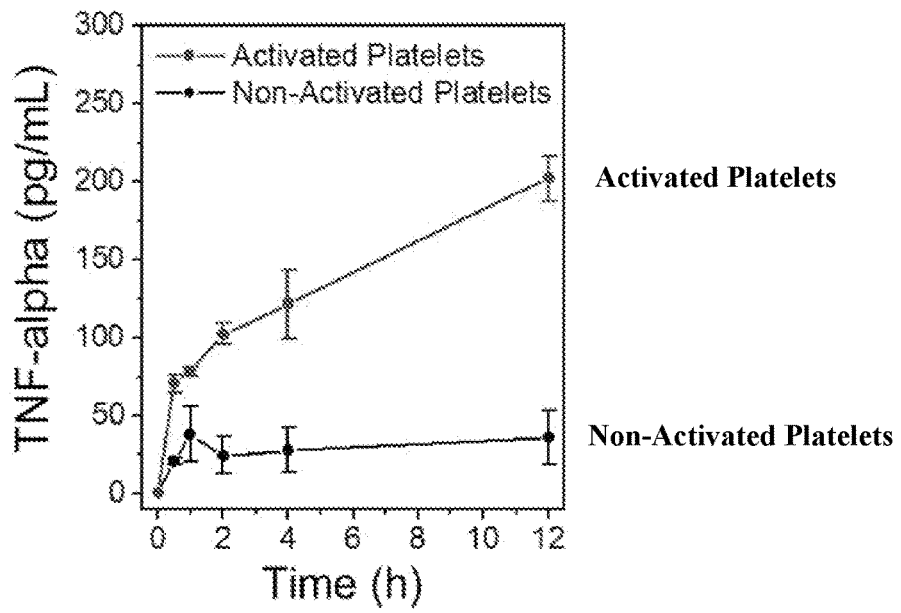
Figure 1E:
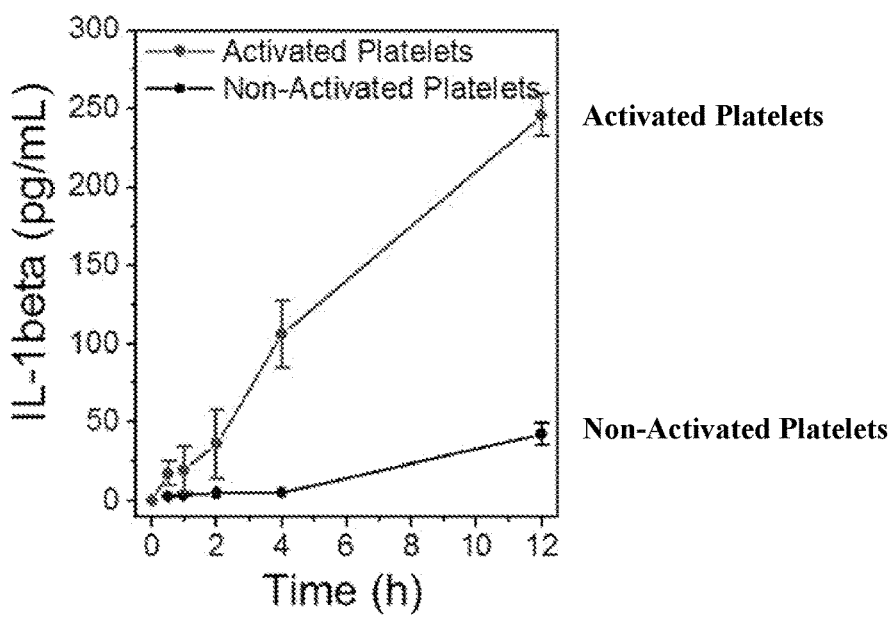
Figure 1F:
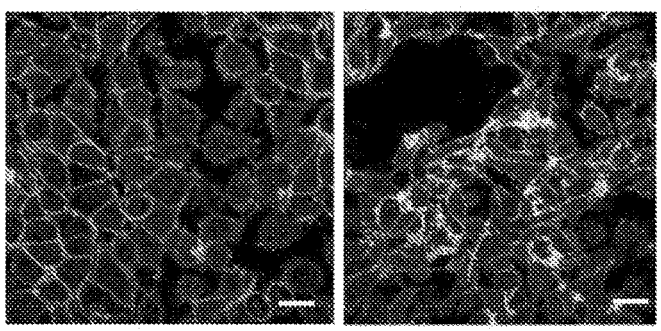
Figure 12B:
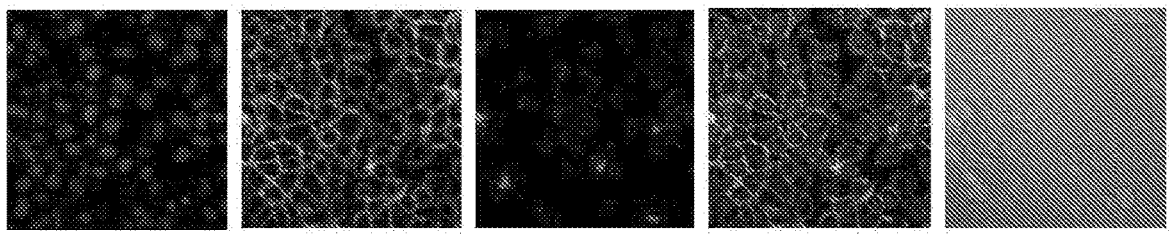
Figure 12B:
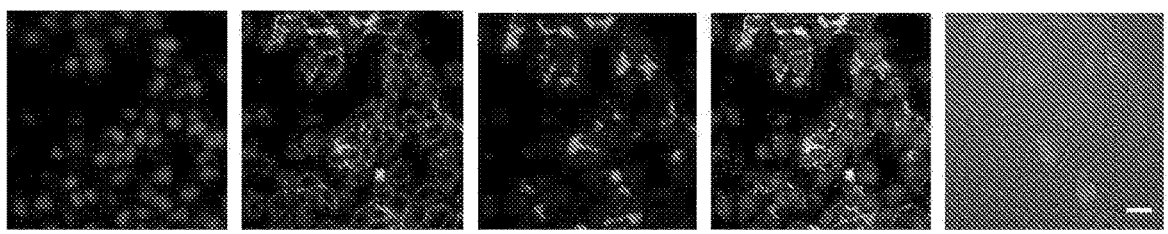

Of note, several pro-inflammatory cytokines were also released together with aPDL1 upon activation (FIG. 1d-e). To further examine the aPDL1 release from platelets by PMP generation, a transwell culture system was introduced. aPDL1 conjugated platelets were cultured in the upper compartment of the transwell culture system, while B16 cancer cells were grown in the lower compartment (FIG. 12). The micro-pores on the insert membrane had a diameter of 1 μm, allowing PMPs to cross the membrane freely. B16 cancer cells were co-incubated with nonactivated and activated platelets 12 hours before immunostaining. As shown in FIG. 1f and FIG. 12, aPDL1 was found to bind to the membrane of cancer cells when platelets were activated. As for the cancer cells incubated with nonactivated platelets, few signals could be detected on the cancer cells in the lower compartment. Collectively, the data shows that aPDL1 can be released from activated platelets and bind to cancer cells.

In Vivo P-aPDL1 Therapy Toward the Recurrent Tumors

Figure 2A:
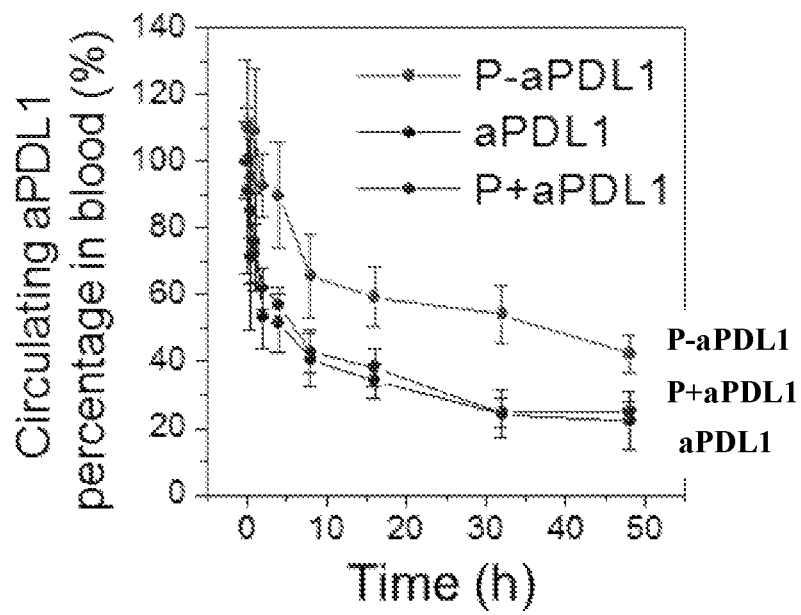
FIGS. 2A-2J. In vivo reduction of the recurrent melanoma tumors in the surgical bed by P-aPDL1 therapy.
Figure 2B:
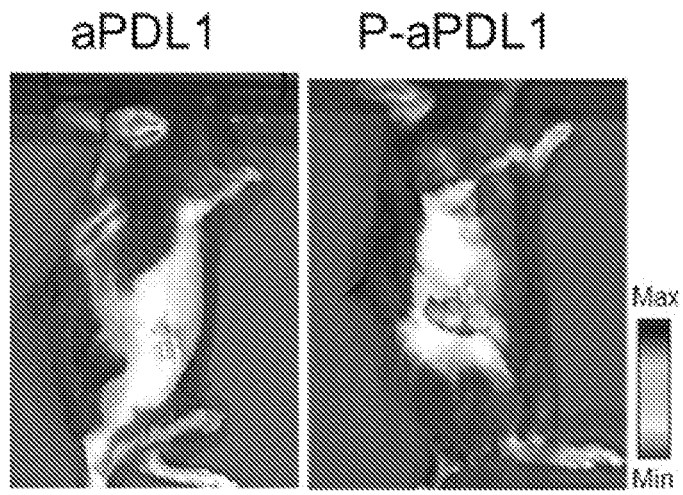
Figure 2C:
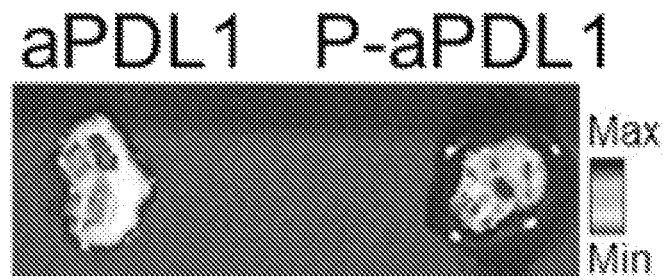
Figure 2D:
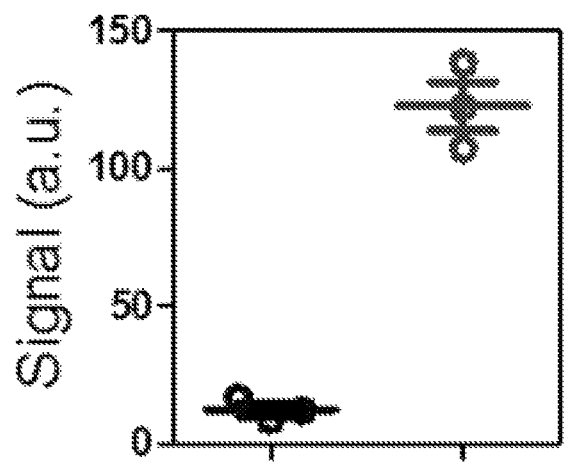
Figure 2E:
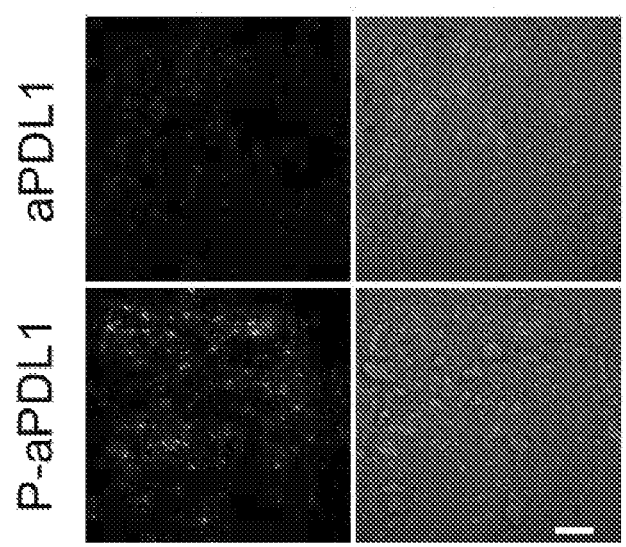
Figure 13A:
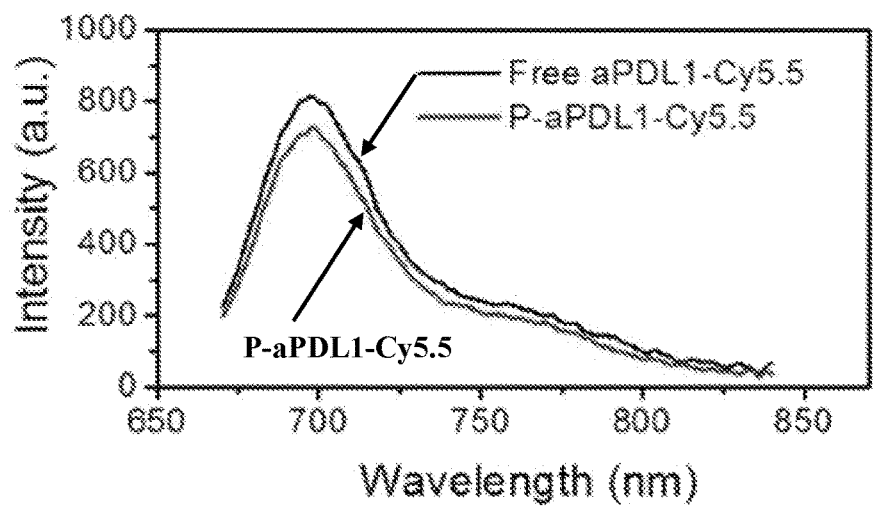
FIGS. 13A-13C. Biodistrubtion of aPDL1-coupled platelets in mice.
Figure 13B:
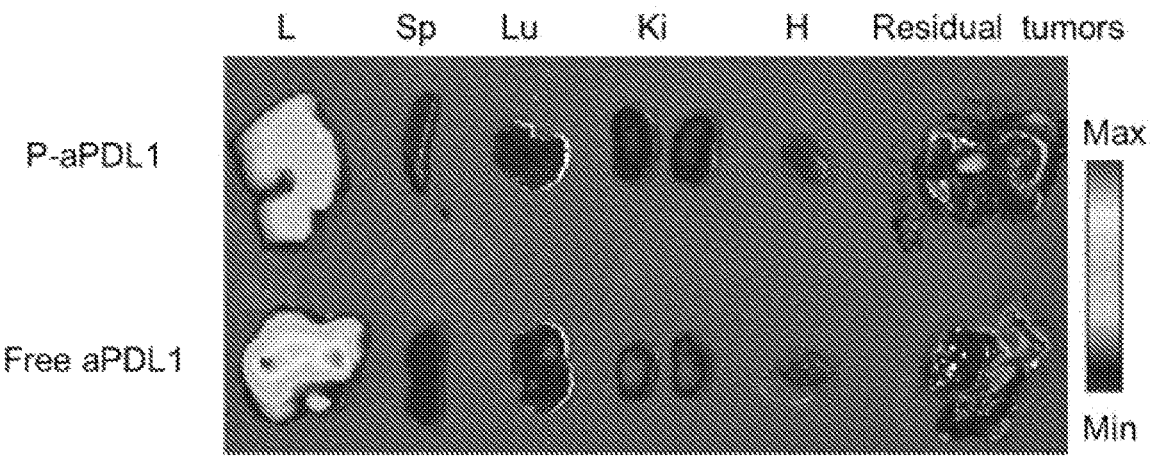
Figure 13C:
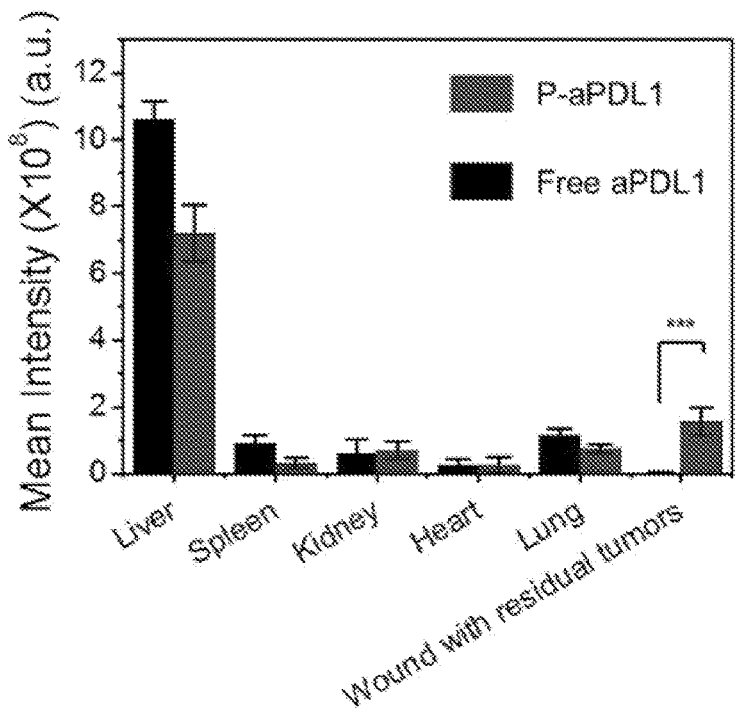
Figure 14A:
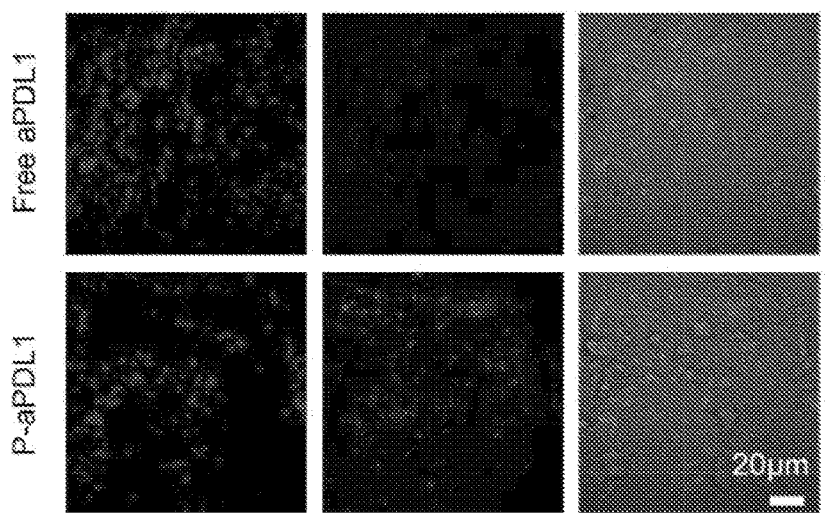
FIGS. 14A-14B. Confocal images of the residual tumor slices.
Figure 14B:
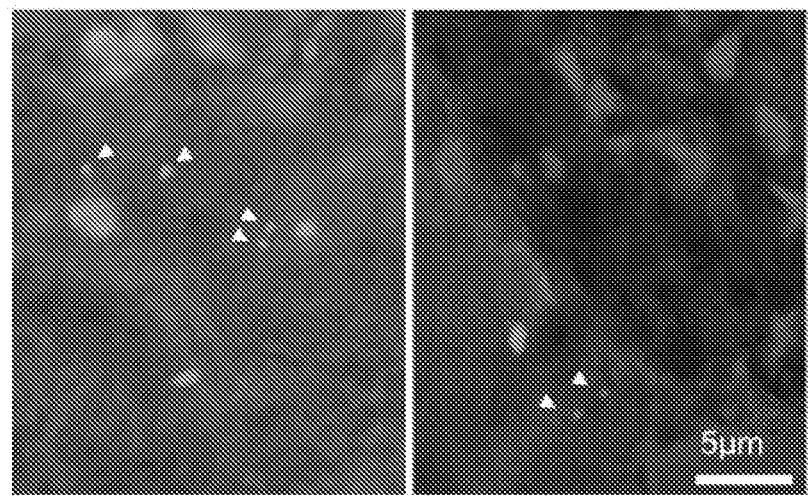
Figure 15:
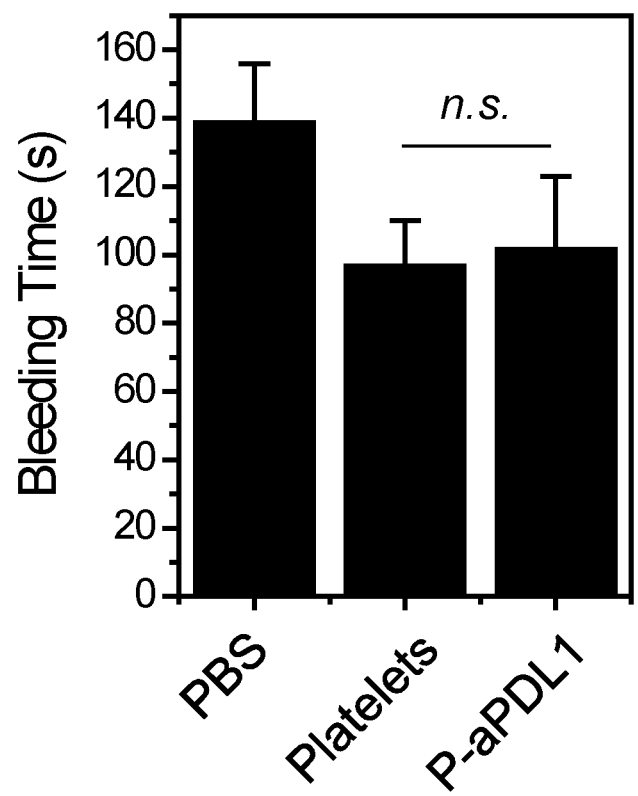
FIG. 15. Hemostatic effect in mouse tail transection bleeding model. Statistical significance was calculated by t-test. n.s., non-significant. The error bars are based on the standard deviations (SD) of triplicated samples (n=10)

Coupling of aPDL1 to the surface of platelets has the potential to alter their in vivo behavior. Therefore, the in vivo pharmacokinetics of P-aPDL1 following the systemic administration was evaluated in healthy mice. aPDL1, P-aPDL1 and co-injected unconjugated platelets+a-PDL1 were intravenously injected into mice with equivalent aPDL1 doses. ELISA analysis of aPDL1 from blood showed that a greatly prolonged blood-circulation half-life (34.8 hours) was achieved for the aPDL1 linked to platelets compared with free aPDL1 (5.2 hours) and mixture (5.5 hours) (FIG. 2a). The relatively short blood-circulation time compared with therapeutic antibodies in clinical is attribute to the higher immunogenicity and nonspecific binding of the rat anti-mouse IgG. Their wound-tropic capability was then tested after incomplete removal of the primary tumor by surgery. aPDL1 was labeled by Cy5.5 and then conjugated to platelets. In vivo fluorescence imaging was conducted two hours post injection of the P-aPDL1 or free aPDL1, with major organs collected for ex vivo fluorescence imaging (FIG. 13). It was observed that aPDL1 was enriched around the surgical wound with residual tumors when they were conjugated to the platelets, whereas insignificant fluorescence signal was detected at the wound site for the free aPDL1 (FIG. 2b). Ex vivo imaging of major organs as well as the wounds with residual microtumors further confirmed that the wound-tropic capability of P-aPDL1 (FIG. 2c, FIG. 13). It showed that the predominant aPDL1 fluorescence signal was detected in the liver of the mice injected with free aPDL1, whereas the P-aPDL1 showed a significantly lower aPDL1 signal in liver than those from free aPDL1 injected mice at the same aPDL1 dose, showing a longer blood circulation time of P-aPDL1. Meanwhile, significantly strong aPDL1 signal was detected around the surgical wound with the residual microtumors, whereas insignificant signal was detected in the sample associated with the free aPDL1. Quantification of the fluorescent signals showed that the accumulation at wounds of P-aPDL1 was 9.4-fold more efficient compared to that of the free aPDL1, at two hour post-i.v. injection (FIG. 2d). The confocal images of the microtumor slices also confirmed a significantly increased tumor uptake of aPDL1 when conjugated onto platelets (FIG. 2e, FIG. 14a). Moreover, aPDL1 released from platelets was clearly observed in vivo by the fluorescence imaging (FIG. 14b). The hemostatic effect of modified platelets was also examined. Mice tail bleeding time post-transfusion showed that P-aPDL1 treated mice had no statistically significant difference in bleeding time compared to those treated with the naïve platelet transfusion (FIG. 15).

Figure 16A:
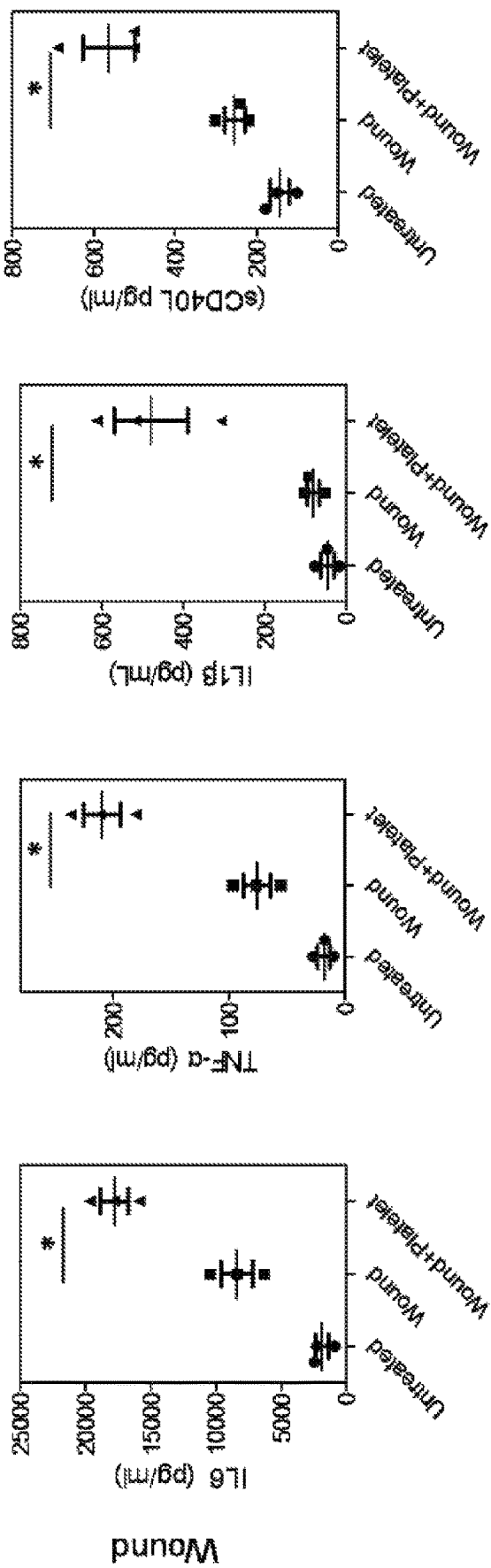
FIGS. 16A-16D. Cytokine levels of mice after treatments.
Figure 16B:
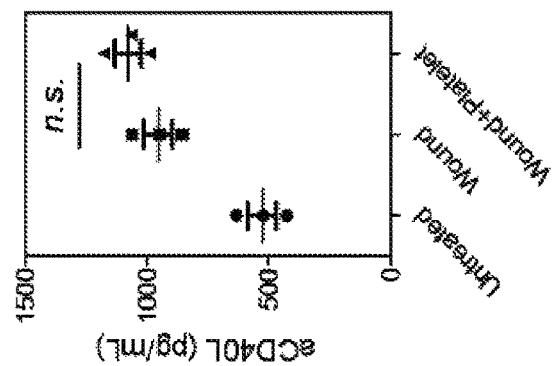
Figure 16B:
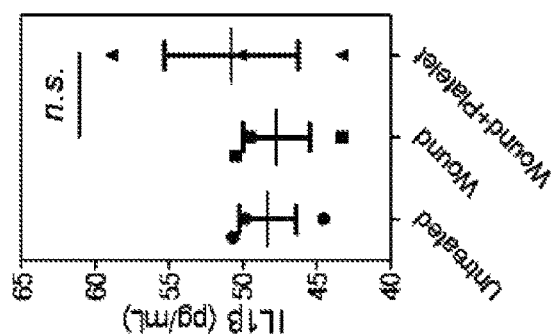
Figure 16B:
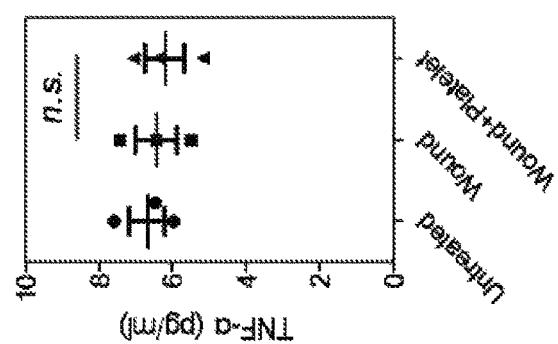
Figure 16B:
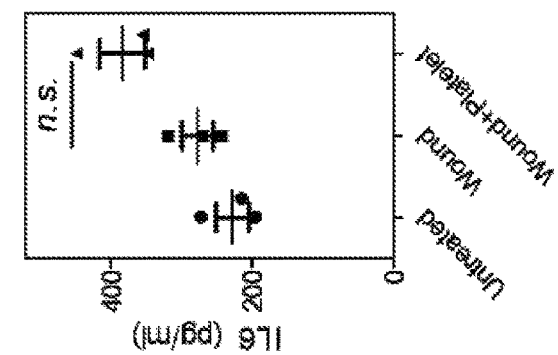
Figure 16C:
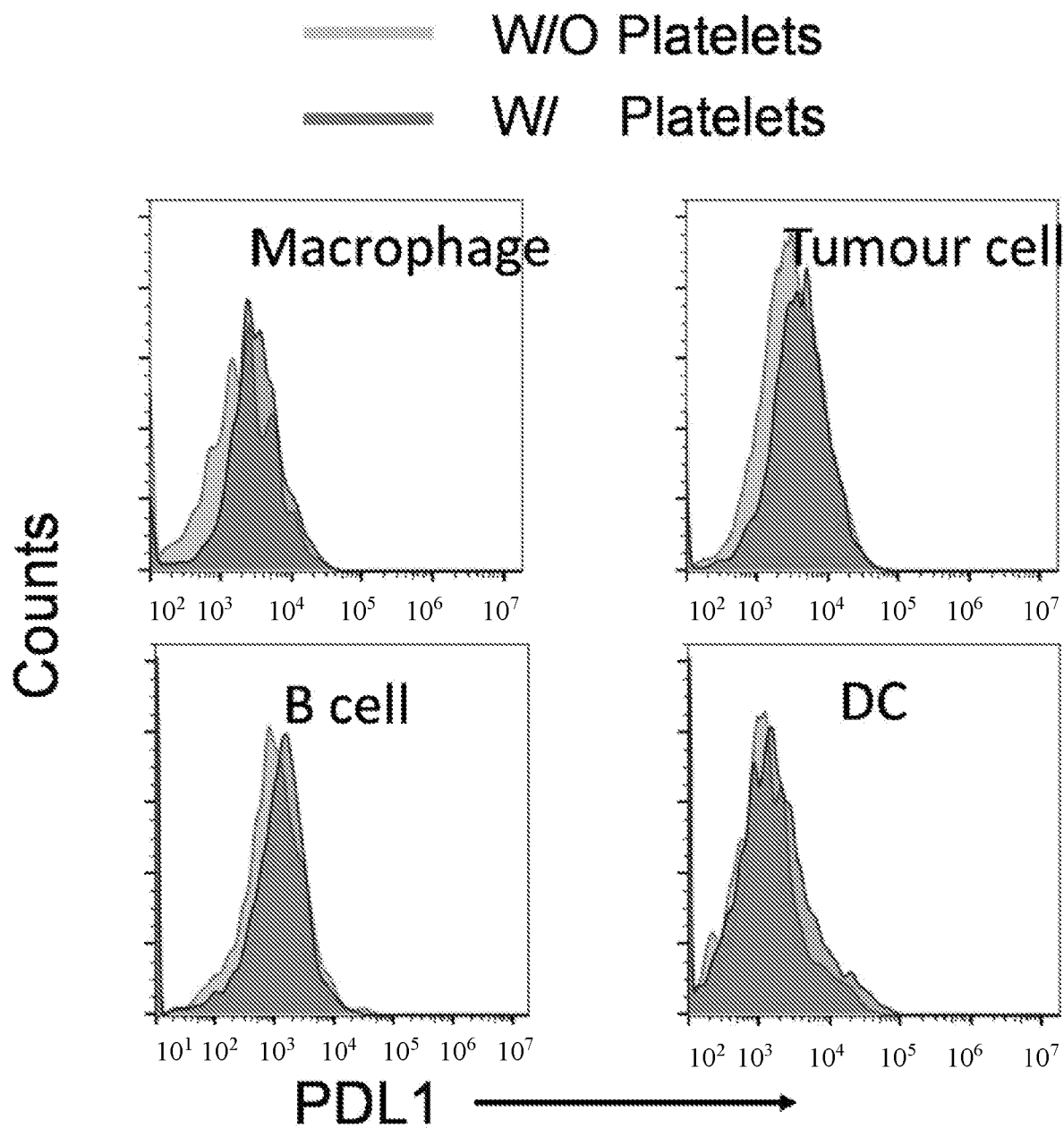
Figure 16D:
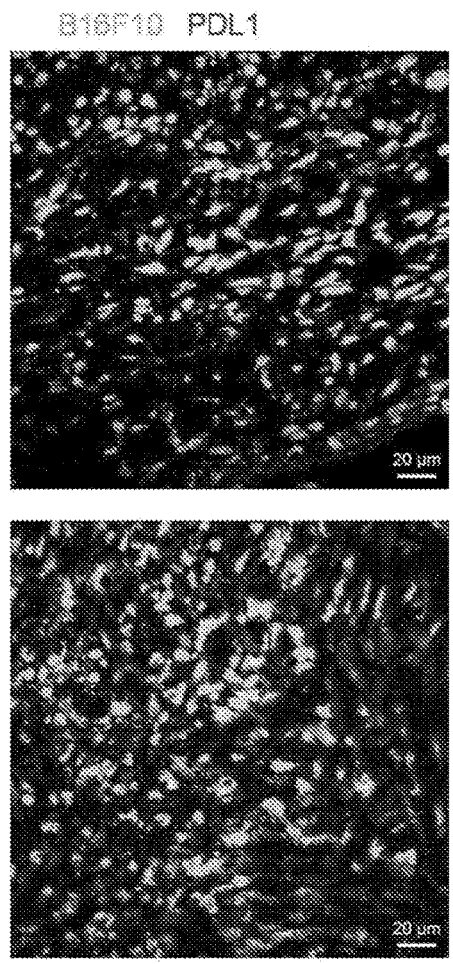

To investigate the pro-inflammatory environment in vivo, the cytokine level at the operative site was assessed. After surgically removing the primary tumor, the mice were i.v. injected with platelets. Two hours later, the wound tissues were collected and cultured in medium for 24 hours. Medium from the wound tissues was then tested for the activity of cytokines. It was found that the levels of IL-1β, IL-6, TNF-α, and sCD40L all exhibited apparent elevation compared with that from the untreated control and wound-bearing mice (FIG. 16a). The cytokines from the serum were also tested. Interestingly, platelets did not induce the secretion of these pro-inflammatory cytokines in the serum (FIG. 16b). These results show that the local inflammatory environment, rather than systemic inflammation, could be induced by platelets injection. The local pro-inflammatory environment is conducive to the aPDL1 immunotherapy by converting quiescent precursor lymphocytes into activated lymphocytes at the tumor site[47]. In addition, the PDL1 expression in the tumor site was also investigated. It was found that platelets induced inflammatory burden could upregulate PDL1 expression of tumor-infiltration immune cells and tumor cells (FIG. 16c-d). The increase of the PDL1 positive cells within tumor can further enhance the anti-PDL1 immunotherapy and increase the ORR.[41, 42]

Figure 2F:
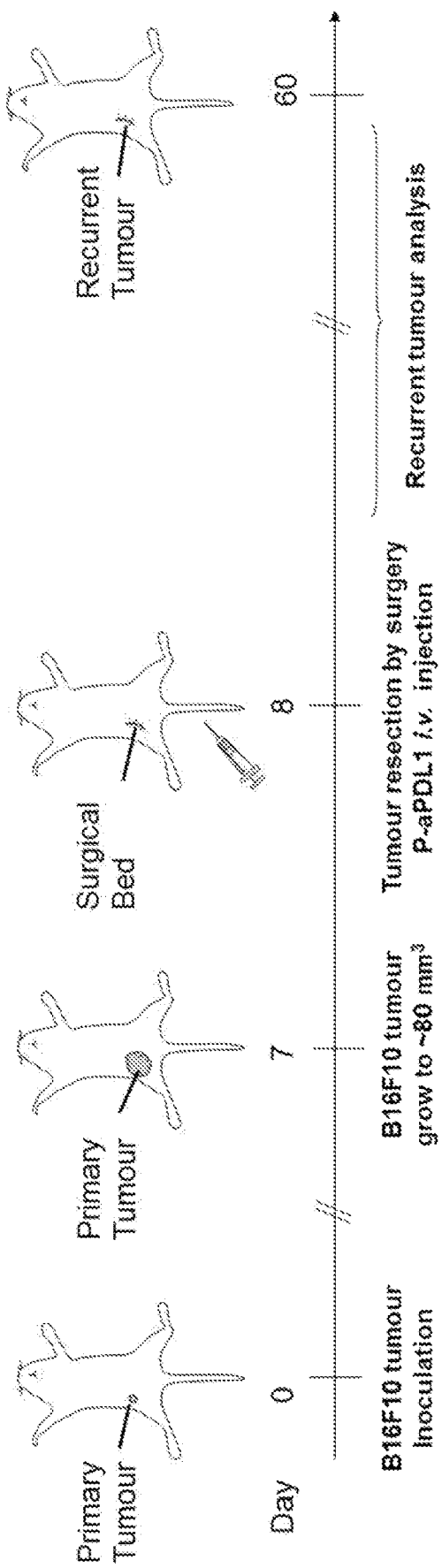
Figure 2G:
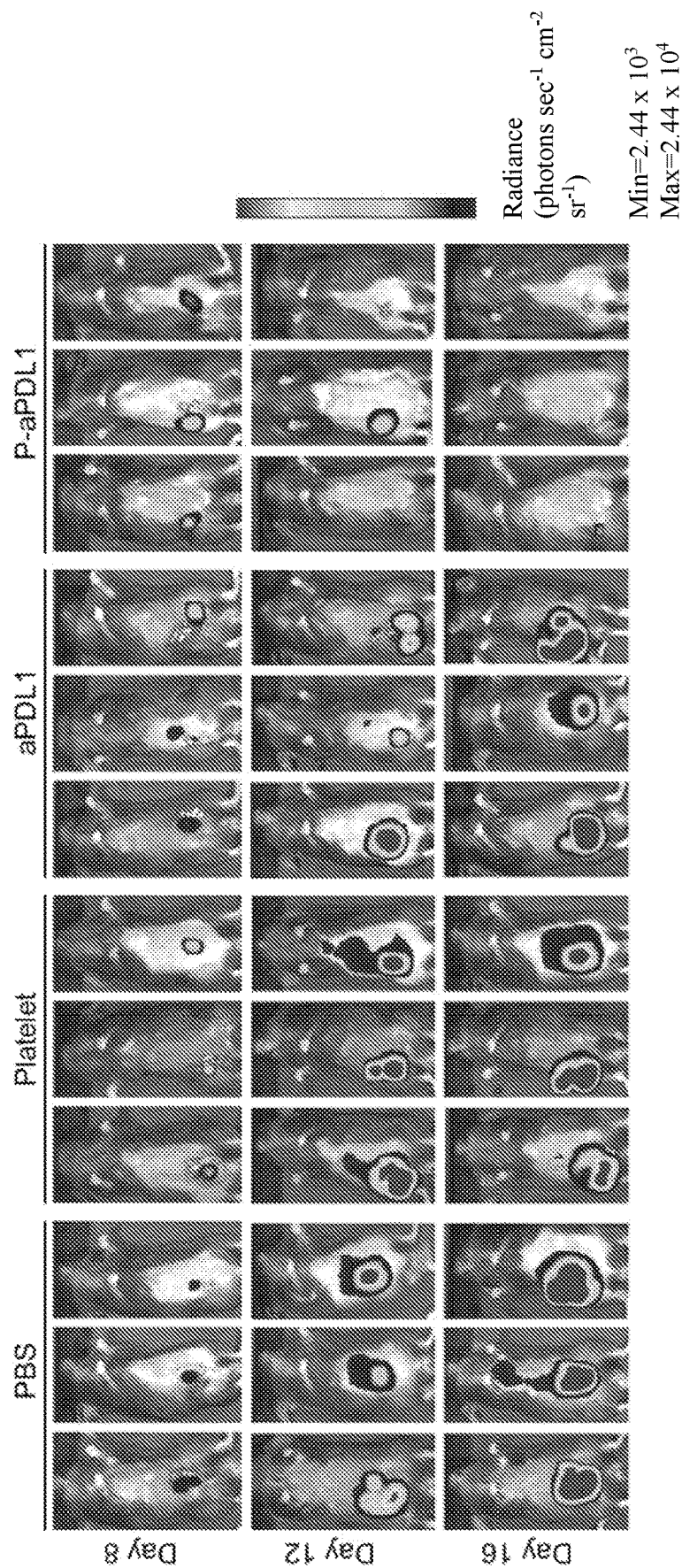
Figure 2H:
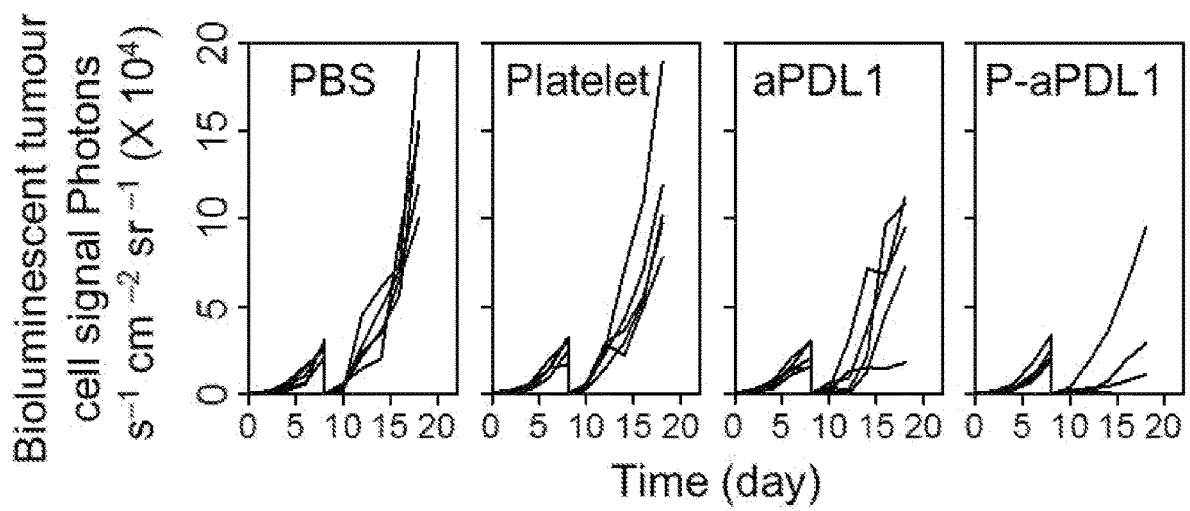
Figure 2I:
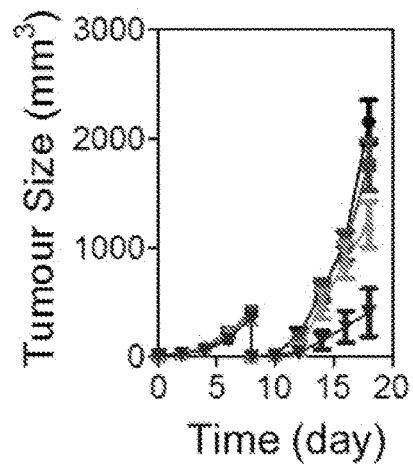
Figure 2J:
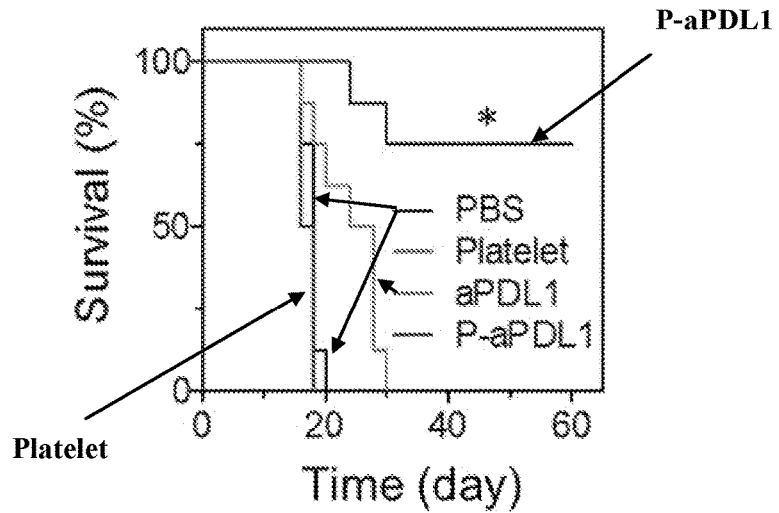

To treat the residual microtumors that remained after surgery, the B16F10 mouse melanoma incomplete tumor resection model was used to mimic the local recurrences post-surgically (FIG. 2f). After surgically removing most of the tumor (~99%), the mice were i.v. injected with a single dose of PBS, platelets, aPDL1 or P-aPDL1 (aPDL1=1 mg/kg). Tumor growth was monitored by the bioluminescence signals of B16F10 cells. It was demonstrated that the mice receiving P-aPDL1 displayed the smallest relapsed tumor volumes. 6 of 8 mice showed strong responses without any detectable tumor. Whereas the free aPD1 treated mice showed a modest delay of tumor growth but did not prevent tumor recurrence in the surgical bed. The prevention of tumor recurrence in mice treated with only platelets showed a similar effect to that of the PBS control (FIG. 2g-h). The tumor size in mice also correlated with their survival. About 75% of mice survived 60 days after treatment with P-aPDL1. In contrast, none of the mice survived in all control groups after 60 days (FIG. 2i).

T Cell-Mediated Immune Response Triggered by P-aPDL1 Therapy

Figure 3A:
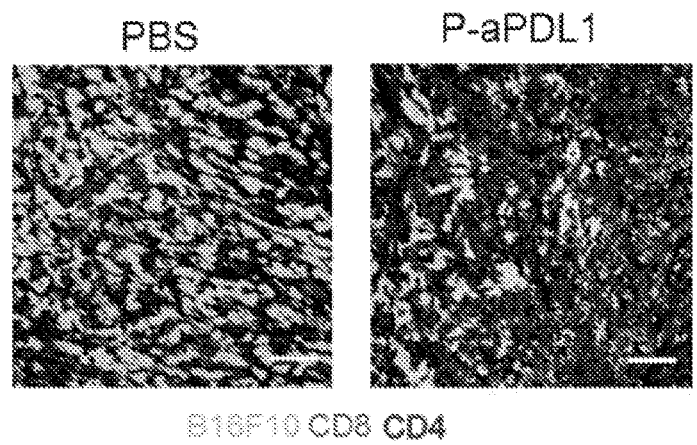
FIGS. 3A-3H. P-aPDL1 triggered a robust, T cell-mediated anti-tumor immune response.
Figure 3B:
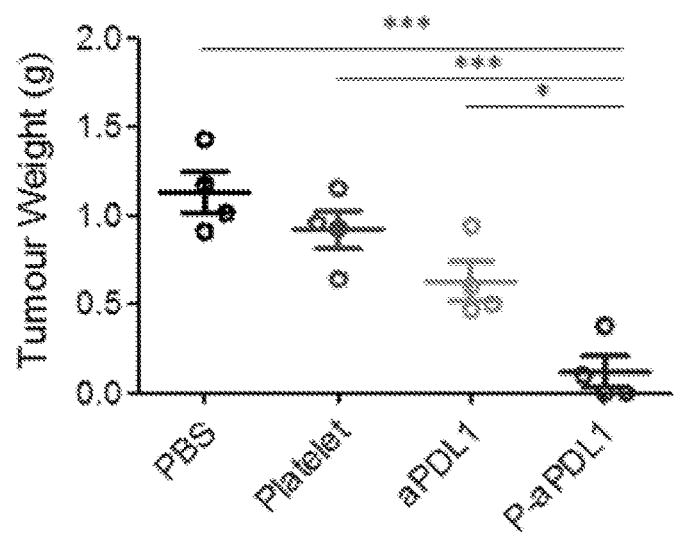
Figure 3C:
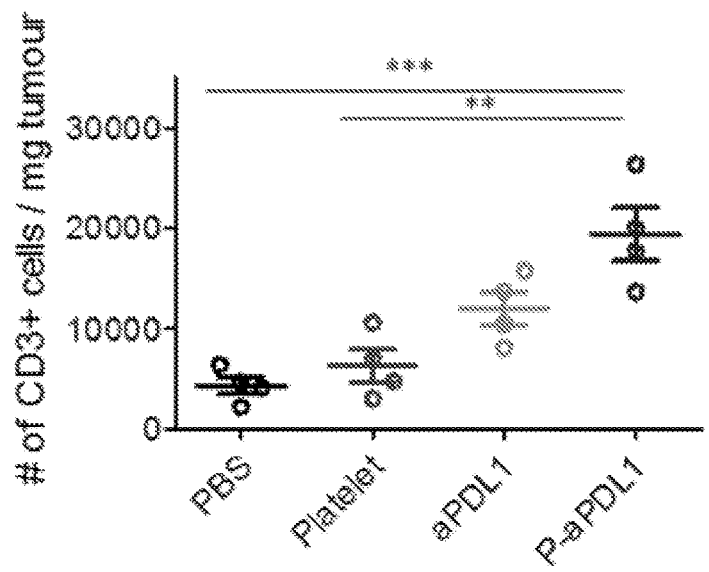
Figure 3D:
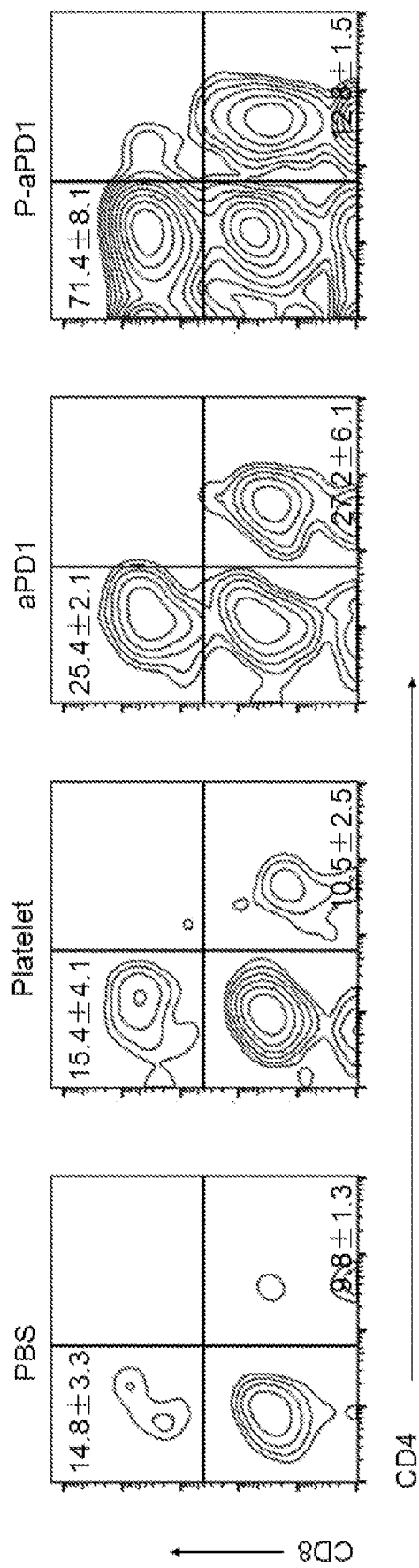
Figure 3E:
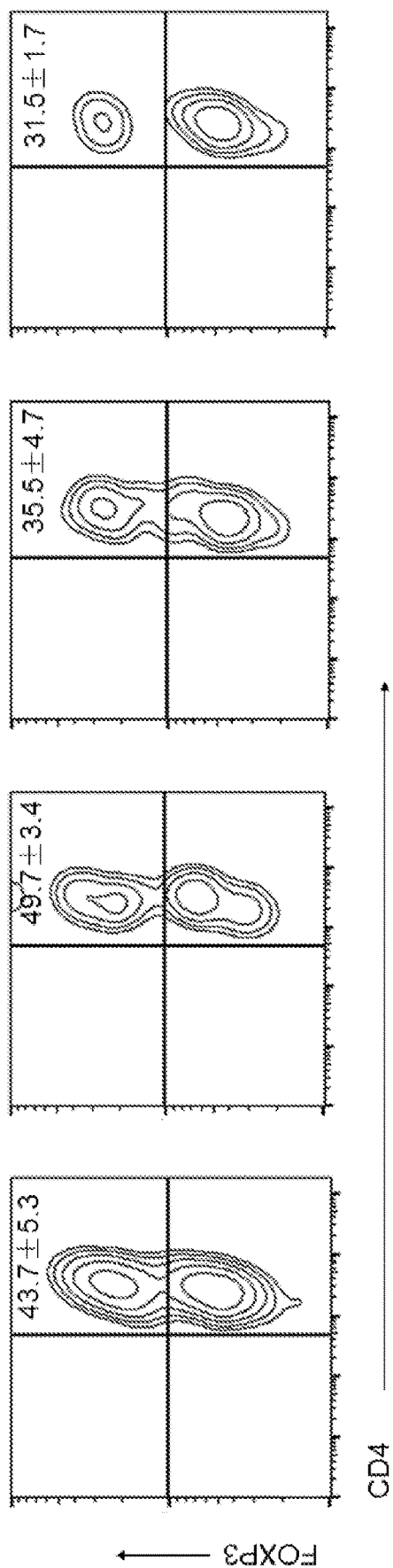
Figure 3F:
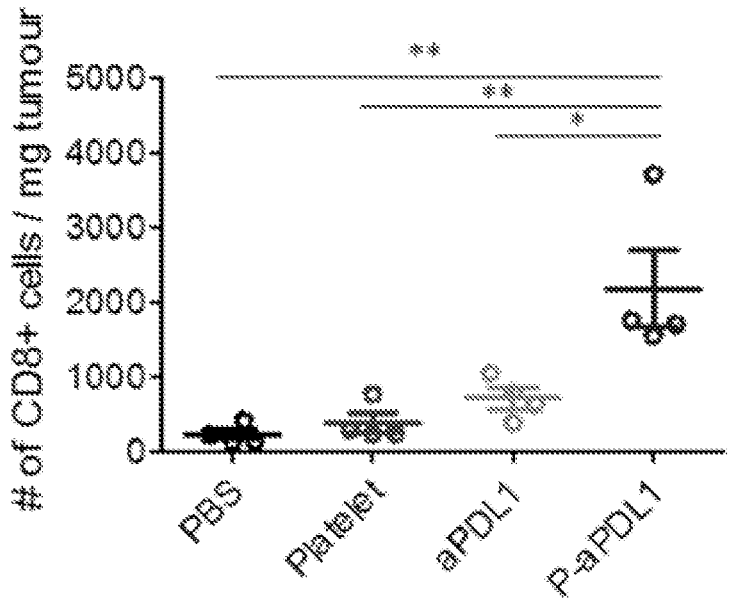
Figure 3G:
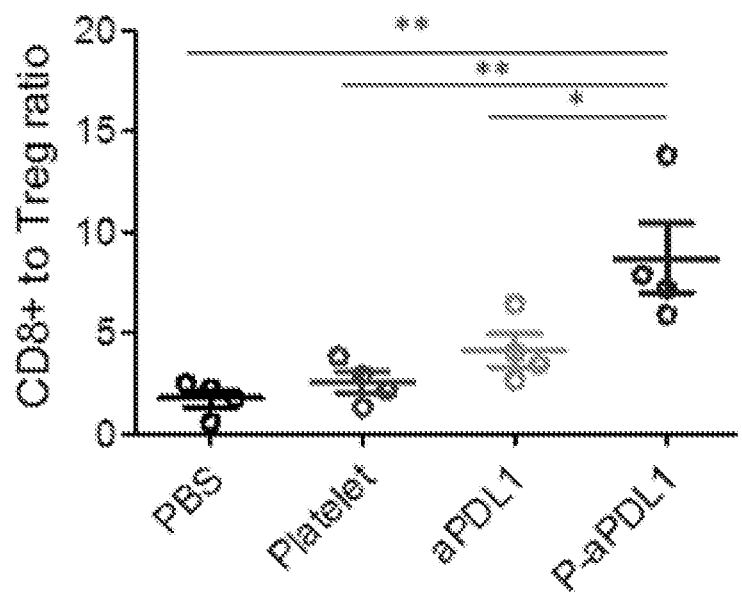
Figure 3H:
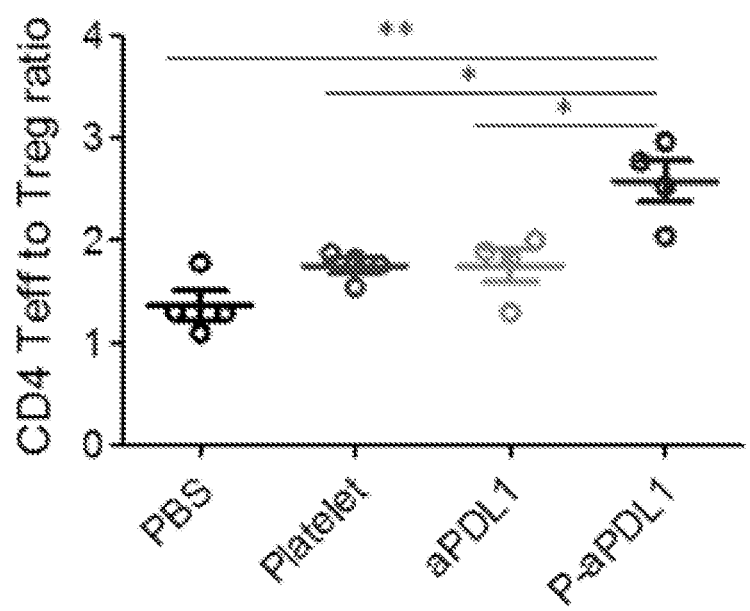
Figure 17:
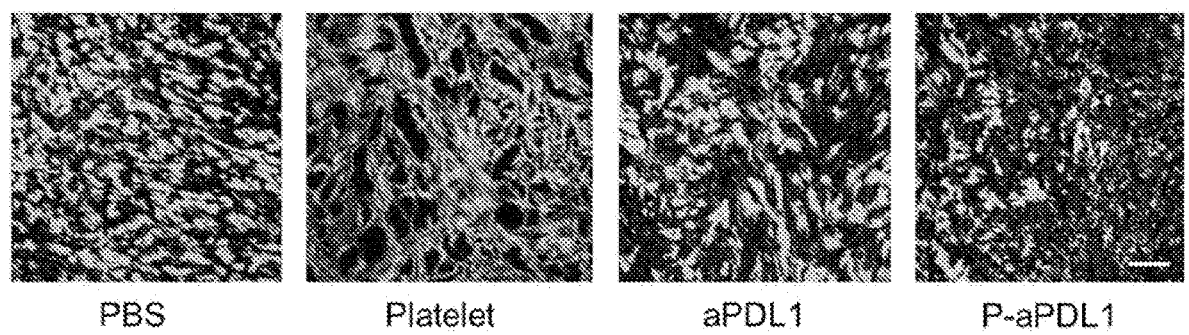
FIG. 17. Immunofluorescence of residual tumors showed CD4+ T cells and CD8+ T cells infiltration. Scale bar, 50 μm.
Figure 18:
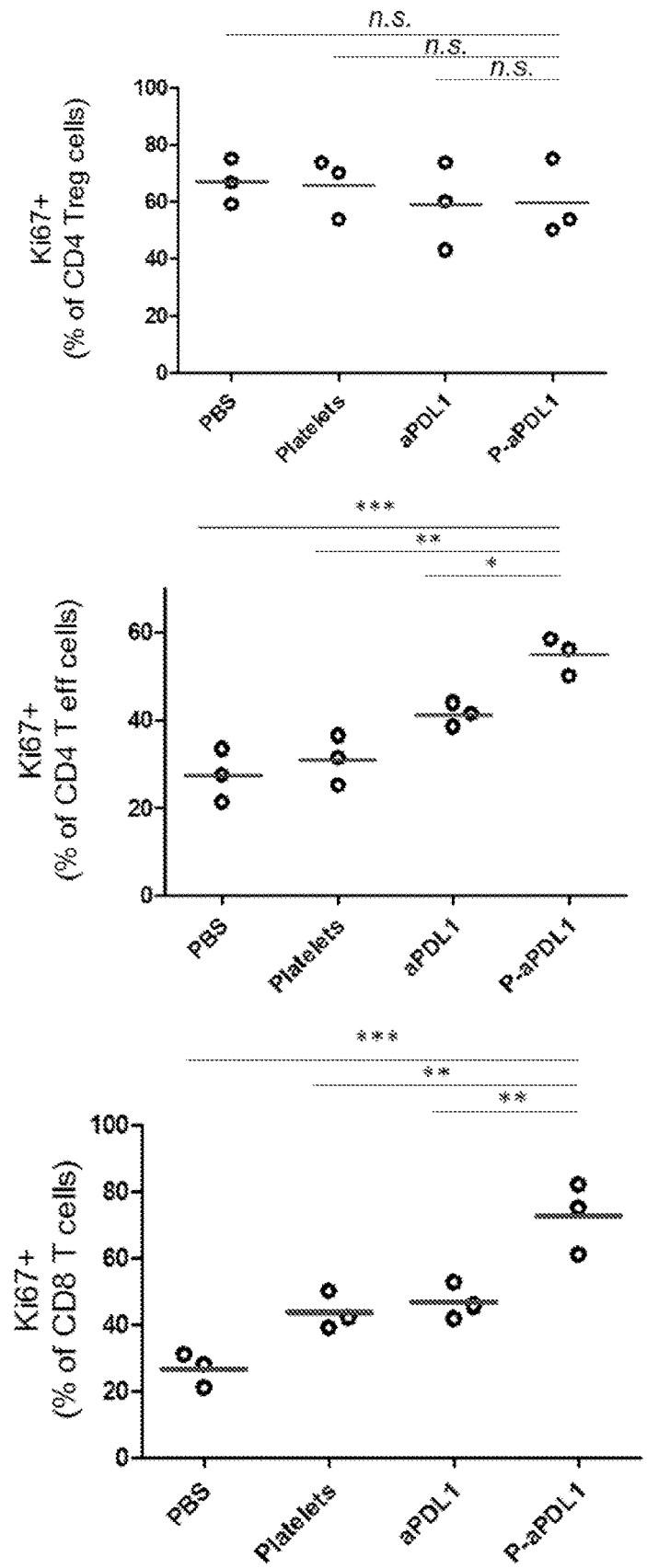
FIG. 18. Percentage of CD8+, CD4+Foxp3, and CD4+ Foxp3+ T cells expressing Ki67 with different treatments indicated. Statistical significance was calculated by one-way ANOVA using the Tukey post-test. P value: *, P<0.05; , P<0.01; *P<0.005.

In addition, tumor-infiltrating lymphocytes (TILs) from the recurrence tumors were harvested and analyzed by the immunofluorescence and flow cytometry on day 16. Immunofluorescence staining revealed that the residual tumors in the control group had limited T-cell infiltration. In contrast, the residual tumors from P-aPDL1 treated mice were remarkably infiltrated by both CD8+ and CD4+ T cells (FIG. 3a, FIG. 17). The tumor weights were significantly lower in the P-aPDL1 treated mice on day 10 (FIG. 3b), which also corresponded to an increase in absolute number of CD3+ cells in the residual tumor (FIG. 3c). More remarkably, the absolute number of CD8+ T cells/gram of tumor increased by almost 10-fold in the P-aPDL1 treated mice compared with the PBS control and 3-fold over the free aPDL1 treated mice (FIG. 3d-f). Additionally, the tumor-infiltrating CD4+ FoxP3+ T cells were studied (FIG. 3e). Intratumoral ratios of T effector cells to regulatory T (Treg) cells were significantly enhanced in mice after P-aPDL1 therapy (FIG. 3f-h). In addition, a high CD8+ and CD4+ effector T cell proliferation within the tumors of P-aPDL1 mice was observed, as measured by the expression of the cell cycle associated protein Ki67. In contrast to the effector T cells, there was no significant increase in proliferation by the tumor-infiltrating Treg cells with P-aPDL1 therapy (FIG. 18). Taken together, these observations show that P-aPDL1 can deliver aPDL1 to the tumor microenvironment effectively, triggering a robust and T cell-mediated anti-tumor immune response.

P-aPDL1 Therapy for Metastatic Disease

Figure 4A:
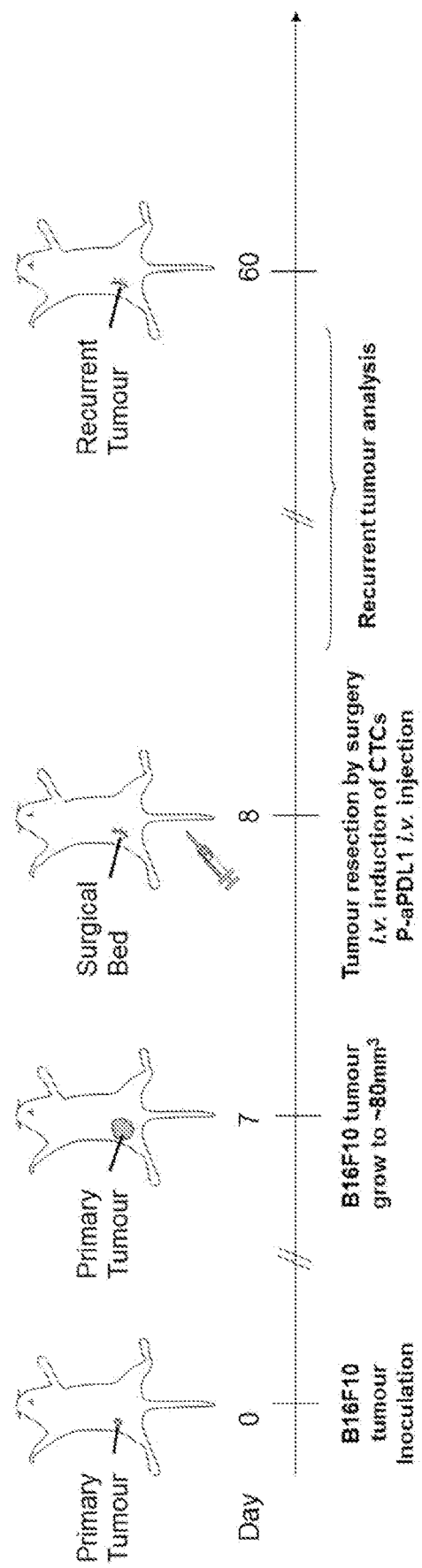
FIGS. 4A-4F. P-aPDL1 therapy affected the growth of the local recurrent melanoma tumor and metastatic disease.
Figure 4B:
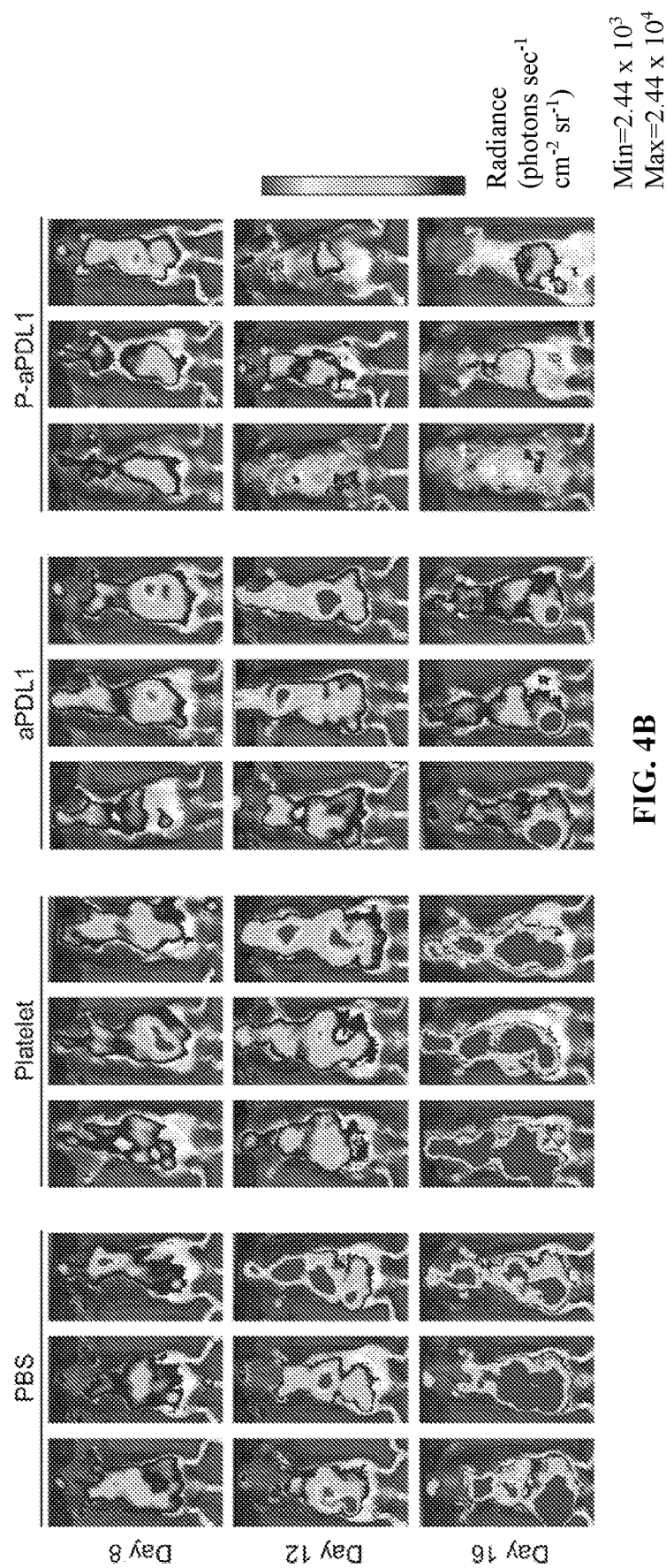
Figure 4C:
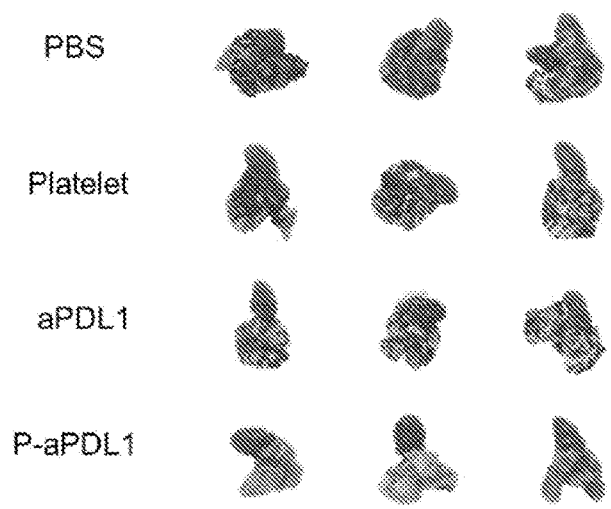
Figure 4D:
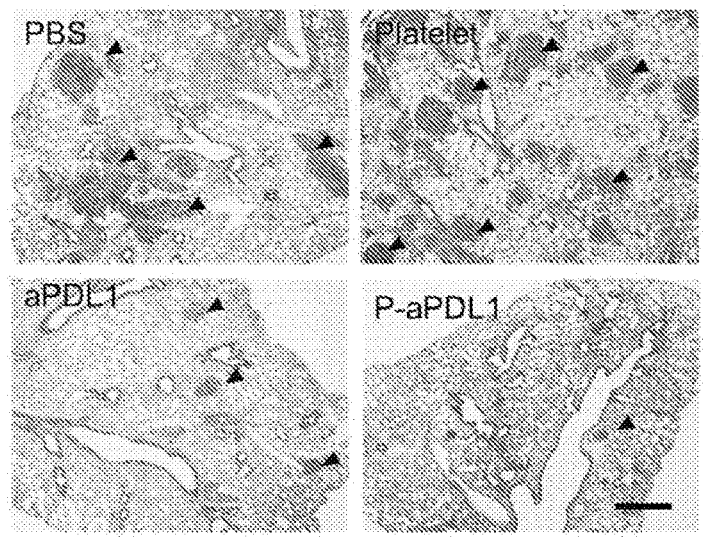
Figure 4E:
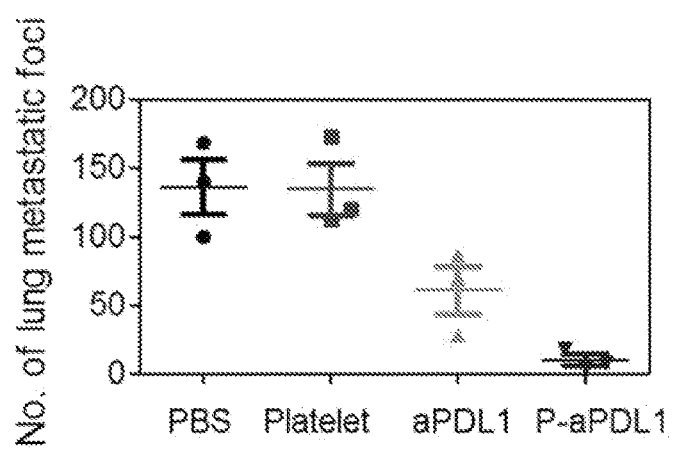
Figure 4F:
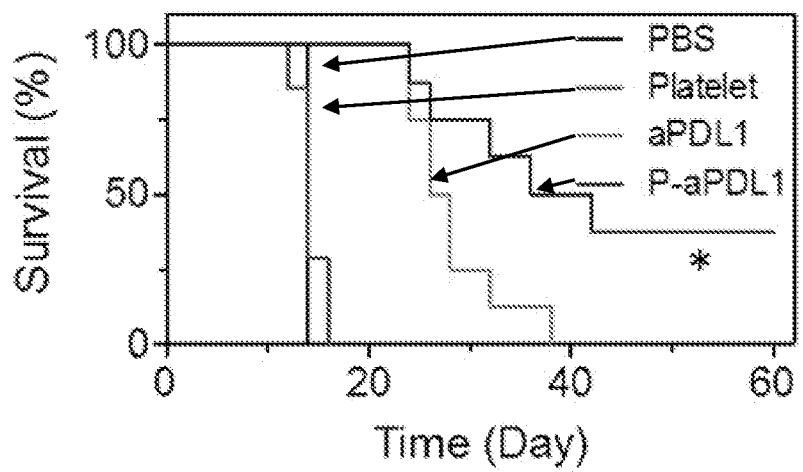
Figure 19A:
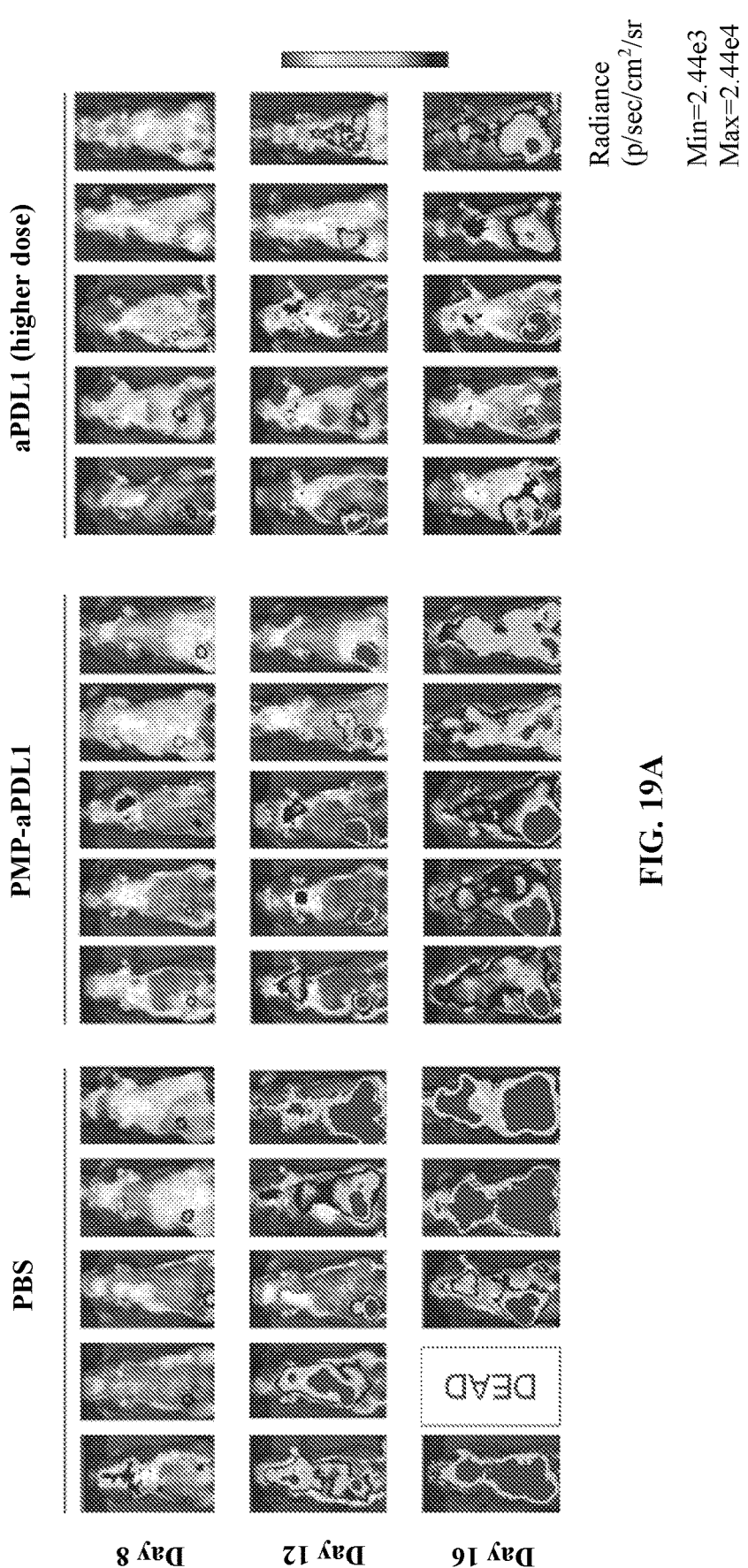
FIGS. 19A-19C. Anti-tumor efficiency of PMP-aPDL1 and high dose of aPDL1 after removal of the primary tumor.
Figure 19B:
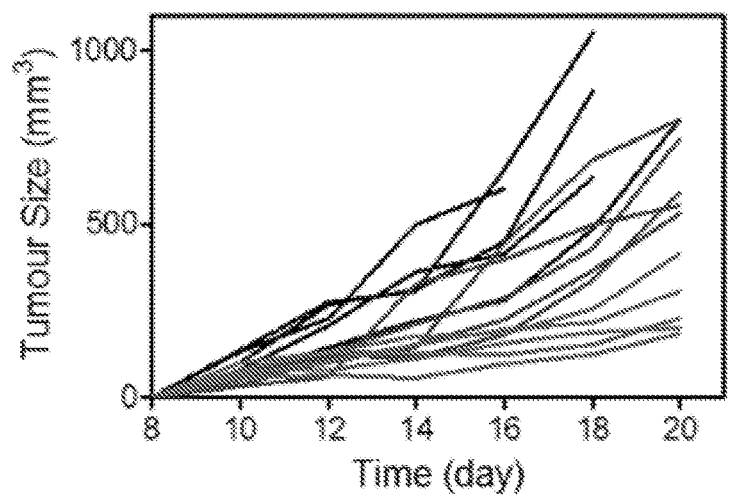
Figure 19C:
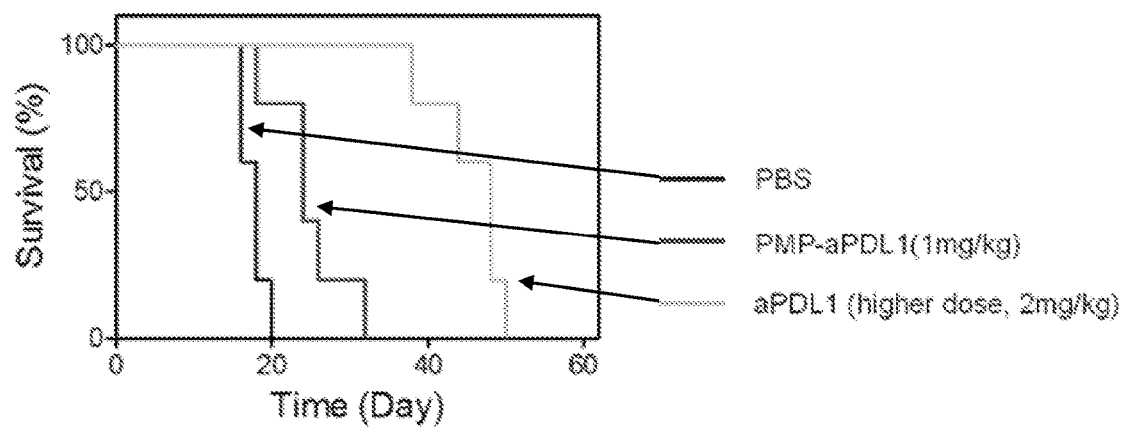
Figure 20:
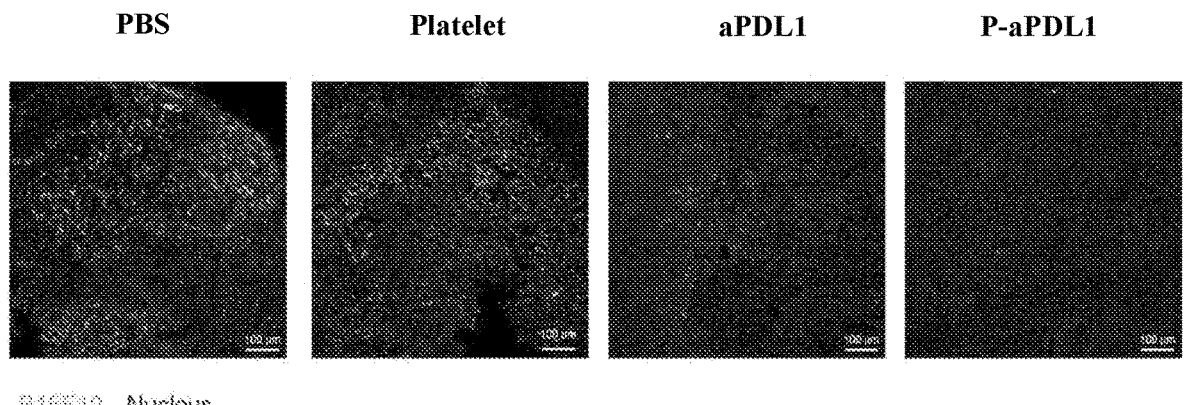
FIG. 20. Fluorescence imaging of lung tissue. Blue and green fluorescence represent nucleus from DAPI and GFP cancer cells, respectively. Scale bar, 100 μm.

To further demonstrate the potency of P-aPDL1 to treating CTCs, P-aPDL1 was first tested in an experimental metastasis tumor model by challenging mice with i.v. injection of the B16F10 cells after surgery, mimicking the CTCs escape from the primary tumor to the blood circulation[48] (FIG. 4a, FIG. 19). The mice were i.v. injected with a single dose of PBS, platelets, aPDL1 (aPDL1=1 mg/kg or 2 mg/kg) or P-aPDL1 (aPDL1=1 mg/kg), immediately after surgery. According to the bioluminescence signal of B16F10 cells in mice (FIG. 4b, FIG. 19), it was demonstrated that the free aPDL1 treatment could prevent metastatic cancer, but could not prevent the local tumor recurrence at the surgical site even at a higher dose of 2 mg/kg, possibly due to the poor accumulation of aPDL1 to these residual microtumors after surgery (FIG. 13). In contrast, a remarkably reduced recurrence of tumors at the surgical bed, as well as the lung metastasis, was achieved after the P-aPDL1 therapy, as confirmed by photos of the whole lungs together with their Hematoxylin and Eosin (H&E) staining imaging (FIG. 4c-d) as well as fluorescence imaging of lung tissue (FIG. 20). The average number of metastatic sites in lungs dramatically decreased when treated with P-aPDL1 (FIG. 4e). Furthermore, the survival time of the treated mice significantly increased compared to the control groups (FIG. 4f). Compared with free aPDL1, the better anticancer effects of P-aPDL1 was partly attributed to an increased local concentration of antibodies around cancer cells (FIG. 13). Meanwhile, platelet activation was also a functional component of the anticancer effects, as the activation not only could release the conjugated aPDL1, but also help recruiting many other immune cells infiltrate into TME. With the PDL1 blockade, these immune cells could induce strong anticancer immune responses.

To further verify whether in situ activation of the P-aPDL1 contributed to the anticancer effects, the PMPs were collected and modified with aPDL1 (FIG. 19). It clearly displayed that directly injecting these microparticles limited anticancer effects compared to the whole platelet, even no better than the free aPDL1 (FIG. 4). This could be explained by the previous studies that validated that the PMPs can be cleared rapidly following introduction into the circulation[49, 50]. These results substantiated that in situ activation of the P-aPDL1 in the tumor site was an essential component for enhancing the anticancer effects of P-aPDL1.

P-aPDL1 for 4T1 Recurrent Cancer after Surgery

Figure 5A:
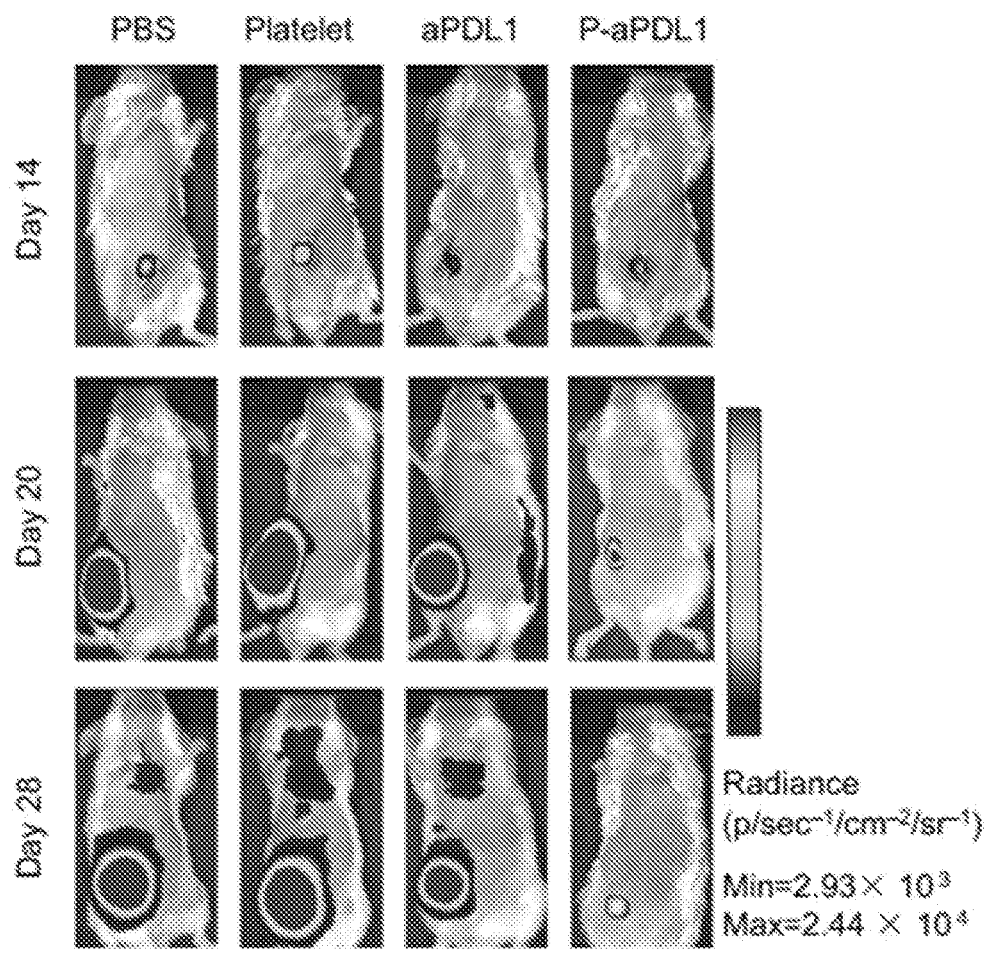
FIGS. 5A-5E. P-aPDL1 to treat 4T1 recurrent cancer after surgery.
Figure 5B:
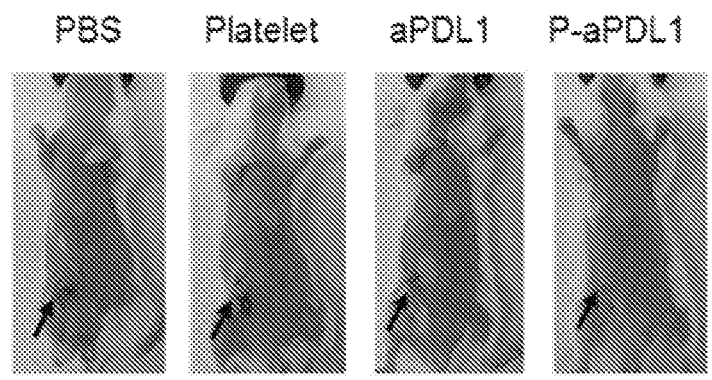
Figure 5C:
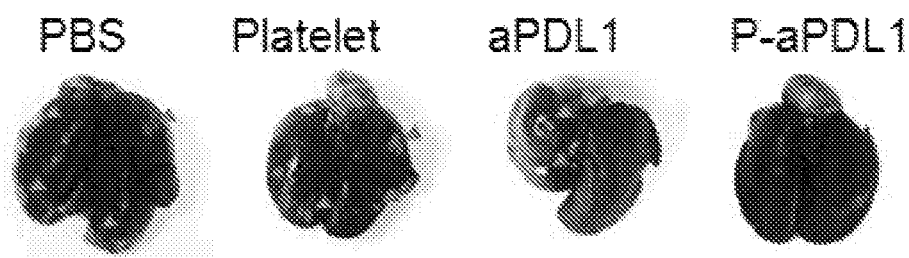
Figure 5D:
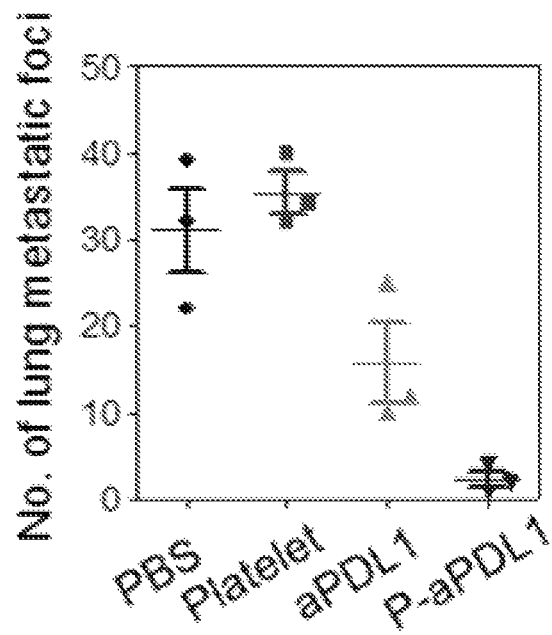
Figure 5E:
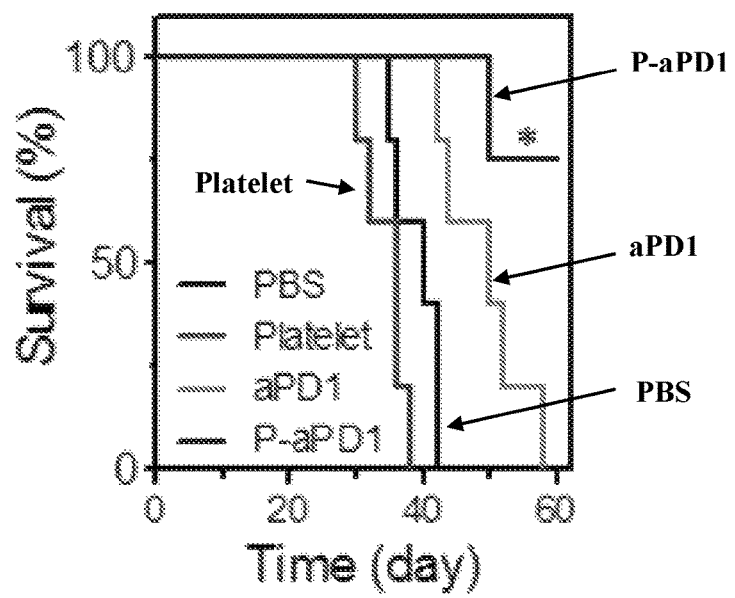

To assess the potency of P-aPDL1 in preventing another type of cancer recurrence after surgery, tests were performed in a triple-negative breast cancer (TNBC) 4T1 carcinoma tumor model. In this experiment, BABL/c mice were subcutaneously (s.c.) injected with the 4T1 tumor cells. Fourteen days after s.c. tumor inoculations, the primary tumor was removed by surgery, leaving ~1% residual microtumors behind. Therapeutic platelets coupled with aPDL1 were i.v. injected to the mice immediately after surgery. In this model, a single course of P-aPDL1 therapy was significant enough to affect the growth of the residual tumor after surgery (FIG. 5a-b). In addition, the therapy's effect on lung metastases was also impressive, as only a few nodules were found in the lungs of the P-aPDL1 treated mice, as opposed to a median of 16 nodules found in the free aPDL1 treated mice and ~30 nodules in platelet treated and untreated mice (FIG. 5c-d). Mice with P-aPDL1 therapy after surgery had derived substantial survival benefits in contrast with the control groups. 75% of the mice survived 60 days after tumor inoculation (FIG. 5e).

In summary, this example utilized in situ activation of platelets for promoted delivery of aPDL1, which can substantially eradicate residual tumor cells after surgery and prevent cancer recurrence. The P-aPDL1 therapy can maximize the effectiveness of surgical interventions and reduce the risk of cancer recurrence and metastasis after resection of the primary tumor. Beyond using platelet for aPDL1 delivery, this delivery method is also applied to other therapeutic agents and treatments that apply bio-particulates for targeted delivery and bio-responsive release of therapeutics.[51]

Methods and Materials

Cell Lines

The mouse melanoma cell line B16F10 and mouse mammary carcinoma cell line 4T1 were purchased from the American Type Culture Collection. B16F10-luc-GFP and 4T1-luc-GFP cells were gifts from Dr. Leaf Huang at The University of North Carolina at Chapel Hill. The B16F10 cells were maintained in Dulbecco's Modified Eagle Medium (Gibco, Invitrogen) supplemented with 10% fetal bovine serum (Invitrogen, Carlsbad, Calif.), 100 U/mL penicillin (Invitrogen), and 100 U/mL streptomycin (Invitrogen). The 4T1 cells were maintained in RPMI-1640 Medium (Gibco, Invitrogen) supplemented with 10% fetal bovine serum (Invitrogen, Carlsbad, Calif.), 100 U/mL penicillin (Invitrogen), and 100 U/mL streptomycin (Invitrogen). Master and working cell banks were generated immediately upon receipt. The third and fourth passages were used for tumor experiments. Cells were tested every three months for potential mycoplasma. Reauthentication of cells was not performed after receipt.

Mice

C57BL/6 mice and BALB/c mice were purchased from Jackson Lab (USA). Age-matched (6-10 weeks) female animals were used throughout all experiments. All mouse studies were performed in the context of the animal protocol approved by the Institutional Animal Care and Use Committee at the University of North Carolina at Chapel Hill and North Carolina State University. Experimental group sizes were approved by the regulatory authorities for animal welfare after being defined to balance statistical power, feasibility, and ethical aspects. All mice were kept in accordance with federal and state policies on animal research at the University of North Carolina at Chapel Hill and North Carolina State University.

Antibodies

Anti-PDL1 antibody (aPDL1) used in vivo was purchased from Biolegend Inc (Cat. #124329, Clone: 10F.9G2). Staining antibodies included CD3 (Thermo Fisher Scientific, Cat. #A18644), CD4 (Thermo Fisher Scientific, Cat. #A18667), CD8 (Thermo Fisher Scientific, Cat. #A18609), PD1 (Biolegend, Cat. #135227), CD11c (Biolegend, Cat. #117309), PDL1 (Biolegend, Cat. #124311), CD20 (Biolegend, Cat. #150411), CD11b (Biolegend, Cat. #101211), CD9 (Biolegend, Cat. #124805), CD41 (Biolegend, Cat. #133905), CD61 (Biolegend, Cat. #104307), CD62P (Biolegend, Cat. #148305), CD40L (Biolegend, Cat. #106505), intracellular Ki67 (Biolegend, Cat. #652405), and intracellular Foxp3 (eBioscience, Cat. #.71-5775-40) for fluorescence-activated cell sorting (FACS) analysis following manufacturers' instructions. The stained cells were analyzed on a Calibur FACS instrument (BD), and analyzed using FlowJo software (version 10). Secondary Antibody including Goat anti-Rat IgG (H+L) Secondary Antibody (Thermo Fisher Scientific, Cat. #A18866), Rabbit anti-Rat IgG (H+L) Secondary Antibody (Thermo Fisher Scientific, Cat. #A18920), Goat anti-rat IgG (minimal x-reactivity) Antibody (Biolegend, Cat. #405408) were used for immunostaining.

Preparation of aPDL-1 Conjugated Platelets

Murine platelets were isolated as described.[52] In brief, whole blood was collected from the C57BL/6 (or BALB/c) mice (nonterminal blood collection, from the orbital sinus or saphenous vein, 20 mice were used for blood collection) into a plastic syringe containing 1.0 mL citrate-phosphate-dextrose (16 mM citric acid, 90 mM sodium citrate, 16 mM $NaH_2PO_4$, 142 mM dextrose, pH 7.4.) and spun at 100 g for 20 min at room temperature with no brake. The platelet-rich plasma (PRP) was transferred to a separate tube using a transfer pipette (wide orifice), and PGE1 was added to a final concentration of 1 μM to each tube. (Note: If the PRP has a reddish color, discard these samples). Platelets were isolated from PRP by spinning at 800 g for 10 minutes (no brake). The plasma was discarded, and the platelets were resuspended carefully and slowly in Tyrode's buffer (134 mM NaCl, 12 mM $NaHCO_3$, 2.9 mM KCl, 0.34 mM $Na_2HPO_4$, 1 mM $MgCl_2$, 10 mM HEPES, pH 7.4) or PBS including PGE1 (1 μM final concentration) (Note: release the buffer slowly along the tube wall and minimize the amount of agitation). 500-600 μl whole blood was needed for each in vivo injection.

Then, the surface of the platelets was functionalized with aPDL-1 in three steps. First, 100 μL of platelets ($1\times10^8$) was resuspended in 400 μL of PBS (pH=8), including PGE1 (1 μM), and incubated with the Traut's Reagent (0.1 mg/ml) (2-iminothiolane, Pierce) for 30 min at room temperature (RT). After 30 min of reaction, the excess Traut's Reagent was removed by centrifugation at 800 g for 10 minutes and washed with the Tyrode's buffer (including PGE1 (1 μM)) three times (without resuspension in order to avoid unnecessary platelet activation). In the meantime, aPDL-1 was mixed with sulfosuccinimidyl-4-(N-maleimidomethyl)-cyclohexane-1-carboxylate (Sulfo-SMCC, Pierce) in PBS (pH=7.4) at a molar ratio of 1:1.2 for 2 h at 4° C. The excess sulfo-SMCC was removed using a centrifugal filter device (molecular weight cut-off (MWCO)=10 kDa) to purify the SMCC activated-antibody. Lastly, platelets and antibodies were mixed in the Tyrode's buffer (including PGE1 (1 μM)). After 2 h of reaction at RT, the excess antibodies were removed by centrifugation (800 g for 10 minutes). The precipitate fraction was retained and washed with the Tyrode's buffer (including PGE1 (1 μM)) twice. Platelet recovery was higher than 80% after conjunction based on the platelet count analysis. The obtained aPDL1-platelet was stored in Tyrode's buffer (including PGE1 (1 μM)) at room temperature until use. Unconjugated platelets were not separated from conjugated platelets. The final conjugated amount of aPDL1 to platelet was measured by ELISA (Rat IgG total ELISA kit, eBioscience, Cat. No. 88-50490-22). Freshly isolated platelets were used within 6 hours. Platelet activation marker CD62P was used for evaluating platelet activation. All platelet manipulations were performed at room temperature. To study the conjugation efficiency, various amounts of aPDL1 were added into platelets for conjugation. Unconjugated aPDL1 were removed by centrifugation in supernatant (800 g for 10 minutes). The precipitate P-aPDL1 were then washed by the Tyrode's buffer (including PGE1 (1 μM)) twice by centrifugation (800 g for 10 minutes). After that, P-aPDL1 were dissolved in 100 μl deionized water and treated with ultrasound for cell lysis to release aPDL1. The conjugated amount of aPDL1 to platelet was measured by ELISA analysis. The efficiency of aPDL1 conjugation (added aPDL1/conjugated aPDL1) to platelets was about 75% when 0.2 pg aPDL1 per platelet was added. To study the stability of platelets after aPDL1 modification, the number of P-aPDL1 was measured based on the platelet count analysis at the 0 h and 24 h. To study the stability of aPDL1 on platelets over time, P-aPDL1 were stored in Tyrode's buffer (including PGE1 (1 μM)) at RT. 50 μl of P-aPDL1 were extracted at different time. Released aPDL1 in supernatant were removed by centrifugation (800 g for 10 minutes). The P-aPDL1 were dissolved in 100 μl deionized water and treated with ultrasound for lysis to release aPDL1. The conjugated amount of aPDL1 to platelet was measured by ELISA analysis. To activate the platelets, 0.5 U thrombin/mL was added to the platelet suspension. PGE1 was removed prior to platelet activation. Platelets were activated for 30 minutes at 37° C.

PMPs were prepared from platelets as described earlier.[53] Before the experiments, platelet concentrates were activated by thrombin (2 U/mL) for 30 minutes and centrifuged at 800 g for 10 minutes, and the supernatants enriched in PMPs were collected. Supernatant was examined by flow cytometry analysis using anti-mouse αIIbb3 antibody and anti-mouse CD62P (P selectin) antibody. Next, PMPs were coupled with aPDL1 as described above. The coupling efficiency and stability were examined by ELISA.

Transmission Electron Microscopy (TEM)

Pre-fixation of platelets was carried out by mixing platelets with 10% buffered formaldehyde solution in order to avoid shape changes of platelets by the subsequent preparation steps. Immediately after pre-fixation, the samples were centrifuged at 800 g for 10 min at room temperature. After discarding the supernatant, platelets were fixed with 2.5% glutaraldehyde in the cacodylate buffer, pH 7.2, for 90 min at 4° C. (for activated platelets, the supernatant were also collected for TEM imaging). After fixation, platelets were washed twice by centrifugation at 800 g for 10 min at 4° C. Then the platelets were stained with 2% uranyl acetate and lead citrate in sequential steps for 5 min then transferred to the copper grids.[54] The TEM images of platelets were obtained via a JEOL 2000FX TEM instrument at 80 kV.

Anti-PDL1 and Cytokine Release from Platelets

To activate P-aPDL1, 0.5 U thrombin/mL was added to the P-aPDL1 (about $1\times10^8$ platelets in 500 μL. Tyrode's buffer, n=3) suspension at 37° C. 30 min. 50 μl of P-aPDL1 were extracted at different time. aPDL1 and cytokine released from the platelets in the supernatant was collected by centrifugation at 800 g for 10 min. Nonactivated P-aPDL1 was as a control. The amount of released aPDL1 and cytokine in the supernatant solutions were measured by ELISA assay. (eBioscience, Cat. No. 88-50490-22 (rat IgG), 88-7013-22 (IL1β), 88-7064-22 (IL6), 88-7324-22 (TNF-α), BMS6010 (sCD40L)). The absorbance was read on an Infinite® 200 PRO plate reader.

In Vivo Pharmacokinetics

Three mice were i.v. injected with free aPDL1, P-aPDL1 or unconjugated platelets+a-PDL1 mixture (aPDL1, 2 mg/kg, platelets, $2\times10^8$, in 200 μL PBS for each mouse). 10 μL of blood was extracted from the tail at different time points using an anticoagulation tube. The each sample was dissolved in 100 μl water (Sigma, Cat. No. W4502) and treated with ultrasound for cell lysis to release the conjugated aPDL1. The aPDL1 was measured by Rat IgG total ELISA kit (eBioscience, Cat. No. 88-50490-22). For the in vivo biodistribution study, after removal of primary tumor with ~1% residual tissue left behind, the mice were i.v. injected with Cy5.5 labeled free aPDL1 or P-aPDL1. In vivo fluorescence images were recorded by IVIS system (with supplied excitation/emission filters for Cy5.5, exposure time, 1s). For ex vivo imaging, treated mice were sacrificed at 2 h post injection. Major organs and tissues were collected and imaged under an IVIS imaging system (with supplied excitation/emission filters for Cy5.5, exposure time, 1s) (Perkin Elmer Ltd).

In Vivo Tumor Models

To measure the effects on cancer recurrence, 7 days after $1\times10^6$ either B16F10 (or 4T1) or luciferase-tagged B16F10 (or 4T1) tumor cells were transplanted into the right flank of mice (the tumor reaches ~300 mm$^3$); the tumors were resected leaving about 1% residual tissue behind to mimic the residual microtumors in surgical bed[3]. Briefly, animals were anesthetized with isoflurane (1-3% for maintenance; up to 5% for induction) anesthesia via chamber induction and maintained via nose cone. The tumor area was clipped and aseptically prepped. Sterile instruments were used to remove approximately 99% of the tumor. The wound was closed by Autoclip Wound Clip System. For the experimental metastasis model, $1\times10^5$ luciferase-tagged B16F10 (or 4T1) tumor cells in 200 μL PBS were intravenously infused into mice via the tail vein after resection of primary tumor. Mice were weighed and randomly divided into different groups (n=8). After surgery, the mice were i.v. injected with different drug formulations immediately afterwards (aPDL1=1 mg/kg, $1-2\times10^8$ platelets in 200 μL PBS per mouse) (Freshly prepared platelets used here were collected from the same strain of the healthy mice). The tumor burden was monitored by the bioluminescence signal of cancer cells. The mice were clipped and shaved using a depilatory cream before imaging. Images were taken using an IVIS Lumina imaging system (Caliper, USA). The tumors were also measured with a digital caliper. The tumor volume (mm$^3$) was calculated as (long diameter×short diameter$^2$)/2. Metastatic burden was assessed with bioluminescence. Lungs were weighed and micrometastases were counted. Animals were euthanized when exhibiting signs of impaired health or when the volume of the tumor exceeded 2 cm$^3$.

For the metastatic lung tumor in FIG. 5c, India ink was used to better visualize lung metastases following a standard protocol.[55] Mice were sacrificed and tumor burden was quantified unblinded after intratracheal ink (85 ml H$_2$O, 15 ml ink, two drops of ammonia water) injection and fixation with Fekete's solution (5 ml 70% ethanol, 0.5 ml formalin, and 0.25 ml glacial acetic acid). After 2-6 h, tumor lesions were bleached whereas normal lung tissue remained stained.

In addition, the tumors were dissected from the mice after treatment and snap frozen in optimal cutting medium (O.C.T.) for immunofluorescence staining. Fluorescence-labeled secondary antibody was used to detect aPDL1 and platelets or PMPs. For H&E staining, animals with lung tumors were sacrificed for analysis. The lung tissue sections were stained with H&E following the standard protocol. All H&E staining sections were examined under a Leica microscope (Leica DM5500 B).

Cytokine Detection

The local and plasma levels of IL-1β, IL-6, TNF-α, and sCD40L were measured by ELISA (eBioscience). To determine the concentration of different cytokines at the wound, six hours after platelets injection, the wound tissue was collected and cultured at 37° C. for 12 hours. 100 μL of medium was removed and frozen at −80° C. for analysis. To determine the cytokine levels in plasma, six hours after platelets injection, plasma samples were isolated from the mice after various treatments and diluted for analysis. IL-1β, IL-6, TNF-α, and sCD40L concentration was determined by ELISA (Thermo Scientific). All measurements were carried out in triplicate.

Confocal Microscopy

The tumors were dissected from the mice and snap frozen in O.C.T. Several micrometer sections were cut using a cryotome and mounted on slides. Sections were fixed in ice-cold acetone for 10 minutes prior to rehydration with PBS. After blocking with BSA (3%), sections were stained with primary antibodies overnight at 4° C. Following the addition of fluorescence-labeled secondary antibody, the slides were analyzed using a confocal microscope (Zeiss LSM 710).

In Vivo Bioluminescence and Imaging

Bioluminescence images were collected with an IVIS Spectrum Imaging System (Perkin Elmer Ltd). Living Image software (Perkin Elmer Ltd) was used to acquire the data 10 min after intraperitoneal injection of d-luciferin (Thermo Scientific™ Pierce™, Cat #PI88291) in DPBS (15 mg/mL) into the animals (10 μL/g of body weight). Exposure time for bioluminescence imaging was 5 min. (To optimize reading time, bioluminescence intensity was acquired for 30 min with 1 min exposure time using the IVIS Imaging System.) Regions of interest (ROI) were quantified as average radiance (photons s$^{-1}$ cm$^{-2}$ sr$^{-1}$, represented by color bars) (IVIS Living Image 4.2).

Tail Bleeding Assay

Tail bleeding time was determined by removing 3 mm from the tip of the distal mouse tail and immediately immersing the tail in 37° C. PBS. A complete cessation of bleeding was defined as the end point of bleeding time.

Statistical Analysis

All results are expressed as mean±s.d., mean±s.e.m. as indicated. Biological replicates were used in all experiments unless stated otherwise. One-way analysis of variance (ANOVA) was performed when more than two groups were compared, and when determined significant (P≤0.05), multiple comparisons were performed using Tukey's post-hoc test. Survival benefit was determined with the log-rank test. All statistical analyses were performed with GraphPad Prism (5.0). *P≤0.05, P≤0.01, *P≤0.001. No statistical methods were used to pre-determine sample size for animal or other experiments.

REFERENCES

1. Baker, D., Masterson, T., Pace, R., Constable, W. & Wanebo, H. The influence of the surgical wound on local tumor recurrence. *Surgery* 106, 525-532 (1989).
2. Lukianova-Hleb, E. Y. et al. Intraoperative diagnostics and elimination of residual microtumors with plasmonic nanobubbles. *Nat. Nanotechnol.* (2016).
3. Stephan, S. B. et al. Biopolymer implants enhance the efficacy of adoptive T-cell therapy. *Nat. Biotechnol.* 33, 97-101 (2015).
4. Demicheli, R., Retsky, M., Hrushesky, W., Baum, M. & Gukas, I. The effects of surgery on tumor growth: a century of investigations. *Ann. Oncol.*, mdn386 (2008).
5. Ceelen, W., Pattyn, P. & Mareel, M. Surgery, wound healing, and metastasis: Recent insights and clinical implications. *Crit. Rev. Oncol. Hematol.* 89, 16-26 (2014).
6. Klevorn, L. E. & Teague, R. M. Adapting Cancer Immunotherapy Models for the Real World. *Trends Immunol.* (2016).
7. O'Sullivan, D. & Pearce, E. L. Targeting T cell metabolism for therapy. *Trends Immunol.* 36, 71-80 (2015).
8. Robert, C. et al. Pembrolizumab versus Ipilimumab in Advanced Melanoma. *N. Engl. J. Med.* 372, 2521-2532 (2015).
9. Postow, M. A. et al. Nivolumab and ipilimumab versus ipilimumab in untreated melanoma. *N. Engl. J. Med.* 372, 2006-2017 (2015).
10. Sharma, P. & Allison, J. P. The future of immune checkpoint therapy. *Science* 348, 56-61 (2015).
11. Wang, C., Ye, Y, Hochu, G. M., Sadeghifar, H. & Gu, Z. Enhanced Cancer Immunotherapy by Microneedle Patch-Assisted Delivery of Anti-PD1 Antibody. *Nano Lett.* 16, 2334-2340 (2016).
12. Zou, W., Wolchok, J. D. & Chen, L. PD-L1 (B7-H1) and PD-1 pathway blockade for cancer therapy: Mechanisms, response biomarkers, and combinations. *Sci. Transl. Med.* 8, 328rv324 (2016).
13. Buchbinder, E. I. & Hodi, F. S. Melanoma in 2015: Immune-checkpoint blockade—durable cancer control. *Nat. Rev. Clin. Oncol.* 13, 77-78 (2016).
14. Smyth, E. C. & Cunningham, D. Encouraging results for PD-1 inhibition in gastric cancer. *Lancet Oncol.* (2016).
15. Rosenberg, J. E. et al. Atezolizumab in patients with locally advanced and metastatic urothelial carcinoma who have progressed following treatment with platinum-based chemotherapy: a single-arm, multicentre, phase 2 trial. *The Lancet* 387, 1909-1920 (2016).
16. Naidoo, J. et al. Toxicities of the anti-PD-1 and anti-PD-L1 immune checkpoint antibodies. *Ann. Oncol.*, mdv383 (2015).
17. Mellati, M. et al. Anti-PD-1 and Anti-PDL-1 Monoclonal Antibodies Causing Type 1 Diabetes. *Diabetes Care* 38, e137-138 (2015).
18. Boutros, C. et al. Safety profiles of anti-CTLA-4 and anti-PD-1 antibodies alone and in combination. *Nat. Rev. Clin. Oncol.* (2016).
19. Larkin, J. et al. Combined Nivolumab and Ipilimumab or Monotherapy in Untreated Melanoma. *N. Engl. J. Med.* 373, 23-34 (2015).
20. Chen, L. & Han, X. Anti-PD-1/PD-L1 therapy of human cancer: past, present, and future. *J. Clin. Invest.* 125, 3384-3391 (2015).
21. Weber, J. S., Kahler, K. C. & Hauschild, A. Management of immune-related adverse events and kinetics of response with ipilimumab. *J. Clin. Oncol.* 30, 2691-2697 (2012).
22. Woo, S. R., Corrales, L. & Gajewski, T. F. The STING pathway and the T cell-inflamed tumor microenvironment. *Trends Immunol.* 36, 250-256 (2015).
23. Hegde, P. S., Karanikas, V. & Evers, S. The where, the when, and the how of immune monitoring for cancer immunotherapies in the era of checkpoint inhibition. *Clin. Cancer Res.* 22, 1865-1874 (2016).
24. Spranger, S. et al. Up-regulation of PD-L1, IDO, and Tregs in the melanoma tumor microenvironment is driven by CD8+ T cells. *Sci. Transl. Med.* 5, 200ra116-200ra116 (2013).
25. Gajewski, T. F., Schreiber, H. & Fu, Y. X. Innate and adaptive immune cells in the tumor microenvironment. *Nat. Immunol.* 14, 1014-1022 (2013).
26. Fesnak, A. D., June, C. H. & Levine, B. L. Engineered T cells: the promise and challenges of cancer immunotherapy. *Nat. Rev. Cancer* 16, 566-581 (2016).
27. Yoo, J. W., Irvine, D. J., Discher, D. E. & Mitragotri, S. Bio-inspired, bioengineered and biomimetic drug delivery carriers. *Nat. Rev. Drug Discov.* 10, 521-535 (2011).
28. Tamagawa-Mineoka, R. Important roles of platelets as immune cells in the skin. *J. Dermatol. Sci.* 77, 93-101 (2015).
29. Franco, A. T., Corken, A. & Ware, J. Platelets at the interface of thrombosis, inflammation, and cancer. *Blood* 126, 582-588 (2015).
30. Hu, C. M. et al. Nanoparticle biointerfacing by platelet membrane cloaking. *Nature* 526, 118-121 (2015).
31. Textor, J. in Platelet-Rich Plasma 61-94 (Springer, 2014).
32. Harker, L. A. et al. Effects of megakaryocyte growth and development factor on platelet production, platelet life span, and platelet function in healthy human volunteers. *Blood* 95, 2514-2522 (2000).
33. Nurden, A. T., Nurden, P., Sanchez, M., Andia, I. & Anitua, E. Platelets and wound healing. *Front Biosci.* 13, 3532-3548 (2008).
34. Gay, L. J. & Felding-Habermann, B. Contribution of platelets to tumor metastasis. *Nat. Rev. Cancer* 11, 123-134 (2011).
35. Nash, G. F., Turner, L. F., Scully, M. F. & Kakkar, A. K. Platelets and cancer. *Lancet Oncol.* 3, 425-430 (2002).
36. Hu, Q. et al. Anticancer Platelet-Mimicking Nanovehicles. *Adv. Mater.* 27, 7043-7050 (2015).
37. Garraud, O. Editorial: Platelets as immune cells in physiology and immunopathology. *Front Immunol.* 6, 1-3 (2015).
38. Morrell, C. N., Aggrey, A. A., Chapman, L. M. & Modjeski, K. L. Emerging roles for platelets as immune and inflammatory cells. *Blood* 123, 2759-2767 (2014).
39. Semple, J. W., Italiano, J. E. & Freedman, J. Platelets and the immune continuum. *Nat. Rev. Immunol.* 11, 264-274 (2011).
40. Elzey, B. D. et al. Platelet-mediated modulation of adaptive immunity: A communication link between innate and adaptive immune compartments. *Immunity* 19, 9-19 (2003).
41. Seifert, L. et al. The necrosome promotes pancreatic oncogenesis via CXCL1 and Mincle-induced immune suppression. *Nature* 532, 245-249 (2016).

42. Topalian, S. L., Drake, C. G. & Pardoll, D. M. Targeting the PD-1/B7-H1(PD-L1) pathway to activate anti-tumor immunity. *Curr. Opin. Immunol.* 24, 207-212 (2012).
43. Siljander, P. R. M. Platelet-derived microparticles—an updated perspective. *Thromb. Res.* 127, S30-S33 (2011).
44. Li, J., Sharkey, C. C., Wun, B., Liesveld, J. L. & King, M. R. Genetic engineering of platelets to neutralize circulating tumor cells. *J. Control Release* 228, 38-47 (2016).
45. Ruggeri, Z. M. & Mendolicchio, G. L. Adhesion mechanisms in platelet function. *Circ. Res.* 100, 1673-1685 (2007).
46. Mause, S. F., von Hundelshausen, P., Zernecke, A., Koenen, R. R. & Weber, C. Platelet microparticles—A transcellular delivery system for RANTES promoting monocyte recruitment on endothelium. *Arterioscler. Thromb. Vasc. Biol.* 25, 1512-1518 (2005).
47. Tripathi, S. & Guleria, I. Role of PD1/PDL1 pathway, and TH17 and treg cells in maternal tolerance to the fetus. *Biomed. J.* 38, 25-31 (2015).
48. Headley, M. B. et al. Visualization of immediate immune responses to pioneer metastatic cells in the lung. *Nature* 531, 513-517 (2016).
49. Flaumenhaft, R. Formation and fate of platelet microparticles. *Blood Cells Mol. Dis.* 36, 182-187 (2006).
50. Rand, M. L., Wang, H., Bang, K. W., Packham, M. A. & Freedman, J. Rapid clearance of procoagulant platelet-derived microparticles from the circulation of rabbits. *J. Thromb Haemost* 4, 1621-1623 (2006).
51. Lu, Y., Aimetti, A. A., Langer, R. & Gu, Z. Bioresponsive materials. *Nature Reviews Materials* 1, 16075 (2016).
52. Cazenave, J. -P. et al. Preparation of washed platelet suspensions from human and rodent blood. *Platelets and Megakaryocytes: Volume 1: Functional Assays,* 13-28 (2004).
53. Janowska-Wieczorek, A. et al. Platelet-derived microparticles bind to hematopoietic stem/progenitor cells and enhance their engraftment after transplantation. *Blood* 98, 645a-645a (2001).
54. Cheville, N. F. & Stasko, J. Techniques in electron microscopy of animal tissue. *Veterinary pathology* 51, 28-41 (2014).
55. Zimmerman, M., Hu, X. & Liu, K. Experimental metastasis and CTL adoptive transfer immunotherapy mouse model. *Journal of visualized experiments: JOVE* (2010).
56. Wang, C. et al. Dataset for In situ Activation of Platelets with Checkpoint Inhibitors for Post-Surgical Cancer Immunotherapy. Figshare http://dx.doi.org/10.6084/m9.figshare.4231766 (2016).

Unless defined otherwise, all technical and scientific terms used herein have the same meanings as commonly understood by one of skill in the art to which the disclosed invention belongs. Publications cited herein and the materials for which they are cited are specifically incorporated by reference.

Those skilled in the art will appreciate that numerous changes and modifications can be made to the preferred embodiments of the invention and that such changes and modifications can be made without departing from the spirit of the invention. It is, therefore, intended that the appended claims cover all such equivalent variations as fall within the true spirit and scope of the invention.

We claim:

1. A composition comprising:
   a platelet cell;
   a chemical linker moiety; and
   a therapeutic agent;
   wherein the therapeutic agent is covalently linked to the platelet cell through the chemical linker moiety;
   wherein the therapeutic agent is an immunotherapeutic agent selected from an anti-PDL1 antibody, an anti-PD1 antibody, an anti-CTLA4 antibody, an anti-CD47 antibody, or a combination thereof; and
   wherein the therapeutic agent is released in platelet-derived microparticles from the platelet cell upon activation of the platelet cell.

2. The composition of claim 1, wherein the immunotherapeutic agent is an anti-PDL1 antibody.

3. The composition of claim 1, wherein the immunotherapeutic agent is an anti-PD1 antibody.

4. The composition of claim 1, wherein the chemical linker moiety is selected from a maleimide linker, a PEG linker, PASylation, and HESylation.

5. The composition of claim 4, wherein the chemical linker moiety is a maleimide linker.

6. The composition of claim 1, wherein the platelet cell is a human platelet cell.

7. The composition of claim 1, wherein the platelet cell is an autologous platelet cell.

8. A method of preventing metastasis or recurrence of a solid tumor after surgical resection, the method comprising:
   administering to a subject in need thereof a therapeutically effective amount of the composition of claim 1,
   wherein the therapeutic agent is released in platelet-derived microparticles from the platelet cell upon activation of the platelet cell at the surgical resection site.

9. The method of claim 8, wherein the solid tumor is melanoma.

10. The method of claim 8, wherein the solid tumor is breast cancer.

11. The method of claim 8, wherein the composition is administered in combination with an additional therapeutic agent.

12. The method of claim 11, wherein the additional therapeutic agent is an antineoplastic agent.

\* \* \* \* \*